United States Patent
Wang et al.

(10) Patent No.: US 11,779,592 B2
(45) Date of Patent: Oct. 10, 2023

(54) INHIBITION OF NGLY1 FOR THE TREATMENT OF CANCER

(71) Applicant: University of North Texas Health Science Center, Fort Worth, TX (US)

(72) Inventors: Yu-Chieh Wang, Fort Worth, TX (US); Victor J. T. Lin, Fort Worth, TX (US); Ashwini Zolekar, Fort Worth, TX (US); Kyle A. Emmitte, Aledo, TX (US); Nigam M. Mishra, Fort Worth, TX (US); Jin Liu, Dallas, TX (US)

(73) Assignee: UNIVERSITY OF NORTH TEXAS HEALTH SCIENCE CENTER, Fort Worth, TX (US)

( * ) Notice: Subject to any disclaimer, the term of this patent is extended or adjusted under 35 U.S.C. 154(b) by 335 days.

(21) Appl. No.: 16/639,027

(22) PCT Filed: Aug. 14, 2018

(86) PCT No.: PCT/US2018/046618
§ 371 (c)(1),
(2) Date: Feb. 13, 2020

(87) PCT Pub. No.: WO2019/036417
PCT Pub. Date: Feb. 21, 2019

(65) Prior Publication Data
US 2021/0205349 A1 Jul. 8, 2021

Related U.S. Application Data

(60) Provisional application No. 62/545,244, filed on Aug. 14, 2017.

(51) Int. Cl.
*A61K 31/7105* (2006.01)
*A61P 35/00* (2006.01)
*C07D 309/14* (2006.01)
*C12N 15/113* (2010.01)
*A61K 45/06* (2006.01)

(52) U.S. Cl.
CPC .......... *A61K 31/7105* (2013.01); *A61P 35/00* (2018.01); *C07D 309/14* (2013.01); *C12N 15/1137* (2013.01); *A61K 45/06* (2013.01); *C12Y 305/01052* (2013.01)

(58) Field of Classification Search
CPC ... A61P 35/00; C07D 309/14; C12N 15/1137; A61K 45/06; C12Y 305/01052
See application file for complete search history.

(56) References Cited

FOREIGN PATENT DOCUMENTS

| JP | H 09173094 | 7/1997 | |
|---|---|---|---|
| WO | WO-2015081282 A1 * | 6/2015 | ......... A61K 31/5386 |
| WO | WO 2018/144327 | 8/2018 | |
| WO | WO 2019/036417 | 2/2019 | |

OTHER PUBLICATIONS

Almond & Cohen, "The proteasome: a novel target for cancer chemotherapy." *Leukemia*; 16, 433-443, 2002.
Anderson DJ, Le Moigne R, Djakovic S, Kumar B, Rice J, Wong S et al. "Targeting the AAA ATPase p97 as an Approach to Treat Cancer through Disruption of Protein Homeostasis." *Cancer cell*; 28(5): 653-665, 2015.
Bhatia et al., "Treatment of metastatic melanoma: an overview," Oncology (Williston Park), 23:488-496, 2009.
Biasini et al., "Swiss-Model: modelling protein tertiary and quaternary structure using evolutionary information." *Nucleic acids research*, 2014.
Bidwell BN, Slaney CY, Withana NP, Forster S, Cao Y, Loi S et al. "Silencing of Irf7 pathways in breast cancer cells promotes bone metastasis through immune escape." *Nature medicine*; 18(8): 1224-1231, 2012.
Caglayan et al., "NGLY1 mutation causes neuromotor impairment, intellectual disability, and neuropathy", *European Journal of Medical Genetics*, 58:39-43, 2015.
Cao et al., "Stereoselective synthesis of quercetin 3-O-glycosides of 2-amino-2-deoxy-D-glucose under phase transfer catalytic conditions." *Journal of Carbohydrate Chemistry*; 34, 28-40, 2015.

(Continued)

*Primary Examiner* — J. E. Angell
(74) *Attorney, Agent, or Firm* — Parker Highlander PLLC

(57) ABSTRACT

In one aspect, the present disclosure provides GlcNAc-Asn analogs of the formula (I): wherein the variables are as defined herein. In another aspect, the present disclosure also provides pharmaceutical compositions and methods of using the compounds disclosed herein. Additionally, the present disclosure also provides methods of treating cancer comprising inhibiting NGLY1.

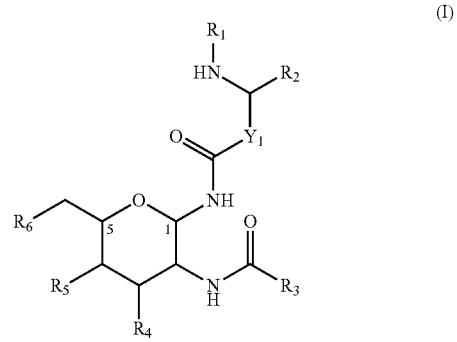

11 Claims, 47 Drawing Sheets

Specification includes a Sequence Listing.

(56) References Cited

OTHER PUBLICATIONS

Cerezo et al., "Compounds Triggering ER Stress Exert Anti-Melanoma Effects and Overcome BRAF Inhibitor Resistance," *Cancer cell*; 30(1): 183, 2016.
Chapman et al., "Improved survival with vemurafenib in melanoma with BRAF V600E mutation," *N Engl J Med.*, 364:2507-2516, 2011.
Chen et al., "Bortezomib as the first proteasome inhibitor anticancer drug: current status and future perspectives." *Current cancer drug targets*; 11, 239-253, 2011.
Ellis and Hicklin, "Resistance to Targeted Therapies: Refining Anticancer Therapy in the Era of Molecular Oncology," *Clin Cancer Res.*, 15:7471-7478, 2009.
Enns et al., "Mutations in NGLY1 cause an inherited disorder of the endoplasmic reticulum-associated degradation pathway," *Genetics in Medicine*, 16:751-758, 2014.
Erdem-Eraslan et al., "Mutation specific functions of EGFR result in a mutation-specific downstream pathway activation" *Eur J Cancer*, 51(7):893-903, 2015.
Falkenius J, Lundeberg J, Johansson H, Tuominen R, Frostvik-Stolt M, Hansson J et al. "High expression of glycolytic and pigment proteins is associated with worse clinical outcome in stage III melanoma." *Melanoma research*; 23(6): 452-460, 2013.
Flaherty et al., "Vemurafenib", *Nat Rev Drug Discov.*, 10:811-812, 2011.
Flanagan et al., "Chemical and computational methods for the characterization of covalent reactive groups for the prospective design of irreversible inhibitors." *Journal of medicinal chemistry*; 57, 10072-10079, 2014.
Friesner et al., "Glide: a New Approach for Rapid, Accurate Docking and Scoring. 1. Method and Assessment of Docking Accuracy." *Journal of Medicinal Chemistry*; 47, 1739-1749, 2004.
Funakoshi et al., "Evidence for an Essential Deglycosylation—Independent Activity of PNGase in Drosophila melanogaster," *PloS One*; 5:e10545, 2010.
Goplen D, Bougnaud S, Rajeevie U, Boe SO, Skaftnesmo KO, Voges J et al. "alphaB-crystallin is elevated in highly infiltrative apoptosis-resistant glioblastoma cells". *The American journal of pathology*; 177(4): 1618-1628, 2010.
Hagihara et al., "Fluorescently labeled inhibitor for profiling cytoplasmic peptide:N-glycanase" *Glycobiology*, 17(10):1070-6, 2007.
Hassan M, Alaoui A, Feyen O, Mirmohammadsadegh A, Essmann F, Tannapfel A et al. "The BH3-only member Noxa causes apoptosis in melanoma cells by multiple pathways." *Oncogene*, 27(33): 4557-4568, 2008.
Heeley & Shinawi, "Multi-systemic involvement in NGLY1-related disorder caused by two novel mutations." *American journal of medical genetics. Part A*, 2015.
Hodi et al., "Improved survival with ipilimumab in patients with metastatic melanoma," *N Engl J Med.*, 363:711-723, 2010.
Hossain et al., "Dinaciclib induces immunogenic cell death and enhances anti-PD1-mediated tumor suppression" *Journal of Clinical Investigation*, 128: 644-654, 2018.
Huang et al. "Endo-β-N-acetylglucosaminidase forms N-GlcNAc protein aggregates during ER-associated degradation in Ngly1-defective cells" *Proc Natl Acad Sci USA*, 112:1398-1403, 2015.
Inazu & Kobayashi, "New Simple Method for the Synthesis of Nα-Fmoc-Nβ-Glycosylated-L-Asparagine Derivatives." *Synlett*; 869-870, 1993.
International Search Report and Written Opinion issued in corresponding PCT Application No. PCT/US2018/46618, dated Dec. 21, 2018.
Ishiguro H, Tsunoda T, Tanaka T, Fujii Y, Nakamura Y, Furukawa Y. "Identification of AXUD1, a novel human gene induced by AXIN1 and its reduced expression in human carcinomas of the lung, liver, colon and kidney." *Oncogene*; 20(36): 5062-5066, 2001.
Ivashkiv LB, Donlin LT. "Regulation of type I interferon responses." *Nature reviews Immunology*; 14(1): 36-49, 2014.
Jalili A, Wagner C, Pashenkov M, Pathria G, Mertz KD, Widlund HR et al. "Dual suppression of the cyclin-dependent kinase inhibitors CDKN2C and CDKN1A in human melanoma." *Journal of the National Cancer Institute*; 104(21): 1673-1679, 2012.
Jones et al., "Melanocytes derived from transgene-free human induced pluripotent stem cells." *The Journal of investigative dermatology*; 133, 2104-2108, 2013.
Koizumi S, Irie T, Hirayama S, Sakurai Y, Yashiroda H, Naguro I et al. "The aspartyl protease DDI2 activates Nrf1 to compensate for proteasome dysfunction." *eLife*; 5; 2016.
Kuhn et al., "Potent activity of carfilzomib, a novel, irreversible inhibitor of the ubiquitin-proteasome pathway, against preclinical models of multiple myeloma" *Blood*, 110:3281-3290, 2007.
Kunz et al., "High-throughput sequencing of the melanoma genome," *xp Dermatol*, 22(1):10-7, 2013.
Kuo TF, Chen Ty, Jiang ST, Chen KW, Chiang YM, Hsu YJ et al. "Protein disulfide isomerase a4 acts as a novel regulator of cancer growth through the procaspase pathway." *Oncogene*; 36(39): 5484-5496, 2017.
Lam et al., "Prospective phenotyping of NGLY1-CDDG, the first congenital disorder of deglycosylation. " *Genetics in medicine : official journal of the American College of Medical Genetics*, 19(2)160-168, 2016.
Lee et al., "Proteasome inhibitors disrupt the unfolded protein response in myeloma cells." *Proceedings of the National Academy of Sciences of the United States of America*; 100, 9946-9951, 2003.
Lehrbach NJ, Ruvkun G. "Proteasome dysfunction triggers activation of SKN-1A/Nrf1 by the aspartic protease DDI-1." *eLife*; 5; 2016.
Ley et al., "Multi-step organic synthesis using solid-supported reagents and scavengers: a new paradigm in chemical library generation." *J Chem Soc Perkin Trans 1*; 24, 3815-4195, 2000.
Li et al., "Synthesis and analysis of potential DNA intercalators containing quinoline-glucose hybrids." *Chemical biology & drug design*; 74, 80-86, 2009.
Liao et al., "Matched miRNA and mRNA signatures from an hESC-based in Vitro model of pancreatic differentiation reveal novel regulatory interactions." *Journal of cell science*; 126, 3848-3861, 2013.
Liu et al., "Developing irreversible inhibitors of the protein kinase cysteinome." *Chemistry & biology*; 20, 146-159, 2013.
Luchansky et al., "Metabolic functionalization of recombinant glycoproteins."*Biochemistryl*; 43, 12358-12366, 2004.
Luethy and Holbrook, "Activation of the gadd153 promoter by genotoxic agents: a rapid and specific response to DNA damage." *Cancer research*; 52(1): 5-10, 1992.
Maerz et al., "The Neurospora Peptide:N-Glycanase Ortholog PNG1 Is Essential for Cell Polarity despite Its Lack of Enzymatic Activity" *The Journal of Biological Chemistry*; 285:2326-2332, 2010.
Marks, P.A. "The clinical development of histone deacetylase inhibitors as targeted anticancer drugs." *Expert opinion on investigational drugs*; 19, 1049-1066, 2010.
Misaghi et al., "Using a small molecule inhibitor of peptide: N-glycanase to probe its role in glycoprotein turnover." *Chemistry & biology*; 11, 1677-1687, 2004.
Morris et al., "AutoDock4 and AutoDockTools4: Automated docking with selective receptor flexibility." *Journal of computational chemistry*; 30, 2785-2791, 2009.
Nazor et al., "Recurrent variations in DNA methylation in human pluripotent stem cells and their differentiated derivatives." *Cell stem cell*; 10, 620-634, 2012.
Need et al. "Clinical application of exome sequencing in undiagnosed genetic conditions" *Journal of Medical Genetics*, 49:353-361, 2012.
Noguchi et al., "Convenient primary amidation of N-protected phenylglycine and dipeptides without racemization or epimerization." *Tetrahedron Letters*; 55, 394-396, 2014.
Orita et al., "Highly efficient deacetylation by use of the neutral organotin catalyst [tBu2SnOH(CI)]2." *Chemistry*; 7, 3321-3327, 2001.
Orlowski and Kuhn, "Proteasome inhibitors in cancer therapy: lessons from the first decade" *Clinical Cancer Research*, 14:1649-1657, 2008.

(56) References Cited

OTHER PUBLICATIONS

Owings KG, Lowry JB, Bi Y, Might M, Chow CY. "Transcriptome and functional analysis in a *Drosophila* model of NGLY1 deficiency provides insight into therapeutic approaches." *Human molecular genetics*; 27(6): 1055-1066, 2018.

Powers et al., "Irreversible inhibitors of serine, cysteine, and threonine proteases." *Chemical reviews*; 102, 4639-4750, 2002.

Reu FJ, Bae SI, Cherkassky L, Leaman DW, Lindner D, Beaulieu N et al. Overcoming resistance to interferon-induced apoptosis of renal carcinoma and melanoma cells by DNA demethylation. *Journal of clinical oncology : official journal of the American Society of Clinical Oncology*; 24(23): 3771-3779, 2006.

Singh et al., "The resurgence of covalent drugs." *Nature reviews. Drug discovery*; 10, 307-317, 2011.

Slipicevic A, Jorgensen K, Skrede M, Rosnes AK, Troen G, Davidson B et al. "The fatty acid binding protein 7 (FABP7) is involved in proliferation and invasion of melanoma cells." *BMC cancer*; 8: 276, 2008.

Sondak et al., "Ipilimumab" *Nat Rev Drug Discov.*, 10:411-412, 2011.

Sosman, "Cytotoxic chemotherapy for metastatic melanoma" www.uptodate.com/contents/cytotoxic-chemotherapy-for-metastatic-melanoma.

Suzuki T. "The cytoplasmic peptide:N-glycanase (Ngly1)-basic science encounters a human genetic disorder." *Journal of biochemistry*; 157(1): 23-34; 2015.

Tomlin et al., "Inhibition of NGLY1 Inactivates the Transcription Factor Nrf1 and Potentiates Proteasome Inhibitor Cytotoxicity." *ACS Cent Sci* 2017.

Toyama and Hetzer, "Protein homeostasis: live long, won't prosper" *Nature Reviews. Molecular Cell Biology*, 14:55-61, 2013.

Tropper et al., "Phase Transfer Catalysis as a General and Stereoselective Entry into Glycosyl Azides from Glycosyl Halides." *Synthesis*; 618-620, 1992.

Tsabedze et al., "The development of N-aryl trifluoroacetimidate-based benzyl and allyl protecting group reagents." *Tetrahedron Letters*; 54, 6983-6985, 2013.

Tseng et al., "Overcoming Trastuzumab Resistance in HER2-Overexpressing Breast Cancer Cells by Using a Novel Celecoxib-Derived Phosphoinositide-Dependent Kinase-1 Inhibitor" *Mol Pharmacol.*, 70: 1534-1541, 2006.

Vert A, Castro J, Ribo M, Benito A, Vilanova M. "Activating transcription factor 3 is crucial for antitumor activity and to strengthen the antiviral properties of Onconase." *Oncotarget* 2017; 8(7): 11692-11707; doi 10.18632/oncotarget.14302.

Wang et al., "Protein post-translational modifications and regulation of pluripotency in human stem cells." *Cell research*; 24(2): 143-160, 2014.

Wang et al., "Specific lectin biomarkers for isolation of human pluripotent stem cells identified through array-based glycomic analysis." *Cell research*; 21, 1551-1563, 2011.

Wang et al., "Targeting Endoplasmic Reticulum Stress and Akt with OSU-03012 and Gefitinib or Erlotinib to Overcome Resistance to Epidermal Growth Factor Receptor Inhibitors" *Cancer Research*, 68:2820-2830, 2008.

Wang R, Zheng X, Zhang L, Zhou B, Hu H, Li Z et al. "Histone H4 expression is cooperatively maintained by IKKbeta and Akt1 which attenuates cisplatin-induced apoptosis through the DNA-PK/RIP1/IAPs signaling cascade". *Scientific reports*; 7: 41715, 2017.

Witte et al., "Synthesis and biological evaluation of a chitobiose-based peptide N-glycanase inhibitor library." *The Journal of organic chemistry*; 74, 605-616, 2009.

Wolkenberg et al., "Applications of microwave-assisted organic synthesis on the multigram scale." *Current opinion in drug discovery & development*; 8, 701-708, 2005.

www.proteinatlas.org/ENSG00000151092-NGLY1/tissue; www.proteinatlas.org/ENSG00000151092-NGLY1/cancer.

Zhao et al., Structure of the mouse peptide N-glycanase-HR23 complex suggests co-evolution of the endoplasmic reticulum-associated degradation and DNA repair pathways. *The Journal of biological chemistry*; 281, 13751-13761, 2006.

Zolekar, et al. Stress and interferon signalling-mediated apoptosis contributes to pleiotropic anticancer responses induced by targeting NGLY1. *Br J Cancer* 119, 1538-1551, 2018. https://doi.org/10.138/s41416-018-0265-9.

\* cited by examiner

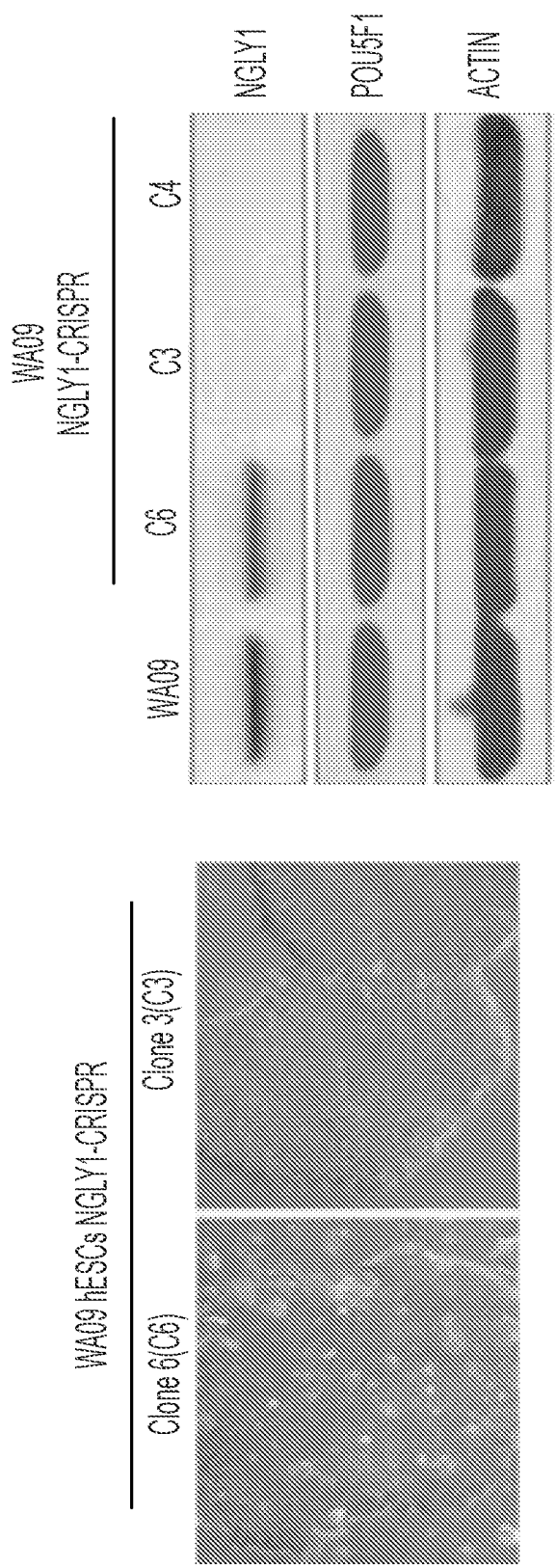
FIG. 2A
FIG. 2B
FIG. 2C

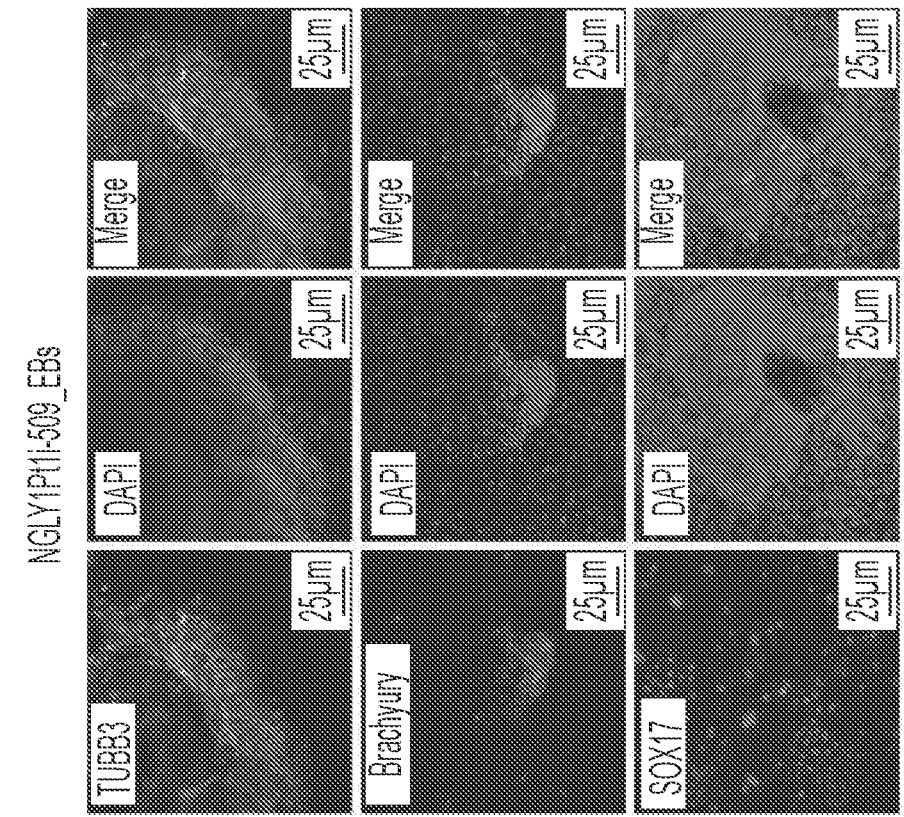
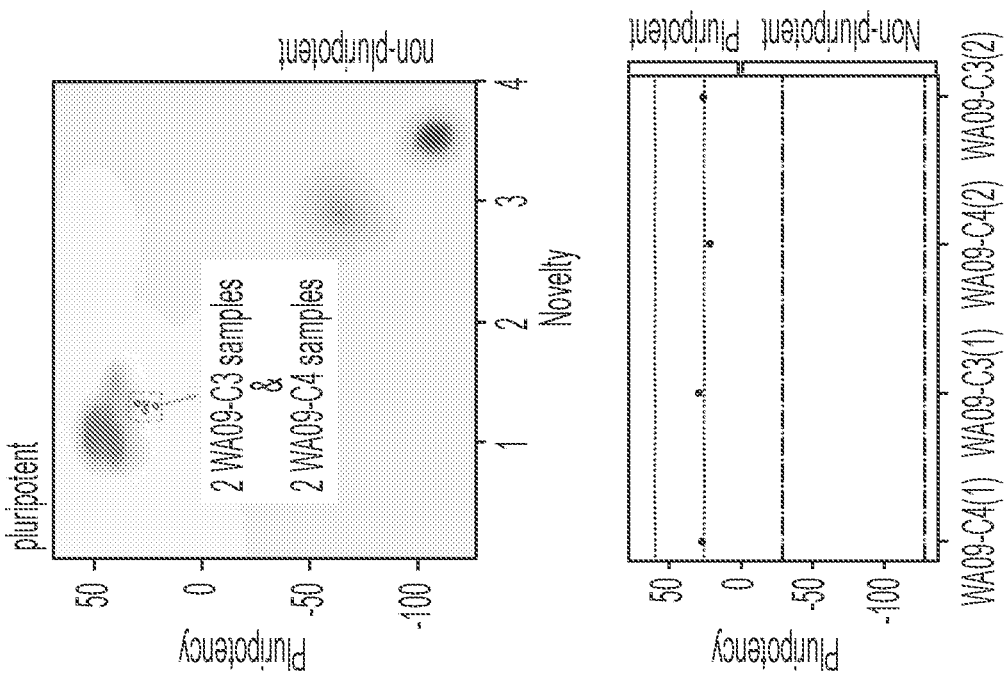
FIG. 4B
FIG. 4A

Mass spec information for GlcNAc modified peptides

| Modified peptide sequence[a] | Positions within proteins | UniProt accession number | Protein names | Localization prob.[b] | PEP[c] | Charge state | m/z | Mass error (ppm) | Score[d] |
|---|---|---|---|---|---|---|---|---|---|
| NLNPKKFSIHDQDHK | 54 | Q9NZH6 | Interleukin-37 (IL37) | 1.0 | 0.0292 | 2 | 1012.51343 | +1.1 | 56.3 |
| RNGSIVSMNLK | 446 | Q92953 | Potassium voltage-gated channel subfamily B member 2 (KCNB2) | 1.0 | 0.0342 | 2 | 812.914169 | -0.9 | 40.2 |
| RNGSIVSMNLK | 453 | Q92953 | Potassium voltage-gated channel subfamily B member 2 (KCNB2) | 1.0 | 0.0342 | 2 | 812.914169 | -0.9 | 40.2 |
| AVAPVMNNQK | 301 | Q96922 | Probable tubulin polyglutamylase TTLL1 (TTLL1) | 1.0 | 0.0209 | 2 | 639.305736 | -1.1 | 76.2 |
| VENALNNLDDGASPGDR | 1514 | Q13796 | Protein Shroom2 (SHROOM2) | 0.6 | 0.0123 | 2 | 980.448147 | 1.7 | 73.3 | a.Underlined amino acid was GlcNac modified
b.Localization probability calculated by Max. Quant Value less then 0.75 was considered true positive
c.Posterior Error Probability (PEP_of the identification, it is basically treated as p-value where less 0.05 was considered significant
d.Andromeda score for the best associated MS/MS spectrum, where higher is better.

FIG. 7C

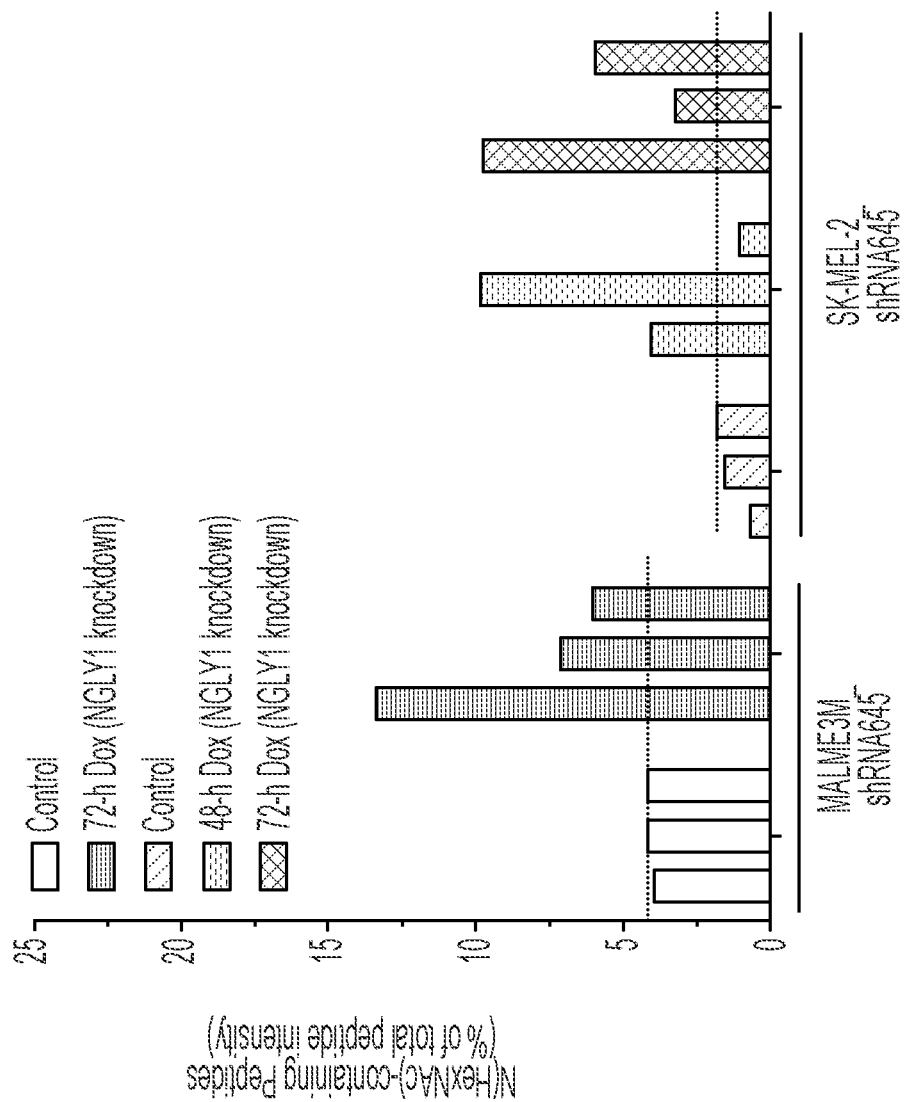

INHIBITION OF NGLY1 FOR THE TREATMENT OF CANCER

This application is a national phase application under 35 U.S.C. § 371 of International Application No. PCT/US2018/046618, filed Aug. 14, 2018, which claims the benefit of U.S. Provisional Application No. 62/545,244, filed on Aug. 14, 2017, the entire contents of each of which is hereby incorporated by reference.

This Invention was made with government support under RP170301 awarded by the Cancer Prevention and Research Institute of Texas. The government has certain rights in the invention.

BACKGROUND

1. Field

This disclosure relates to the fields of medicine, pharmacology, chemistry, and oncology. In particular, new compounds, compositions, and methods of treatment relating to analogs of N-acetylglucosamine-asparagine (GlcNAc-Asn) are disclosed.

2. Related Art

When melanoma progresses to an advanced (metastatic) stage, the number of available and effective treatments for patients become very limited. Traditional therapeutic approaches often elicit severe side effects without improving survival outcomes in patients with metastatic melanoma (Bhatia et al., 2009). Two targeted therapy agents, including vemurafenib and ipilimumab, are favored for treating metastatic melanoma. Vemurafenib (PLX4032 or RG7204) is a small-molecule inhibitor that modulates BRAF activity (Flaherty et al., 2011), and ipilimumab (MDX-010) is an anti-CTLA-4 monoclonal antibody that leads to the activation of cytotoxic T lymphocytes by blocking their inhibitory signals (Sondak et al., 2011). Recently, several additional small molecule inhibitors (dabrafenib and trametinib) that target hyperactive MAPK signaling and a humanized monoclonal antibody (nivolumab) against human programmed death receptor-1 (PD-1) in melanoma cells have also been approved by FDA for clinical use. Despite the distinct pharmacological mechanisms of their anticancer effects, these therapeutic agents have demonstrated desirable efficacy in clinical trials, leading to partial or complete responses with manageable side effects in certain populations of patients with metastatic melanoma (Chapman et al., 2011; Hodi et al., 2010). However, many patients appear to be nonresponders for ipilimumab treatment, and patients presenting with significant tumor regression following initial vemurafenib treatment do not always maintain long-term disease remission. Well-known cases of resistance to other targeted therapies (e.g., imatinib, gefitinib, erlotinib and bevacizumab) have suggested that some cancer cells can harbor or acquire multiple mechanisms to bypass the treatment-induced suppression of survival signals (Ellis and Hicklin, 2009; Wang et al., 2008; Tseng et al., 2006).

The use of proteasome inhibitors as anticancer agents suggests that the proteasome-mediated protein degradation, a well-known molecular component involved in proteostasis, is highly demanded by cancer cells to sustain their viability or oncogenic signaling. N-glycanase 1 (NGLY1) is a protein linked with proteostasis perturbation-induced cell responses and their underlying molecular mechanisms, but this particular protein target has not been studied for anticancer therapies. Thus, there is clearly an unmet medical need in cancer therapy, specifically melanoma therapy, that waits to be addressed by the identification and characterization of new targets, such as NGLY1, and the development of new treatments based on these potential targets.

SUMMARY

In some aspects, the present disclosure provides the use of NGLY1 as a newly-identified anticancer target and provides that the suppression of NGLY1 in human cancer cells, in particular melanoma cells, can lead to specific anticancer responses, addressing an unmet medical need. In some aspects, the present disclosure provides methods of treating cancer comprising inhibiting NGLY1 in patient in need thereof. Also provided are inhibitors of NGLY1 including small molecule inhibitors of this protein.

In still some aspects, the present disclosure provides methods of treating a cancer in a patient comprising administering to the patient a therapeutically effective amount of an inhibitor of N-glycanase 1 (NGLY1). In some embodiments, the cancer is melanoma, ovarian cancer, breast cancer, cervical cancer, endometrial cancer, colon cancer, pancreatic cancer, prostate cancer, liver cancer, renal cancer, lung cancer, glioma, and lymphoma. In some embodiments, the cancer is glioma, liver cancer, or melanoma. The cancer may be melanoma. In other embodiments, the cancer is not multiple myeloma. The cancer may not be a hematologic cancer. In some embodiments, the cancer is associated with the dysregulation of NGLY1 such as upregulation of NGLY1. In some embodiments, the inhibitor of NGLY1 is a biological molecule. In some embodiments, the biological molecule is an shRNA such as an shRNA selected from:

```
                                      (SEQ ID NO: 1)
5' CCGAGUUUCAAAUAACAAUCAAUAGUGAAGCCA-CAGAUGUAUU

GAUUGUUAUUUGAAACUCGAU 3';
and
                                      (SEQ ID NO: 2)
5' AAAGCAUUACUUCGAGACACUAUAGUGAAGC-CACAGAUGUAUA

GUGUCUCGAAGUAAUGCUUCU 3'.
```

In other embodiments, the biological molecule is an antibody. In other embodiments, the biological molecule is a peptide or peptidomimetic. In other embodiments, the inhibitor of NGLY1 is a small molecule. In some embodiments, the small molecule is a compound or composition described herein. In some embodiments, the methods further comprise identifying a patient with a cancer which shows dysregulated expression of NGLY1. In some embodiments, the methods further comprise a second cancer therapy such as surgery, a second chemotherapeutic agent, a radiotherapy, or an immunotherapy. In some embodiments, the second cancer therapy is a second chemotherapeutic agent. The second chemotherapeutic agent may be an alkylating agent or an alkylating-like agent such as cisplatin, dacarbazine, or temozolomide. In other embodiments, the second chemotherapeutic agent is an agent which inhibits a protein. The second chemotherapeutic agent may be an agent which inhibits the proteasome such as bortezomib. Alternatively, the second chemotherapeutic agent may not be bortezomib or carfilzomib. The second chemotherapeutic agent may also not be an agent which inhibits the proteasome. In other embodiments, the second chemotherapeutic agent is an agent which inhibits BRAF or an agent which inhibits downstream signaling of MAPK such as vemurafenib. In another embodiment, the second cancer therapy is a radiotherapy such as X-ray therapy. In another embodiment, the second cancer therapy is an immunotherapy such as a PD-1 or PD-L1 inhibitor. In some embodiments, the patient is a mammal such as a human. In some embodiments, the methods comprise administering the compound once. In other embodiments, the methods comprise administering the compound two or more times.

In still yet another aspect, the present disclosure provides compounds of formula:

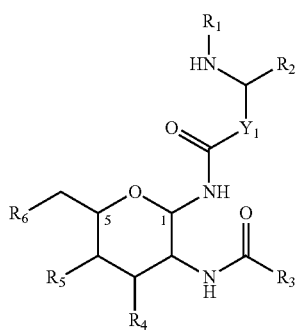

(I)

wherein:
R$_1$ is a thiol-reactive group;
R$_2$ is hydrogen, alkyl$_{(C\leq6)}$, substituted alkyl$_{(C\leq6)}$, or —CO$_2$NR$_7$R$_8$; wherein:
R$_7$ and R$_8$ are each independently hydrogen, alkyl$_{(C\leq6)}$, or substituted alkyl$_{(C\leq6)}$; or
R$_7$ and R$_8$ when taken together are heterocycloalkyl$_{(C\leq12)}$, heteroaryl$_{(C\leq12)}$, or a substituted version of any of these groups;
Y$_1$ is a covalent bond, alkanediyl$_{(C\leq6)}$, or substituted alkanediyl$_{(C\leq6)}$;
R$_3$ alkyl$_{(C\leq6)}$ or substituted alkyl$_{(C\leq6)}$;
R$_4$ and R$_5$ are each independently hydrogen, hydroxy, or —OC(O)R$_9$; wherein:
R$_9$ is hydrogen, alkyl$_{(C\leq6)}$ or substituted alkyl$_{(C\leq6)}$; and
R$_6$ is hydrogen, —OC(O)R$_{10}$, —NR$_{11}$C(O)R$_{10}$, —NR$_{11}$(CH$_2$)$_m$R$_{10}$, —NR$_{12}$R$_{13}$, or —O(CH$_2$)$_m$R$_{10}$; wherein:
m is 0, 1, or 2;
R$_{10}$ is alkyl$_{(C\leq6)}$, cycloalkyl$_{(C\leq6)}$, heterocycloalkyl$_{(C\leq8)}$, aryl$_{(C\leq12)}$, heteroaryl$_{(C\leq12)}$, or a substituted version of any of these groups;
R$_{11}$ is hydrogen, alkyl$_{(C\leq6)}$, or substituted alkyl$_{(C\leq6)}$;
R$_{12}$ and R$_{13}$ when taken together are heterocycloalkyl$_{(C\leq8)}$, heteroaryl$_{(C\leq12)}$, or a substituted version of any of these groups;
or a pharmaceutically acceptable salt thereof.

In some embodiments, the compounds are further defined as:

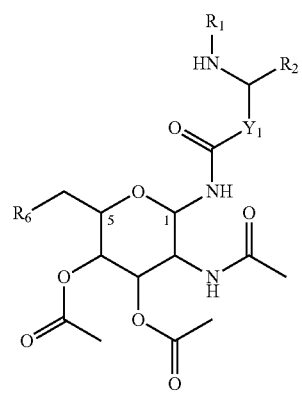

(II)

wherein:
R$_1$ is a thiol-reactive group;
R$_2$ is hydrogen, alkyl$_{(C\leq6)}$, substituted alkyl$_{(C\leq6)}$, or —CO$_2$NR$_7$R$_8$; wherein:
R$_7$ and R$_8$ are each independently hydrogen, alkyl$_{(C\leq6)}$, or substituted alkyl$_{(C\leq12)}$; or
R$_7$ and R$_8$ when taken together are heterocycloalkyl$_{(C\leq12)}$, heteroaryl$_{(C\leq12)}$, or a substituted version of any of these groups;
Y$_1$ is a covalent bond, alkanediyl$_{(C\leq6)}$, or substituted alkanediyl$_{(C\leq6)}$;
R$_6$ is hydrogen, —OC(O)R$_{10}$, —NR$_{11}$C(O)R$_{10}$, —NR$_{11}$(CH$_2$)$_m$R$_{10}$, —NR$_{12}$R$_{13}$, or —O(CH$_2$)$_m$R$_{10}$; wherein:
m is 0, 1, or 2;
R$_{10}$ is alkyl$_{(C\leq8)}$, cycloalkyl$_{(C\leq8)}$, heterocycloalkyl$_{(C\leq8)}$, aryl$_{(C\leq12)}$, heteroaryl$_{(C\leq8)}$, or a substituted version of any of these groups;
R$_{11}$ is hydrogen, alkyl$_{(C\leq6)}$, or substituted alkyl$_{(C\leq6)}$;
R$_{12}$ and R$_{13}$ when taken together are heterocycloalkyl$_{(C\leq8)}$, heteroaryl$_{(C\leq12)}$, or a substituted version of any of these groups;
or a pharmaceutically acceptable salt thereof.

In some embodiments, the compounds are further defined as:

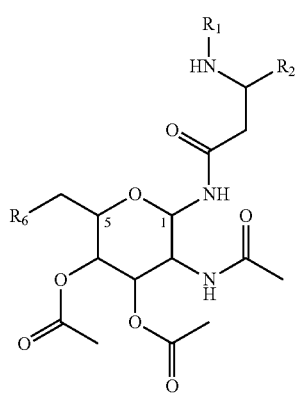

(III)

wherein:

$R_1$ is a thiol-reactive group;

$R_2$ is hydrogen, alkyl$_{(C\leq6)}$, substituted alkyl$_{(C\leq6)}$, or —CO$_2$NR$_7$R$_8$; wherein:

$R_7$ and $R_8$ are each independently hydrogen, alkyl$_{(C\leq6)}$, or substituted alkyl$_{(C\leq6)}$; or $R_7$ and $R_8$ when taken together are heterocycloalkyl$_{(C\leq12)}$, heteroaryl$_{(C\leq12)}$, or a substituted version of any of these groups;

$R_6$ is hydrogen, —OC(O)R$_{10}$, —NR$_{11}$C(O)R$_{10}$, —NR$_{11}$(CH$_2$)$_m$R$_{10}$, —NR$_{12}$R$_{13}$, or —O(CH$_2$)$_m$R$_{10}$; wherein:

m is 0, 1, or 2;

$R_{10}$ is alkyl$_{(C\leq6)}$, cycloalkyl$_{(C\leq8)}$, heterocycloalkyl$_{(C\leq8)}$, aryl$_{(C\leq12)}$, heteroaryl$_{(C\leq12)}$, or a substituted version of any of these groups;

$R_{11}$ is hydrogen, alkyl$_{(C\leq6)}$, or substituted alkyl$_{(C\leq6)}$;

$R_{12}$ and $R_{13}$ when taken together are heterocycloalkyl$_{(C\leq8)}$, heteroaryl$_{(C\leq12)}$, or a substituted version of any of these groups;

or a pharmaceutically acceptable salt thereof.

In some embodiments, $R_3$ is alkyl$_{(C\leq6)}$ or substituted alkyl$_{(C\leq8)}$ such as methyl. In some embodiments, $R_4$ or $R_5$ are each independently hydroxy or —OC(O)R$_9$; wherein: $R_9$ is hydrogen, alkyl$_{(C\leq6)}$ or substituted alkyl$_{(C\leq6)}$. In some embodiments, $R_4$ or $R_5$ are each independently —OC(O)R$_9$; wherein: $R_9$ is hydrogen, alkyl$_{(C\leq6)}$ or substituted alkyl$_{(C\leq6)}$. In some embodiments, $R_4$ or $R_5$ are —OC(O)CH$_3$. In some embodiments, $R_4$ and $R_5$ are —OC(O)CH$_3$.

In some embodiments, $Y_1$ is a covalent bond, alkanediyl$_{(C\leq6)}$, or substituted alkanediyl$_{(C\leq6)}$. In some embodiments, $Y_1$ is alkanediyl$_{(C\leq6)}$ such as —CH$_2$—. In other embodiments, $Y_1$ is substituted alkanediyl$_{(C\leq6)}$. In some embodiments, $R_6$ is hydrogen, —OC(O)R$_{10}$, —NR$_{11}$C(O)R$_{10}$, —NR$_{11}$(CH$_2$)$_m$R$_{10}$, —NR$_{12}$R$_{13}$, or —O(CH$_2$)$_m$R$_{10}$; wherein:

m is 0, 1, or 2;

$R_{10}$ is alkyl$_{(C\leq6)}$, cycloalkyl$_{(C\leq8)}$, heterocycloalkyl$_{(C\leq8)}$, aryl$_{(C\leq12)}$, heteroaryl$_{(C\leq12)}$, or a substituted version of any of these groups;

$R_{11}$ is hydrogen, alkyl$_{(C\leq6)}$, or substituted alkyl$_{(C\leq6)}$; and $R_{12}$ and $R_{13}$ when taken together are heterocycloalkyl$_{(C\leq8)}$, heteroary$_{(C\leq12)}$, or a substituted version of any of these groups.

In some embodiments, $R_6$ is —OC(O)R$_{10}$; wherein: $R_{10}$ is alkyl$_{(C\leq8)}$, cycloalkyl$_{(C\leq8)}$, heterocycloalkyl$_{(C\leq8)}$, aryl$_{(C\leq12)}$, heteroaryl$_{(C\leq12)}$, or a substituted version of any of these groups. In some embodiments, $R_6$ is —OC(O)R$_{10}$; wherein: $R_{10}$ is alkyl$_{(C\leq8)}$ or substituted alkyl$_{(C\leq8)}$. In some embodiments, $R_6$ is —OC(O)CH$_3$.

In some embodiments, $R_2$ is hydrogen, alkyl$_{(C\leq6)}$, substituted alkyl$_{(C\leq6)}$, or —CO$_2$NR$_7$R$_8$; wherein:

$R_7$ and $R_8$ are each independently hydrogen, alkyl$_{(C\leq6)}$, or substituted alkyl$_{(C\leq6)}$; or $R_7$ and $R_8$ when taken together are heterocycloalkyl$_{(C\leq12)}$, heteroaryl$_{(C\leq12)}$, or a substituted version of any of these groups.

In some embodiments, $R_2$ is alkyl$_{(C\leq6)}$ or substituted alkyl$_{(C\leq6)}$. In some embodiments, $R_2$ is substituted alkyl$_{(C\leq6)}$. In other embodiments, $R_2$ is alkyl$_{(C\leq6)}$ such as propyl.

In some embodiments, $R_1$ is heteroaryl$_{(C\leq8)}$ or substituted heteroaryl$_{(C\leq8)}$ such as 5-(3-methyl)-thiadiazolyl or 5-(3-methoxy)-thiadiazolyl. In other embodiments, $R_1$ is a group capable of undergoing a 1,4-addition reaction or a displacement reaction. In some embodiments, $R_1$ is a group capable of undergoing a displacement reaction. In some embodiments, $R_1$ comprises a halogen. In some embodiments, $R_1$ is further defined as:

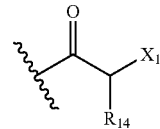

wherein:

$R_{14}$ is hydrogen, alkyl$_{(C\leq6)}$, or substituted alkyl$_{(C\leq6)}$; and $X_1$ is hydrogen or halo.

In some embodiments, $R_1$ is further defined as:

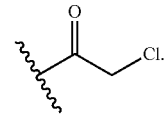 [SMILES: *C(=O)CCl]

In other embodiments, $R_1$ is a group capable of undergoing a 1,4-addition reaction. In some embodiments, $R_1$ is further defined as:

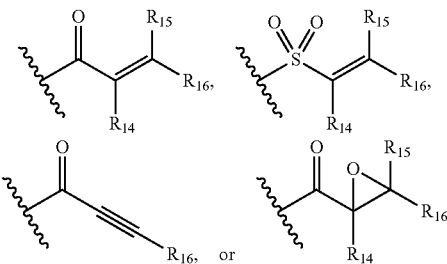

wherein:

$R_{14}$ is hydrogen, alkyl$_{(C\leq6)}$, or substituted alkyl$_{(C\leq6)}$; and $R_{15}$ and $R_{16}$ are each independently hydrogen, cyano, alkyl$_{(C\leq6)}$, substituted alkyl$_{(C\leq6)}$, —CO$_2$NR$_{17}$R$_{18}$, or —(CH$_2$)$_n$NR$_{17}$R$_{18}$; wherein:

$R_{17}$ and $R_{18}$ are each independently hydrogen, alkyl$_{(C\leq6)}$, substituted alkyl$_{(C\leq6)}$; or $R_{17}$ and $R_{18}$ when taken together are heterocycloalkyl$_{(C\leq12)}$, heterocycloalkyl$_{(C\leq8)}$, or a substituted version of any of these groups; and n is 1, 2, 3, or 4.

In some embodiments, $R_1$ is further defined as:

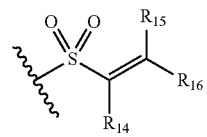

wherein:

R$_{14}$ is hydrogen, alkyl$_{(C≤6)}$, or substituted alkyl$_{(C≤6)}$; and

R$_{15}$ and R$_{16}$ are each independently hydrogen, cyano, alkyl$_{(C≤6)}$, substituted alkyl$_{(C≤6)}$, —CO$_2$NR$_{17}$R$_{18}$, or —CH$_2$NR$_{17}$R$_{18}$; wherein:

R$_{17}$ and R$_{18}$ are each independently hydrogen, alkyl$_{(C≤6)}$, substituted alkyl$_{(C≤6)}$; or R$_{17}$ and R$_{18}$ when taken together are heterocycloalkyl$_{(C≤12)}$, heterocycloalkyl$_{(C≤12)}$, or a substituted version of any of these groups.

In some embodiments, R$_1$ is further defined as:

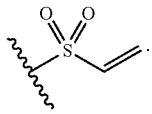 [SMILES: *S(=O)(=O)C=C]

In some embodiments, R$_1$ is further defined as:

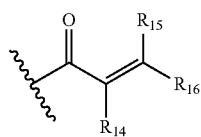

wherein:

R$_{14}$ is hydrogen, alkyl$_{(C≤6)}$, or substituted alkyl$_{(C≤6)}$; and

R$_{15}$ and R$_{16}$ are each independently hydrogen, cyano, alkyl$_{(C≤6)}$, substituted alkyl$_{(C≤6)}$, —CO$_2$NR$_{17}$R$_{18}$, or —CH$_2$NR$_{17}$R$_{18}$; wherein:

R$_{17}$ and R$_{18}$ are each independently hydrogen, alkyl$_{(C≤6)}$, substituted alkyl$_{(C≤6)}$; or R$_{17}$ and R$_{18}$ when taken together are heterocycloalkyl$_{(C≤12)}$, heterocycloalkyl$_{(C≤12)}$, or a substituted version of any of these groups.

In some embodiments, R$_1$ is further defined as:

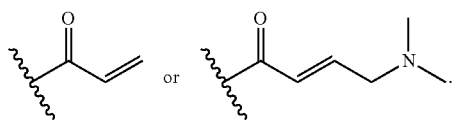

In some embodiments, carbon atom 1 is in the R configuration. In some embodiments, carbon atom 2 is in the R configuration. In some embodiments, carbon atom 3 is in the R configuration. In some embodiments, carbon atom 4 is in the S configuration. In some embodiments, carbon atom 5 is in the R configuration.

In some embodiments, the compounds are further defined as:

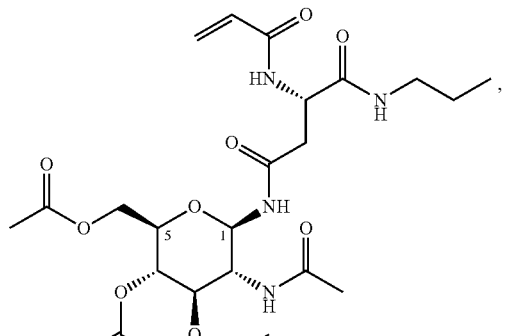,

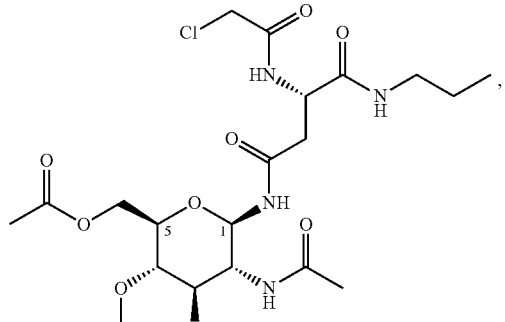,

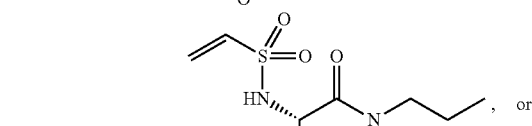, or

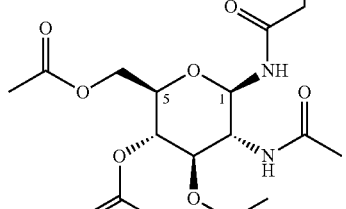

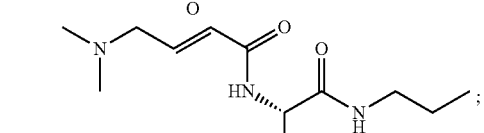;

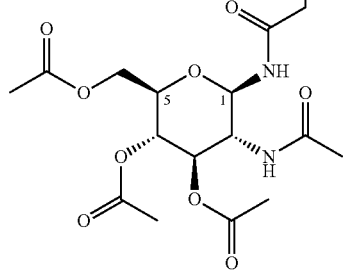

or a pharmaceutically acceptable salt thereof.

In still yet another aspect, the present disclosure provides pharmaceutical compositions comprising:

(A) a compound as described herein; and (B) an excipient.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In some embodiments, the pharmaceutical compositions are formulated as a unit dose.

In still another aspect, the present disclosure provides methods of treating a disease or disorder in a patient comprising administering to the patient in need thereof a therapeutically effective amount of a compound or composition described herein. In some embodiments, the disease or disorder is cancer. The cancer may be a carcinoma, sarcoma, lymphoma, leukemia, melanoma, mesothelioma, multiple myeloma, or seminoma or the cancer may be melanoma, ovarian cancer, breast cancer, cervical cancer, endometrial cancer, colon cancer, pancreatic cancer, prostate cancer, liver cancer, renal cancer, lung cancer, glioma, and lymphoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is glioma, liver cancer, or melanoma. The cancer may be melanoma. In other embodiments, the cancer is not multiple myeloma. The cancer may not be a hematologic cancer. In some embodiments, the methods further comprise a second cancer therapy such as surgery, a second chemotherapeutic agent, a radiotherapy, or an immunotherapy. In some embodiments, the second cancer therapy is a second chemotherapeutic agent. The second chemotherapeutic agent may be an alkylating agent or an alkylating-like agent such as cisplatin, dacarbazine, or temozolomide. In other embodiments, the second chemotherapeutic agent is an agent which inhibits a protein. The second chemotherapeutic agent may be an agent which inhibits the proteasome such as bortezomib. Alternatively, the second chemotherapeutic agent may not be bortezomib or carfilzomib. The second chemotherapeutic agent may also not be an agent which inhibits the proteasome. In other embodiments, the second chemotherapeutic agent is an agent which inhibits. BRAF or an agent which inhibits downstream signaling of MAPK such as vemurafenib. In another embodiment, the second cancer therapy is a radiotherapy such as X-ray therapy. In another embodiment, the second cancer therapy is an immunotherapy such as a PD-1 or PD-L1 inhibitor. In some embodiments, the disease or disorder is a viral infection. In some embodiments, the patient is a mammal such as a human. In some embodiments, the methods comprise administering the compound once. In other embodiments, the methods comprise administering the compound two or more times.

In still another aspect, the present disclosure provides methods of treating a viral infection in a patient comprising administering to the patient a therapeutically effective amount of an inhibitor of N-glycanase 1 (NGLY1).

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

(FIG. 1A) Protein expression in cultured cells. Blue shading: human normal melanocytes (HEMI) and induced pluripotent stem cells (HMi-506) in culture. Yellow shading: human melanoma cell lines. (FIG. 1B) The expression of the NGLY1 gene in cells at the transcriptional level was measured using qRT-PCR. First two columns: primary melanocytes (PM). Next five columns: human melanoma cell lines. Remaining columns: tumor samples of melanoma patients. asterisk: undetectable NGLY1 transcript in the sample. All data were presented as mean±standard deviation (n=3). The expression level of the ACTB gene in each sample was used as internal control for normalization. Gene expression levels in HEM1 cells were used as comparison standards to calculate relative expression values. (FIG. 1C) The upregulation of NGLY1 protein in patient tumor samples detected by an immunohistochemistry-staining method.

FIGS. 2A-2C shows the characterization of WA09 hESCs with the CRISPR/Cas9-mediated editing of the NGLY1 gene. (FIG. 2A) Similar cell morphology between NGLY1-C6 and NGLY1-C3 cells. (FIG. 2B) The expression of NGLY1 protein is lost in NGLY1-C3 and NGLY1-C4 cells. (FIG. 2C) NGLY1-C3 cells form EBs that contain cells in three germ-layer lineages. TUBB3: ectoderm, SMA: mesoderm, SOX17: endoderm.

(FIG. 3A) The positive staining of pluripotency markers in WA09-C6 (i.e. NGLY1-C6) and WA09-C3 (i.e. NGLY1-C3) hESCs. (FIG. 3B) NGLY1Pt1i-509 hiPSCs established from cell reprogramming in NGLY1-deficient patient-derived dermal fibroblasts. Upper panel: cell morphology. Lower panel: the expression NGLY1 and pluripotency markers NANOG and POU5F1 detected by Western blotting in the cells. (FIG. 3C) The positive staining of pluripotency markers in NGLY1Pt1i-509 hiPSCs.

FIGS. 4A-4B show cellular pluripotency tests and hESCs without NGLY1 expression and the formation of three-germ-layer cells in the EBs of hiPSCs of an NGLY-deficient individual. (FIG. 4A) The Pluritest results of undifferentiated WA09-C3 and WA09-C4 hESCs that are two independent NGLY1-knockout subclones revealed that their transcriptomic features are highly similar to the transcriptomic features of hPSC samples included in the Pluritest database. (FIG. 4B) NGLY1-deficient patient-derived hiPSCs formed EBs containing differentiated cells that are associated with three germ-layer lineages (TUBB3: ectoderm marker, Brachyury: mesoderm marker, and SOX17: endoderm marker).

(FIG. 5A) The doxycycline (dox)-inducible pZIP-TRE3GS expression vector of non-targeting shRNA and NGLY1-targeting shRNA sequences. (FIG. 5B) The stable clones of UACC257 cells with dox-inducible shRNA. Cells with induced NGLY1-shRNA645 (light cells) showed morphological features of apoptosis, including shrinkage and fragmentation. Cells with induced non-targeting (scramble)-shRNA maintain a morphology similar to the cells before dox induction. Cells were imaged after the treatment of 2 µM dox for 72 hours. BF: bright field. ZsGreen: green fluorescence protein. (FIG. 5C) ATF4 and GADD153 signaling was activated by the shRNA-mediated knockdown of NGLY1 in melanoma cells (FIG. 5D) Flow cytometry analysis reveals that NGLY1-targeting shRNA induced a significant increase of apoptosis in melanoma cells but not normal cells (HDF: human dermal fibroblasts, PM: primary melanocytes). (FIG. 5E) The expression of human NGLY1-FLAG in SK-MEL-2 (SK) cells attenuates NGLY1-targeting shRNA-induced apoptosis. EV: empty vector, NGLY1-F: NGLY1-FLAG expression vector. (FIG. 5F) The dose-dependent suppression of viability in MALME3M and SK-MEL-2 cells with the indicated dox-inducible shRNA in response to cisplatin, dacarbazine, vemurafenib and dox treatment. All data were presented as mean±standard deviation (n=3, *P<0.05, logistic regression). (FIG. 5G) The synergistic anticancer responses of NGLY1 knockdown and dacarbazine treatment for 72 hours in MALME3M and SK-MEL-2 cells. The cell viability curves of combinatorial treatment were plotted according to the doses of dox used in the treatment. Combination indexes were calculated using Calcusyn software. A combination index value <1 was considered synergistic. A combination index value <0.2 was considered highly synergistic. All cell viability data were presented as mean±standard deviation (n=3).

FIGS. 7A-7D show melanoma cells with the shRNA-mediated suppression of NGLY1 presented characteristic alterations in proteomics analysis. NGLY1 knockdown induced the increase of peptides containing GleNAc-asparagine residues and additional perturbation in the proteomes of MALME3M and SK-MEL-2 cells with inducible shRNA targeting NGLY1. (FIG. 7A) Schematic illustration of enhanced ENGase-mediated formation of peptides containing GlcNAc-asparagine residues in the absence of NGLY1 in cells. (FIG. 7B) The MS/MS spectrum of tryptic peptide ions containing GlcNAc-asparagine residues annotated as N(HexNAc) of TTLL1, IL-37, SHROOM2, KCNB2 identified in the protein samples of MALME3M and SK-MEL2 cells with NGLY1 knockdown. (FIG. 7C) The mass spec information of representative GlcNAc-modified peptides. (FIG. 7D) The proportion of peptides containing GlcNAc-asparagine residues in the proteome of each cell sample was analyzed. The results of 3 biological replicates for each experimental setting were plotted. Prior to sample collection for analysis, 1 µM doxycycline (dox) was used to treat cells for the indicated periods.

(FIG. 8A) The shRNA-mediated suppression of NGLY knockdown-induced GADD153 (DDIT3) in SK-MEL-2 cells. SK-MEL-2 cells with inducible NGLY1-shRNA645 were transduced with GADD153-targeting shRNA and subsequently treated with 2 µM dox for 48 hours to induce the expression of NGLY1-targeting shRNA. Three independent shRNA sequences that target GADD153: shRNA301, shRNA303 and shRNA304. (FIG. 8B) The shRNA-mediated suppression of GADD153 attenuated NGLY1 knockdown-induced apoptosis in SK-MEL-2 cells. Upper left panel: The GFP/RFP-double positive cells indicated NGLY1-knockdown/control and NGLY1-knockdown/GADD153-knockdown cells. Lower left panel: The analysis of apoptotic (annexin V-stained) cells in the GFP/RFP-double positive cells. Right panel: The quantitative results of flow cytometry analysis in the cells with 72-hour induction of NGLY1-targeting shRNA. All the quantitative data were presented as mean±standard deviation (n=3) in the bar graphs (*P<0.05, t-test).

FIGS. 10A-10F show differential gene expression caused by NGLY1 suppression in melanoma cells, hESCs and the differentiated derivatives of hESCs. SK-MEL-2, COLO829, UACC257 and MALME3M melanoma cells with the expression of the indicated inducible shRNA due to the treatment of 2 µM dox for 48 hours were collected for RNA isolation and global gene expression profiling. WA09, WA09-C6, WA09-C3, WA09-C4 hESCs and their differentiated derivatives were also collected for analysis. Samples of two biological replicates for each setting were analyzed. (FIG. 10A) A heat map representation of ~750 probes that measured the relative expression levels of differentially expressed genes (P<0.01, t-test between control and knockdown cells) in melanoma cell samples expressing the indicated shRNA. Red dots: melanoma cells with NGLY1 knockdown. Green dots: control cells. (FIG. 10B) Selected genes that were differentially expressed (P<0.01 and fold change ≥22) in the control and NGLY1-knockdown melanoma cells were annotated in a volcano plot of fold change vs. significance. (FIG. 10C) The qRT-PCR validation of selected genes that were differentially expressed in the control and NGLY1-knockdown melanoma cells (n=3, *P<0.05, t-test). The expression level of the ACTB gene in each sample was used as internal control for normalization. Gene expression levels in SK-MEL-2 cells with NT-shRNA were used as comparison standards to calculate relative expression values. (FIG. 10D) Gene ontology analysis revealed that genes differentially expressed (P<0.01 and fold change ≥2) due to NGLY1 suppression in melanoma cells were highly enriched in biological processes including response to stimulus, metabolic process, and cellular process. (FIG. 10E) A volcano plot of fold change vs. significance for selected genes that were differentially expressed (P<0.01 and fold change ≥2) in control and NGLY1-deficient WA09 hESCs. (FIG. 10F) A volcano plot of fold change vs. significance for selected genes that were differentially expressed (P<0.01 and fold change ≥2) in the embryoid bodies of control and NGLY1-deficient WA09 hESCs gone through 6 days of non-directed differentiation.

(FIG. 11A) The contents of IFNβ1 and IL-29 in the conditional media of UACC257 and SK-MEL-2 cell clones with the indicated treatment were measured by cytokine profiling. (FIG. 11B) The NGLY1 knockdown-induced upregulation of IFNβ1 and IL-29 was significantly attenuated by the overexpression of exogenous human NGLY1 in the cells. (FIG. 11C) Left panel: the attenuation of NGLY1 knockdown-induced viability reduction by the treatment of specific IFNβ1 neutralization antibody in the cells. Right panel: the attenuation of NGLY1 knockdown-induced viability reduction by the treatment of specific IL-29 neutralization antibody in the cells. NGLY knockdown was induced by the treatment of 2 µM dox for 72 hours in the cells. (FIG. 11D) The enhanced expression and activation of IRF3, IRF7 and their upstream kinase TBK1 was detected in SK-MEL-2 and MALME3M cells with NGLY1 knockdown. The serine phosphorylation of IRF3 and TBK1 indicates their activity. NT non-targeting shRNA. 645: NGLY1-targeting shRNA645. All data were presented as mean±standard deviation (n=3; *P<0.05, t-test).

(FIG. 14A) A schematic illustration of animal study design to test the in vivo antitumor efficacy of NGLY1 suppression in melanoma. (FIG. 14B) The volume changes of xenograted SK-MEL-2 tumors with the induction of NT-shRNA (n=10) and NGLY1-shRNA645 (n=8) for 35 days. Tumors were harvested at the end of the study for Western blotting analysis. Bars: median tumor volumes at the indicated time points. Inset: the volume changes of three tumors with NGLY1-targeting shRNA that initially increased their size but showed regression at the end of the study. (FIG. 14C) The expression of NGLY1, GADD153, IRF3, and GFP (Zs-Green) proteins in selected tumors was analyzed by Western blotting. (FIG. 14D) The enhanced expression of IL-29 in the tumor tissues with NGLY1 knockdown was detected by immunofluorescence staining.

(FIG. 15A) The most favorable binding pose of Z-VAD-fmk, a short peptide with NGLY1 and caspase inhibitory activity, in the human NGLY1 homology model superimposed to the conformation of Z-VAD-fmk bound to mouse NGLY1 in a co-crystalized structure. (FIG. 15B) Novel small molecules (NM-322, NM-348, NM-350, and NM-354) that mimic a GlcNAc-conjugated asparagine in the NGLY1 substrates of NGLY1 and contain strategically positioned electrophilic groups bound to the human NGLY1 homology model in computational docking and showed their high binding affinities with the electrophilic groups pointed towards Cys309 in close proximity at the human NGLY1 catalytic site. (FIG. 15C) Upper panel: The 2-hour reaction of covalent modifiers, including Z-VAD-fmk (20 µM), WRR139 (5 µM), NM-322, NM-348, NM-350 and NM-354, with human NGLY1 suppressed its activity in the deglycosylation of denatured RNase B. Blue arrowhead: recombinant NGLY1-FLAG. RNase B (g): glycosylated RNase B. RNase B (dg): deglycosylated RNase B. Veh: vehicle (DMSO) treatment. M: molecular weight marker. Lower panel: the deglycosylation of NFE2L1 altered by the treatment of 20 µM Z-VAD-fmk and 200 µM NM-350 in bortezomib-treated HEK293T cells. The cells were pretreated with vehicle (DMSO), Z-VAD-fmk and NM-350 for 24 hours and subsequently subjected to concomitant treatment with 10 µM bortezomib for an additional 16 hours. Cell lysates reacted with and without 500 units of PNGase F for 2 hours were analyzed using Western blotting. Top arrowhead in lanes 2 and 3: fully glycosylated NFE2L1. Top arrowhead in lane 1: partially glycosylated NFE2L1. Bottom arrowhead: deglycosylated and truncated NFE2L1. (FIG. 15D) The dose-dependent suppression of cell viability was preferentially induced by the novel NGLY1 inhibitors in melanoma cells compared with normal cells (*P<0.05, logistic regression). (FIG. 15E) The synergistic effect was observed between NM-322 and dacarbazine in the suppression of melanoma cell viability. The cell viability curve of combinatorial treatment was plotted according to the doses of dacarbazine used in the treatment. (FIG. 15F) The synergistic effect was observed between NM-350 and bortezomib in the suppression of melanoma cell viability. The cell viability curve of combinatorial treatment was plotted according to the doses of bortezomib used in the treatment. All the data of cell viability tests were presented as mean±standard deviation (n=3).

(FIG. 16A) The production of IFNβ1 and IL-29 was enhanced by novel small-molecule inhibitors targeting NGLY1. HDF51, UACC257, and SK-MEL-2 cells were treated using the indicated inhibitors. The conditional media of the cells were collected for cytokine analysis at the end of 48-hour drug treatment. The concentration of each inhibitor used in the test was 200 µM. The data of cytokine analysis were presented as mean±standard deviation (n=3, *P<0.05, t-test; ud., undetectable). (FIG. 16B) The proportion of peptides containing GlcNAc-asparagine residues in the proteome of each cell sample was analyzed. The results of 3 biological replicates for each experimental setting were plotted. Prior to sample collection for analysis, 1 µM doxycycline (dox), 200 µM NM-348 or 200 µM NM-350 was used to treat cells for the indicated periods.

(FIG. 17B) U-251MG glioblastoma cells showed a morphology of apoptosis (cell death) in response to the knockdown of NGLY1 (NT-shRNA: non-targeting shRNA; shRNA645 and shRNA647: two NGLY1-targeting shRNA sequences).

DESCRIPTION OF ILLUSTRATIVE EMBODIMENTS

Figure 1A:
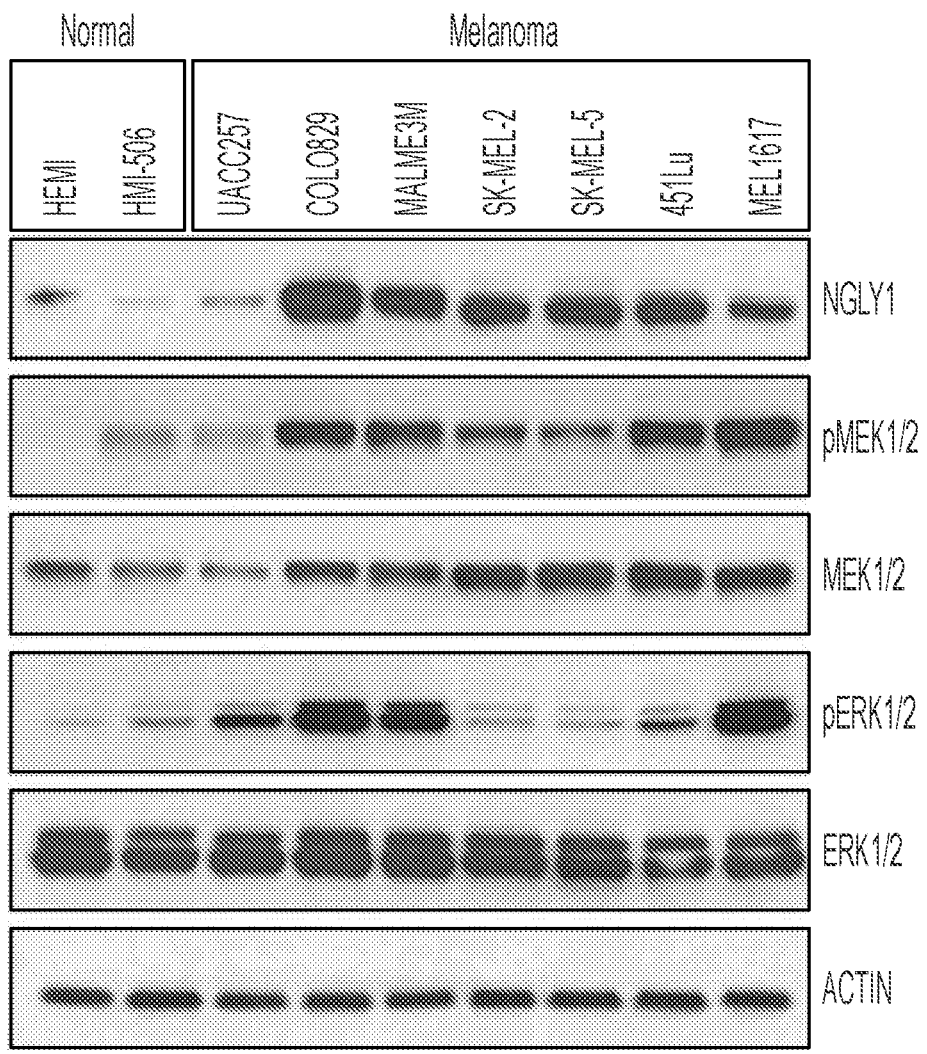
FIGS. 1A-1C shows the expression of NGLY1 in human normal and melanoma cells.

The present disclosure provides derivatives of GlcNAc-Asn which may be used to treat or prevent a disease or disorder such as cancer. In some aspects, these compounds inhibit NGLY1. In some aspects, these compounds may contain modifications which increase the activity, chemical stability, or both. Also, provided herein are methods of using these compounds and pharmaceutical compositions thereof.

I. COMPOUNDS AND FORMULATIONS THEREOF

A. Compounds

The compounds provided by the present disclosure are shown, for example, above in the summary section and in the examples and claims below. They may be made using the methods outlined in the Examples section. The GlcNAc-Asn analogs described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The GlcNAc-Asn analogs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the GlcNAc-Asn analogs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The GlcNAc-Asn analogs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the GlcNAc-Asn analogs described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The GlcNAc-Asn analogs described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the GlcNAc-Asn analogs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the GlcNAc-Asn analogs described herein are within the scope of the disclosure. It will also be appreciated by those skilled in organic chemistry that many organic compounds can exist in more than one crystalline form. For example, crystalline form may vary from solvate to solvate. Thus, all crystalline forms of the GlcNAc-Asn analogs described herein are within the scope of the present disclosure.

B. Formulations

In some embodiments of the present disclosure, the GlcNAc-Asn analogs are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the GlcNAc-Asn analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropyl-cellulose, carboxymethylcellulose, acrylate copolymers, polyethylene glycols and/or polyvinyl-pyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND NGLY1

A. Protein Quality Control and Homeostasis in Health and Disease.

Proteostasis (also known as protein homeostasis) is a fundamental and tightly regulated process in all eukaryotic cells. In addition to its critical role in protein quality control that allows cells to manage denatured proteins and maintain the integrity of proteome (Chen et al., 2011a), proteostasis also mediates the fine-tuning of cell signaling activity (Wang et al., 2014). In general, proteostasis is achieved through an intricate balance between the synthesis and degradation of proteins. The interruption of proteostasis in normal cells could be associated with detrimental outcomes or pathogenesis (Toyana and Hetzer, 2013). Interestingly, using proteasome inhibitors (e.g., bortezomib and carfilzomib) to target protein quality control and homeostasis appears to be a useful approach to eliminate cancer cells (Kuhn et al., 2007; Orlowski and Kuhn 2008). The use of proteasome inhibitors as anticancer agents suggests that the proteasome-mediated protein degradation, a well-known molecular component involved in proteostasis, is highly demanded by cancer cells to sustain their viability or oncogenic signaling.

B. Glycosidase NGLY1.

As a pivotal enzyme known for catalyzing the removal of saccharide moieties from N-glycosylated asparagine residues, NGLY1 (also known as N-glycanase 1 and PNGase) enables the deglycosylation of denatured glycoproteins and allows proteasome-mediated protein degradation to efficiently occur (Huang et al., 2015; Caglayan et al., 2015; Enns et al., 2014; Need et al., 2012; Suzuki 2015). Human NGLY1 protein consists of three major domains that include the PAW (mannose-binding), TGase-superfamily (PNGase-core), and PUB domains. The TGase-superfamily domain exists in NGLY1 proteins that are expressed in the species ranging from yeast to human (Suzuki 2015), suggesting the evolutionarily conserved significance of NGLY1 enzymatic activity in cells. It is known that loss of NGLY1 function in cells can cause the accumulation of aberrant proteins in the cytosol and the interruption of endoplasmic reticulum-associated protein degradation (ERAD) (Huang et al., 2015; Enns et al., 2014; Suzuki 2015).

Therefore, NGLY1 defects are likely to affect the quality control and homeostasis of many cellular proteins, subsequently perturbing cell signaling pathways, cell physiology, and organ development. The studies of an NGLY1 ortholog gene, PNGase-like (Pngl), in *D. melanogaster* (fruit fly) and *N. crassa* (fungus) also indicate that NGLY1 could be involved in the regulation of cell normality through an enzymatic activity-independent mechanism (Funakoshi et al., 2010; Maerz et al., 2010). It is known that benzyloxycarbonyl-Val-Ala-Asp (Z-VAD) can occupy the catalytic pocket and inactivate the enzymatic activity of NGLY1. However, Z-VAD also affects the activity of other proteases (e.g., caspase 3) that are critical for many other cell signaling pathways. Currently, molecules specifically suppressing NGLY1 activity are unavailable, presenting a major challenge in dissecting the enzymatic activity-dependent and -independent mechanisms underlying abnormalities in different cells with NGLY1 defects.

C. NGLY1 Expression and Deficiency in Human Cells.

According to the Human Protein Atlas (www.proteinatlas.org/ENSG00000151092-NGLY1/tissue; www.proteinatlas.org/ENSG00000151092-NGLY1/cancer), NGLY1 protein is commonly expressed in many types of normal and cancer cells. These data suggest that NGLY1 could be essential for a variety of human cells regardless of their pathophysiological conditions. However, the mutations of human NGLY1 gene that result in NGLY deficiency have been recently identified as the cause of a previously undiagnosed congenital disorder of deglycosylation (Caglayan et al., 2015; Enns et al., 2014; Heeley & Shinawi, 2015). Many of these mutations cause premature termination of NGLY1 protein translation, leading to complete loss of NGLY1 in the patients. Despite the developmental abnormalities found in NGLY1-deficient patients (Lam et al. 2016), the existence of NGLY1-deficient patients attests to the tolerability of NGLY1 malfunction in vital organs and the viability of somatic cells without NGLY1 function. In addition, NGLY1 protein appears to be highly expressed in certain human cancer cells (e.g., melanoma and ovarian cancer), while low-to-undetectable in their normal counterpart tissue (e.g., skin and ovary) (www.proteinatlas.org/ENSG00000151092-NGLY1/tissue; www.proteinatlas.org/ENSG00000151092-NGLY1/cancer). These observations raise an interesting possibility that NGLY1 may be crucial for cancer development and progression. Moreover, cancer cells may be particularly vulnerable to loss of NGLY1 compared with normal cells. Targeting NGLY1 and protein deglycosylation therefore represent a new anticancer approach with an useful therapeutic window. The initial data described herein revealed that NGLY1 knockdown induces massive cell death in several lines of human melanoma cells, while human melanocytes, keratinocytes, cutaneous fibroblasts and pluripotent stem cells (hPSCs) appear virtually unaffected by the suppression or complete loss of NGLY1.

D. Cancer

While hyperproliferative diseases can be associated with any disease which causes a cell to begin to reproduce uncontrollably, the prototypical example is cancer. One of the key elements of cancer is that the cell's normal cell cycle is dysregulated and thus agents that interrupt the growth and viability of the cancer cells are important as therapeutic agents for treating these diseases. In this disclosure, the GlcNAc-Asn analogs described herein may be used to inhibit a specific protein associated with cell proliferation or other biological processes essential for the viability of cancer cells, specifically the NGLY1 enzyme. In some aspects, it is anticipated that the GlcNAc-Asn analogs described herein may be used to treat any malignancy wherein abhorrent regulation of NGLY1 is present.

Cancer cells that may be treated with the compounds of the present disclosure include but are not limited to cancer types associated with the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignancy; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the GlcNAc-Asn analogs of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the GlcNAc-Asn analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate regulatory agencies for the safety of pharmaceutical agents.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the GlcNAc-Asn analogs used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the GlcNAc-Asn analogs may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the GlcNAc-Asn analogs described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the GlcNAc-Asn analogs described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are also contemplated. The following is a general discussion of cancer therapies that may be used in combination with the compounds or compositions of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell growth and viability. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma_1$ and calicheamicin co; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ERBB2 would provide therapeutic benefit in the treatment of ERBB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, ERBB and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski, et al., 1998; Davidson, et al., 1998; Hellstrand, et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras, et al., 1998; Hanibuchi, et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton, et al., 1992; Mitchell, et al., 1990; Mitchell, et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg, et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1p, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate pharmaceutical agent regulatory agencies.

It also should be pointed out that any of the foregoing therapies may prove useful by themselves in treating cancer.

IV. SYNTHETIC METHODS

In some aspects, the GlcNAc-Asn analogs of this disclosure can be synthesized using the methods of organic chemistry as described in this application. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

A. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; "hydrazine" means —NHNH$_2$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO$_3$H, "sulfonyl" means —S(O)$_2$—; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol "⌇" represents a single bond or a double bond. Thus, the formula

covers, for example,

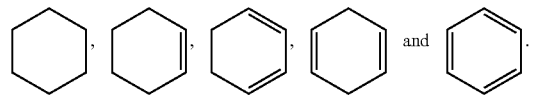

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⦀⦀⦀" means a single bond where the group attached to the thick end of the wedge is "into the page". The symbol "∿" means a single bond where the geometry around a double bond [e.g., either (E) or (Z)] is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

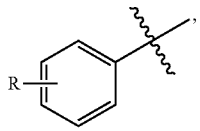

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

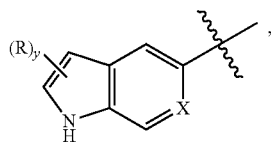

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$," or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$(i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$(isobutyl), —C(CH$_3$)$_3$ (tert-butyl, t-butyl, t-Bu or $^t$Bu), and —CH$_2$C(CH$_3$)$_3$(neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e., —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$(cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

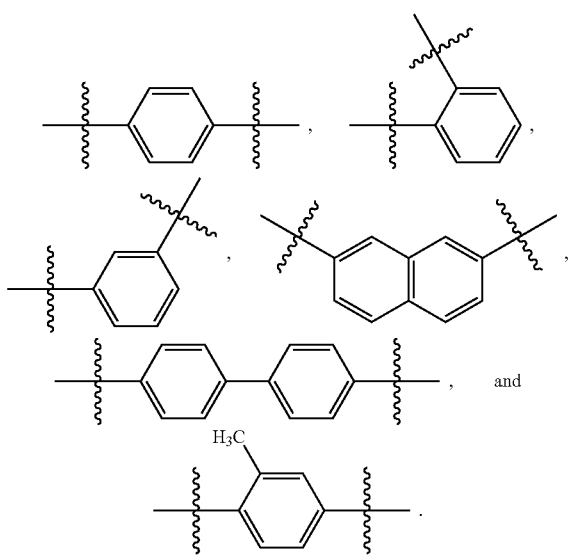

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, the aromatic ring structures being one, two, three, or four ring structures each containing from three to nine ring atoms, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, the non-aromatic ring structures being one, two, three, or four ring structures each containing from three to nine ring atoms, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)

CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$(isopropoxy), or —OC(CH$_3$)$_3$(tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via a nitrogen atom.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, an amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$—, wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxy-benzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyl-oxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethyl-silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}NH-$ or $PG_{DA}N-$ wherein $PG_{MA}$ is a monovalent amine protecting group, which may also be described as a "monvalently protected amino group" and $PG_{DA}$ is a divalent amine protecting group as described above, which may also be described as a "divalently protected amino group".

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyl-oxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methyl-ethoxycarbonyl, α,α-dimethyl-3,5-dimethoxybenzyloxycarbonyl, benzhydryloxycarbonyl, t-butyloxy-carbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyl-oxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula $PG_HO-$ wherein $PG_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyl-oxycarbonyl, p-bromobenzyloxycarbonyl, 3,4-dimethoxybenzyloxycarbonyl, 3,5-dimethoxy-benzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxy-carbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxy-carbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula $PG_TS-$ wherein $PG_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedrally substituted carbon centers), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its (R) form, (S) form, or as a mixture of the (R) and (S) forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

As a pivotal enzyme known for catalyzing the removal of saccharide moieties from N-glycosylated asparagine residues, NGLY1 (also known as N-glycanase 1 and PNGase) enables the deglycosylation of denatured glycoproteins and allows proteasome-mediated protein degradation to efficiently occur (Huang et al., 2015; Caglayan et al., 2015; Enns et al., 2014; Need et al., 2012; Suzuki 2015). Human NGLY1 protein consists of three major domains that include the PAW (mannose-binding), TGase-superfamily (PNGase-core), and PUB domains. The TGase-superfamily domain exists in NGLY1 proteins that are expressed in the species ranging from yeast to human (Suzuki 2015), suggesting the evolutionarily conserved significance of NGLY1 enzymatic activity in cells. It is known that loss of NGLY1 function in cells can cause the accumulation of aberrant proteins in the cytosol and the interruption of endoplasmic reticulum-associated protein degradation (ERAD) (Huang et al., 2015; Enns et al., 2014; Suzuki 2015). Therefore, NGLY1 defects are likely to affect the quality control and homeostasis of many cellular proteins, subsequently perturbing cell signaling pathways, cell physiology, and organ development. The studies of an NGLY1 ortholog gene, PNGase-like (Pngl), in *D. melanogaster* (fruit fly) and *N. crassa* (fungus) also indicate that NGLY1 could be involved in the regulation of cell normality through an enzymatic activity-independent mechanism (Funakoshi et al., 2010; Maerz et al., 2010). It is known that benzyloxycarbonyl-Val-Ala-Asp (Z-VAD) can occupy the catalytic pocket and inactivate the enzymatic activity of NGLY1. However, Z-VAD also affects the activity of other proteases (e.g., caspase 3) that are critical for many other cell signaling pathways. At present, optimized small molecules specifically suppressing NGLY1 activity are unavailable, presenting a major challenge in dissecting the enzymatic activity-dependent and -independent mechanisms underlying abnormalities in different cells with NGLY1 defects.

According to the Human Protein Atlas (www.proteinatlas.org/ENSG00000151092-NGLY1/tissue; http://www.proteinatlas.org/ENSG00000151092-NGLY1/cancer), NGLY1 protein is commonly expressed in many types of normal and cancer cells. These data suggest that NGLY1 could be essential for a variety of human cells regardless of their pathophysiological conditions. However, the mutations of human NGLY1 gene that result in NGLY deficiency have been recently identified as the cause of a previously undiagnosed congenital disorder of deglycosylation (Caglayan et al., 2015; Enns et al., 2014; Heeley & Shinawi, 2015). Many of these mutations cause premature termination of NGLY1 protein translation, leading to complete loss of NGLY1 in the patients. Despite the developmental abnormalities found in NGLY1-deficient patients (Lam et al. 2016), the existence of NGLY1-deficient patients attests to the tolerability of NGLY1 malfunction in vital organs and the viability of somatic cells without NGLY1 function. In addition, NGLY1 protein appears to be highly expressed in certain human cancer cells (e.g., melanoma and ovarian cancer), while low-to-undetectable in their normal counterpart tissue (e.g., skin and ovary) (http://www.proteinatlas.org/ENSG00000151092-NGLY1/tissue; http://www.proteinatlas.org/ENSG00000151092-NGLY1/cancer). These observations raise an interesting possibility that NGLY1 may be crucial for cancer development and progression. Moreover, cancer cells may be particularly vulnerable to loss of NGLY1 compared with normal cells. Targeting NGLY1 and protein deglycosylation therefore represent an alternative anticancer approach possibly with an excellent therapeutic window. In support of this possibility, preliminary data disclosed herein revealed that NGLY1 knockdown induces massive cell death in several lines of human melanoma cells, while human melanocytes, keratinocytes, cutaneous fibroblasts and pluripotent stem cells (hPSCs) appear virtually unaffected by the suppression or complete loss of NGLY1.

From studying a recently identified genetic disorder known as NGLY1 deficiency, it was realized that critical organs composed of many cell types can maintain their necessary functions for the vitality of an individual who has complete loss of NGLY1 (Lam et al. 2016; Enns et al., 2016). Although many types of cells present abnormal features in NGLY1-deficient patients, these abnormalities may be attributed to abnormal embryonic development rather than the direct effects of NGLY1 loss on terminally differentiated somatic cells. Thus, the impact of temporary suppression of NGLY1 on somatic cells within a standard treatment period for adult cancer patients could be quite mild. Similar to certain anticancer targets (e.g., proteasome and histone deacetylases) where their inhibition appears to be well tolerated in normal cells (Almond & Cohen, 2002; Marks 2010), NGLY1 may represent a unique target for designing novel anticancer approaches with marginal side effects.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—NGLY1 Expression in Human Normal and Cancer Cells

Figure 1B:
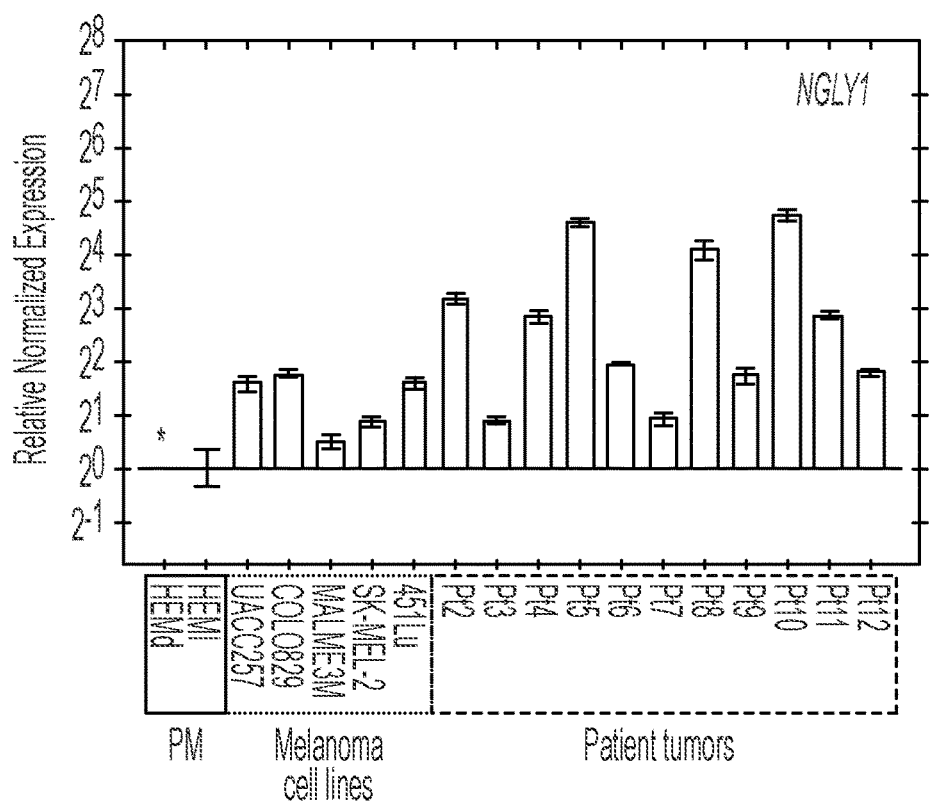
Figure 1C:
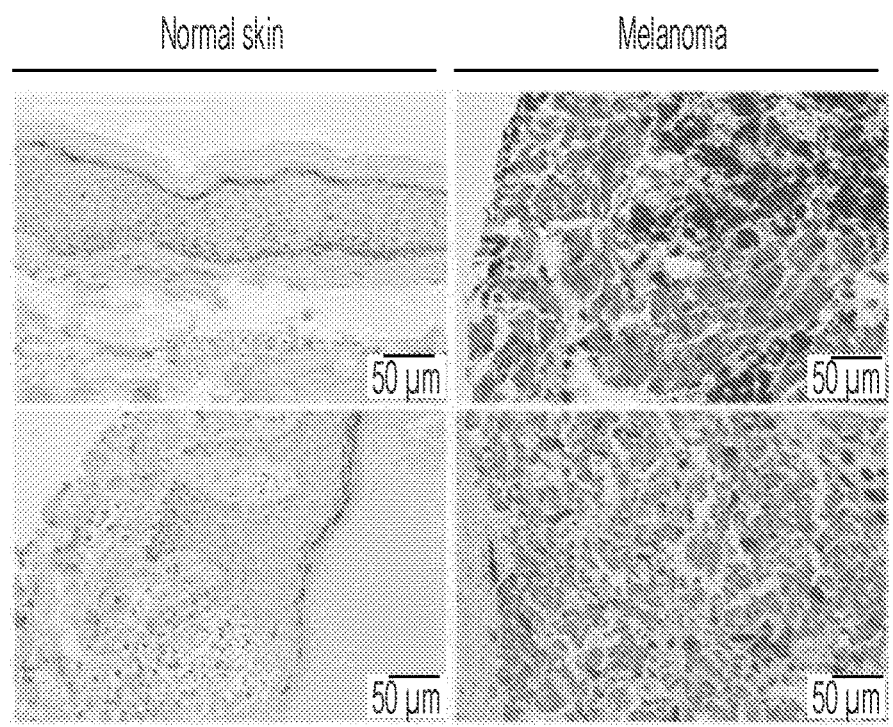
Figure 3A:
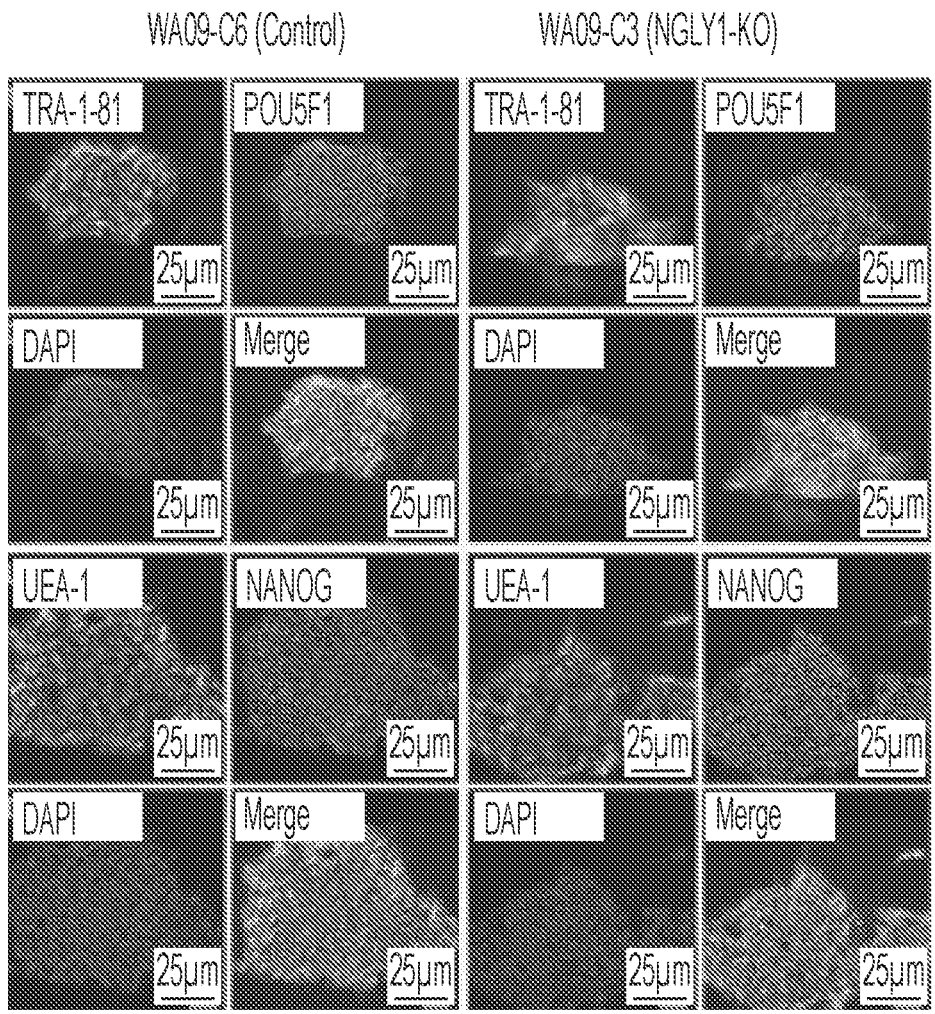
FIGS. 3A-3C shows the normal expression of cellular pluripotency markers in human pluripotent stem cells (hPSCs) with and without the loss of NGLY1.

The expression of the NGLY1 gene in human normal and melanoma cells was analyzed. Compared with human normal cells (e.g., human normal melanocytes) in culture, a vast majority of the melanoma cell lines show the clear upregulation of NGLY1 (FIGS. 1A and 1B). The upregulation of NGLY1 is also observed in tumor samples of melanoma patients (FIGS. 1B and 1C; Table 1). These findings are consistent with the data from the Human Protein Atlas (www.proteinatlas.org/ENSG00000151092-NGLY1/tissue; www.proteinatlas.org/ENSG00000151092-NGLY1/cancer), supporting the potential importance of NGLY1 in melanoma cells. As a type of human pluripotent stem cells (hPSCs), undifferentiated human embryonic stem cells (hESCs) are capable of differentiation into virtually all types of somatic cells relevant to three embryonic germ layers (ectoderm, mesoderm and endoderm) and share certain characteristics (e.g., high proliferation with a fast progressing cell cycle) with cancer cells. While similar to cancer cells in some features, hESCs are distinct from cancer cells and considered as human normal cells in a unique cellular state (Wang et al., 2014). In a separate project, multiple clones of NGLY1-deficient WA09 hESCs (FIG. 2) were obtained using the CRISPR/Cas9 mediated gene editing. Compared with the parental cells (hESCs with wild-type NGLY1) or a cell clone, NGLY1-C6 (i.e. WA09-C6), that went through the gene editing process but retained NGLY1 expression, the NGLY1-deficient hESC clones, NGLY1-C3 and NGLY1-C4 (i.e. WA09-C6 and WA09-C4), show the typical morphology of undifferentiated hPSCs and the similar expression of pluripotency factors (e.g., POU5F1). They also maintain the cellular pluripotency, evidenced by their ability to form embryoid bodies (EBs) containing differentiated progenitor cells for three germ-layer lineages. In addition, no obvious defects in the expression of cellular pluripotency markers are found in the NGLY1-deficient hESCs (FIG. 3A). The molecular features revealed by global gene expression profiling indicate that NGLY1-deficient hESCs are highly similar to other normal hPSCs (FIG. 4A). Although the NGLY1-deficient hESCs may present certain abnormalities during the development of specific cell lineages at a later time point, the data clearly suggest that NGLY1 deficiency can be well tolerated by normal human cells than in a highly sensitive state like the embryonic stage.

Figures 3B, 3C:
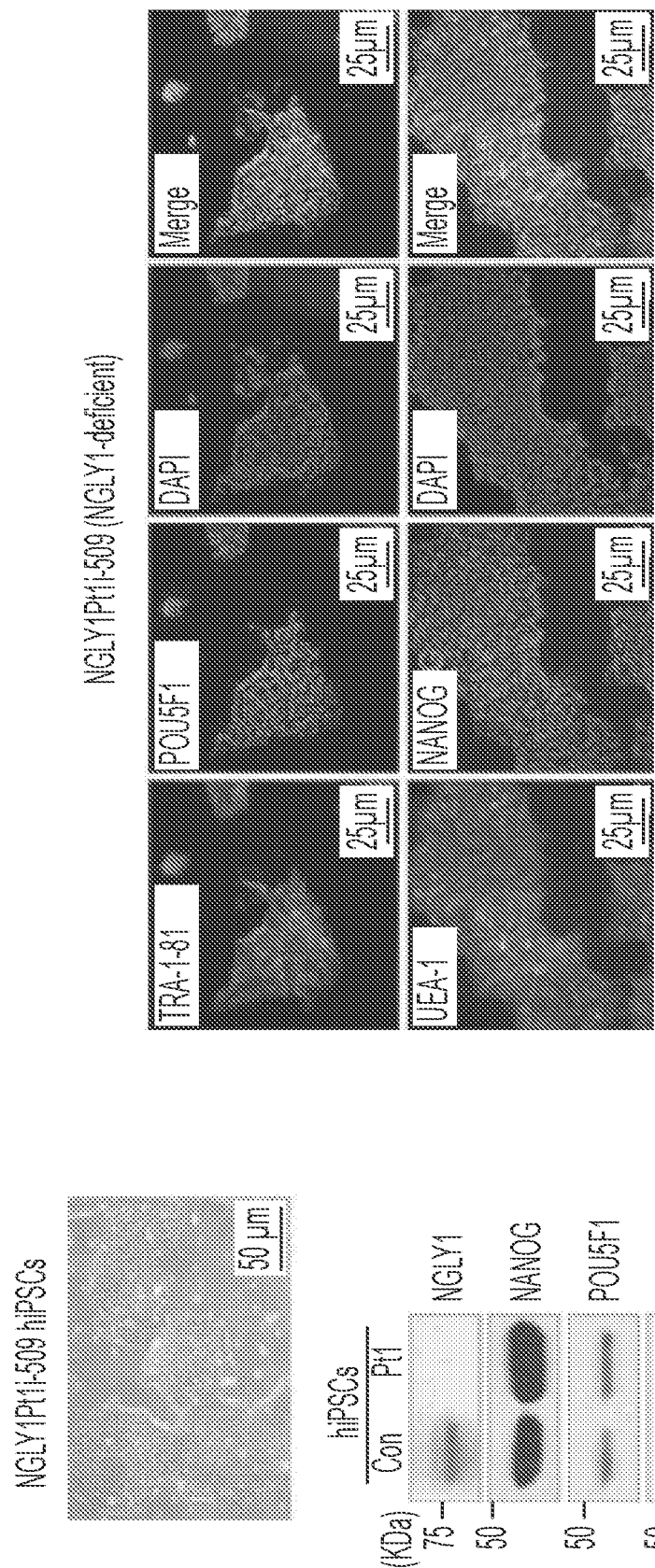

The NGLY1-deficient patient's dermal fibroblasts can be reprogrammed into human induced pluripotent stem cells (hiPSCs) (FIG. 3B). Like the NGLY1-deficient hESCs, the patient-derived hiPSCs without NGLY1 expression can be continuously cultured and maintain typical hPSC morphology, Molecular features and the capacity of forming embryoid bodies (EBs) containing differentiated cells that are associated with three germ layers (FIG. 3C; FIG. 4B). These results reveal that, while highly upregulated in melanoma cells, NGLY1 appears to be dispensable for the vitality of human normal cells even in a highly sensitive state like the embryonic stage.

TABLE 1

Immunohistochemistry straining intensity of NGLY1 in human normal skin and melanoma tissues

| Pathology (# of Cases) | Negative (% of total cases) | Weak (% of total cases)[a] | Moderate (% of total cases)[a] | Strong (% of total cases)[a] |
|---|---|---|---|---|
| Normal skin or benign nevus (8) | 8 (100) | 0 (0) | 0 (0) | 0 (0) |
| Melanoma (33)[b] | 19 (57.6) | 7 (21.2) | 8 (18.2) | 1 (3.0) |

[a] A tissue sample showing either weak, moderate and strong staining of NGLY1 is considered as NGLY1 positive. NGLY1-positive staining is associated with melanoma pathology (P = 0.035, 2 × 2 contigency table, Fisher's exact test).
[b] The tumor sample from 1 of 36 melanoma patients was lost during the staining process. Since no visible cancer cell was found in the lymph node tissue samples supposed to contain metastatic melanoma cells of two patients, these two patients were excluded from the analysis.

Example 2—Inducible Knockdown of NGLY1 in Human Cancer Cells

Figure 5A:
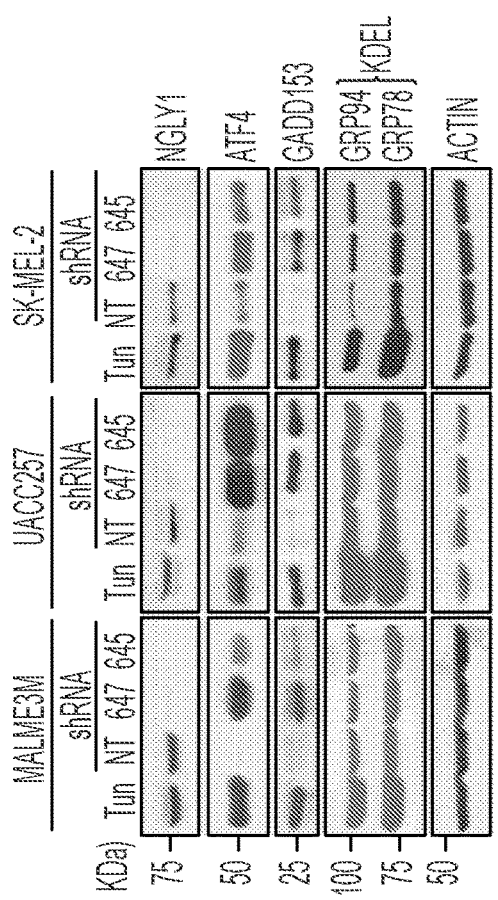
FIGS. 5A-5G shows ER stress-associated apoptosis and synergistic anticancer responses induced by NGLY1 knockdown in melanoma cells.
Figure 5B:
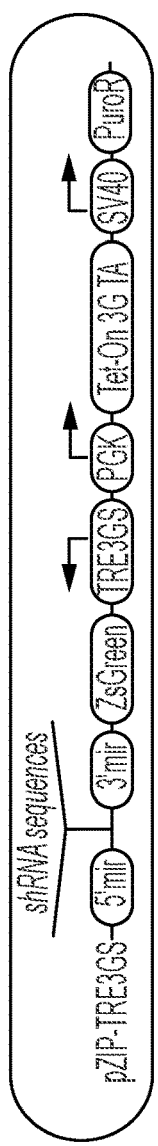
Figure 5B:
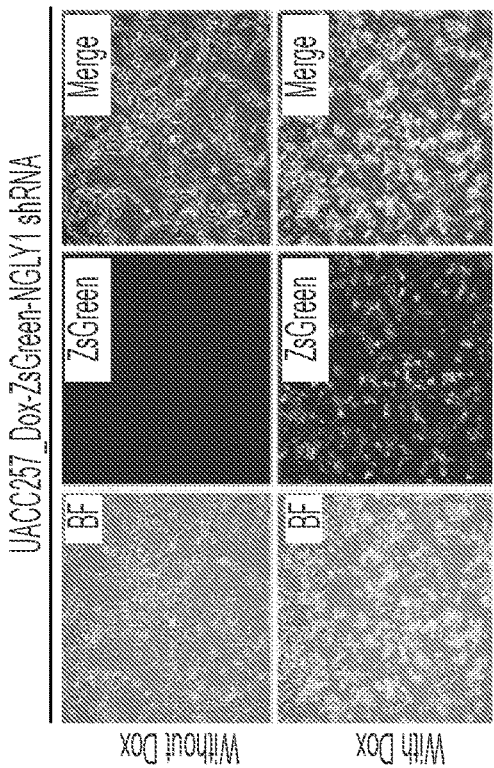
Figure 5C:
Figure 5D:
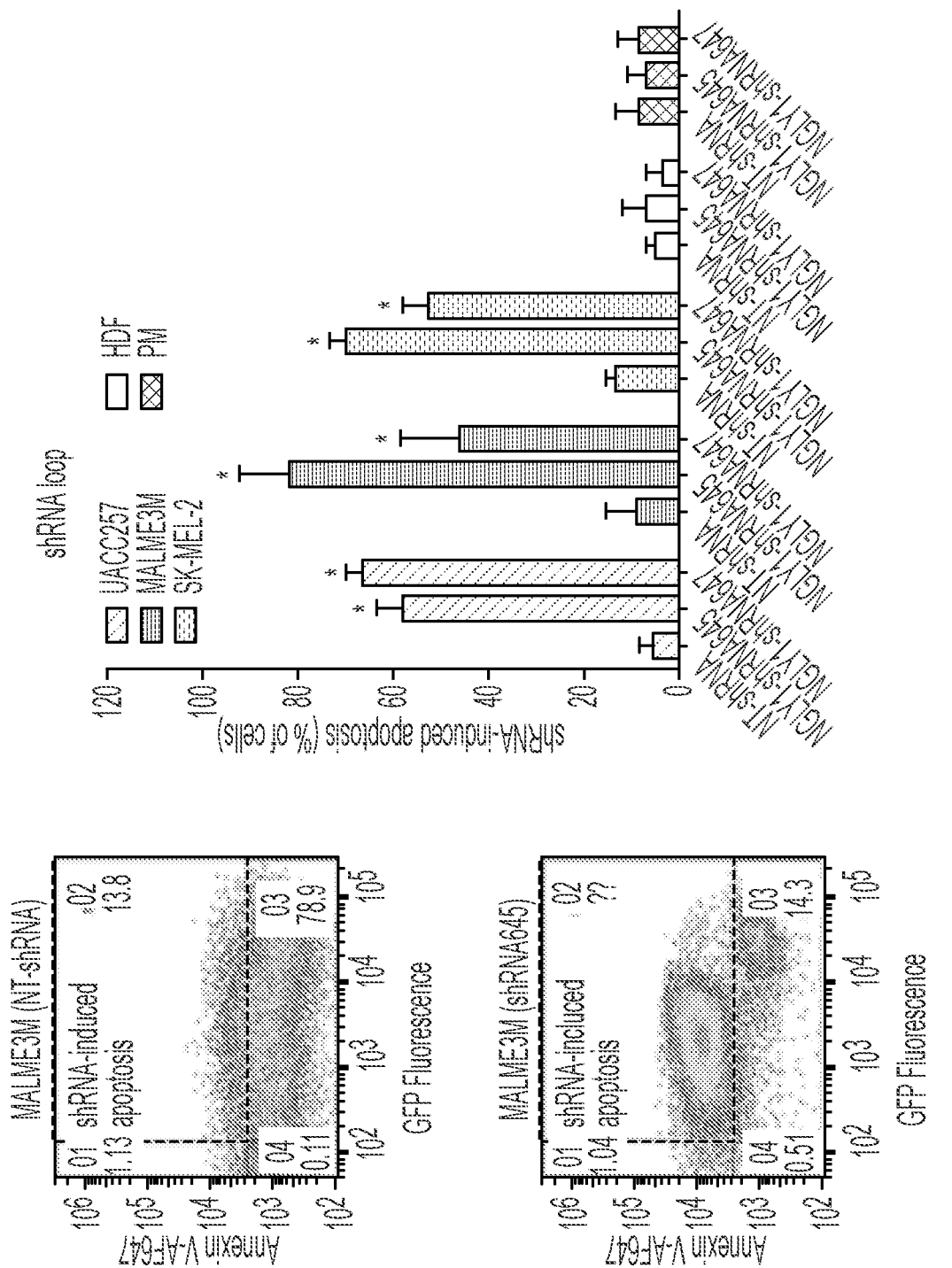
Figure 5E:
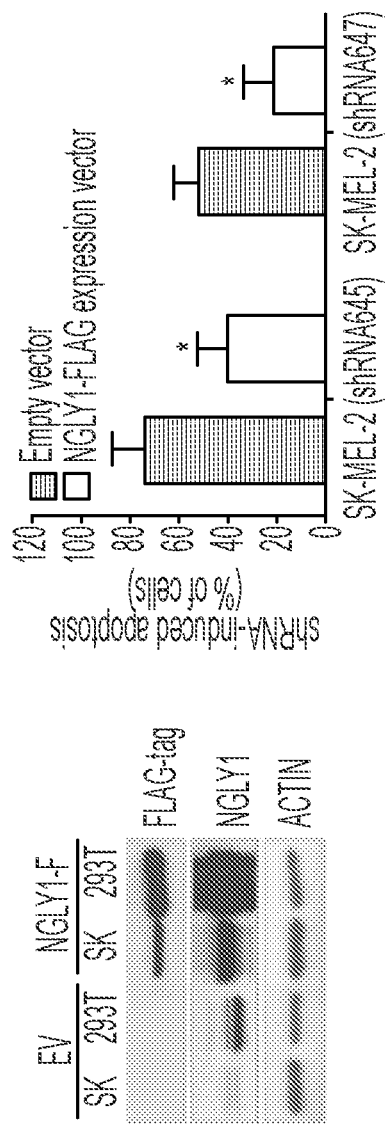

To enable the inducible inhibition of NGLY1, two independent shRNA sequences (shRNA645 and shRNA647) have been identified that can lead to more than 85% of NGLY1 knockdown efficiency at the RNA level in 293T cells. These NGLY1-targeting shRNA sequences and a scrambled (non-targeting) shRNA sequence were cloned into doxycycline (dox)-inducible, polycistronic green fluorescence protein (GFP)-shRNA expression constructs (a pZIP inducible lentiviral vector, TransOMIC). Stable clones have been generated with the shRNA expression constructs in multiple human melanoma cell lines, including MALME3M, UACC257, SK-MEL-2, and COLO829 melanoma cells. The stable clones of melanoma cells showed clear GFP expression upon dox treatment (FIG. 5A; FIG. 5B), indicating the expression of shRNA sequences. Compared with the cells expressing the NT-shRNA, the expression of NGLY1 was largely suppressed by NGLY1-shRNA645 and NGLY1-shRNA647 and hardly detectable in the stable clones of MALME3M, UACC257 and SK-MEL-2 cells with 48-hour treatment of dox (FIG. 5C). Upon NGLY1 knockdown, melanoma cells showed morphological features of apoptosis, including shrinkage, fragmentation and detachment (FIG. 5B). Similar knockdown effects were found in the stable clones of other melanoma cells with this particular NGLY1 shRNA sequence. After 48-hour treatment of dox, dramatic cell death was observed in the stable clones of UACC257 cells with inducible NGLY1 shRNA sequences (FIG. 5B). This cell-death response was absent in the non-induced cells of the same clone, the stable clone of UACC257 cells with inducible scrambled shRNA (FIG. 5B), and human normal fibroblasts with inducible NGLY1 shRNA (FIG. 5D), strongly suggesting that NGLY1 suppression can trigger apoptosis that is highly specific in human cancer cells. Similar to human normal fibroblasts, normal melanocytes (FIG. 5D) and keratinocytes appeared to well tolerate NGLY1 knockdown and show no sign of increased cell death. In addition, SK-MEL-2, MALME3M cells that express inducible NGLY1 shRNA presented significant apoptosis, compared to their scrambled RNA-expressing counterparts. The expression of exogenous human NGLY1 in melanoma cells attenuated NGLY1-targeting shRNA-induced apoptosis (FIG. 5E). These definitive data from the preliminary study indicate that targeting NGLY1 and the deglycosylation of denatured proteins could be a highly effective and rather safe anti-melanoma approach.

Figure 6:
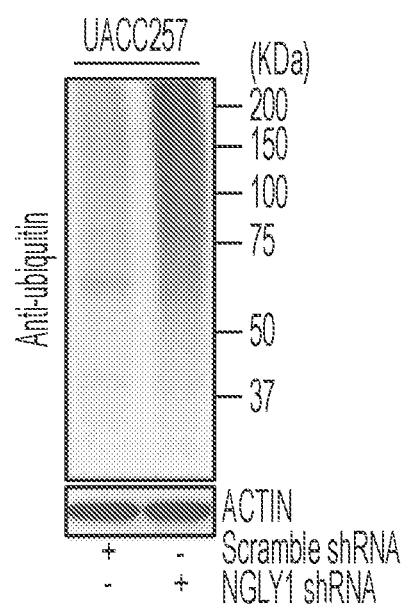
FIG. 6 shows NGLY1 knockdown led to an increase of ubiquitinated proteins detected in UACC257 melanoma cells that were treated with 25 µg/ml cycloheximide (a blocker of protein synthesis) for 6 hours.

Example 3—Perturbation of Protein Homeostasis and Deglycosylation in Cancer Cells with NGLY1 Knockdown By detecting ubiquitinated proteins, it was tested whether the proteasome-mediated protein degradation is disrupted by NGLY1 knockdown in melanoma cells. As shown in FIG. 6, NGLY1 knockdown hindered proteasome-mediated protein degradation, indicated by the accumulation of ubiquitinated proteins in UACC257 cells. The NGLY1 knockdown-induced upregulation of ATF4 and GADD153 was detected in MALME3M, UACC257 and SK-MEL-2 melanoma cells (FIG. 5C). In addition, This finding is consistent with the previously observed suppression of ERAD in cells with NGLY1 malfunction (Enns, et al., 2014; Huang, et al., 2015; Koizumi, et al., 2016; Lehrbach and Ruvkun, 2016; Owings, et al., 2018; Suzuki, 2015; Tomlin, et al., 2017). Since GADD153 is an important mediator for ER stress-associated apoptosis (Wang, et al., 2008), our findings suggest that ER stress signaling-mediated apoptosis may contribute to the death of melanoma cells with NGLY1 suppression. Using flow cytometry analysis, a substantial increase of apoptosis was detected in NGLY1-knockdown melanoma cells, which was absent in the cancer cells expressing NT-shRNA and normal cells expressing NGLY1-targeting shRNA (FIG. 5D). Overexpression of exogenous human NGLY1 and knockdown of GADD153 both attenuated apoptosis induced by NGLY1 knockdown in SK-MEL-2 cells (FIG. 5E; FIG.

8). Taken together, stress response-associated, GADD153-mediated apoptosis contributes to NGLY1 knockdown-induced melanoma cell death.

Figure 7A:
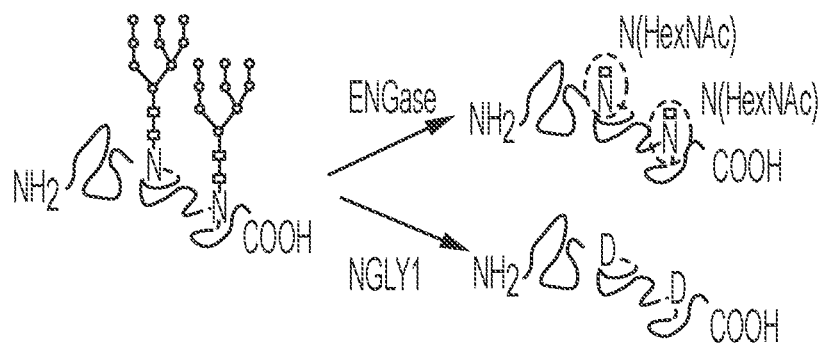
Figure 7A:
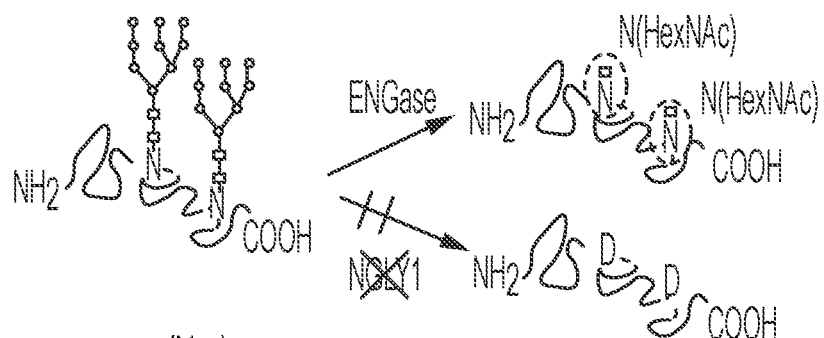
Figure 7B:
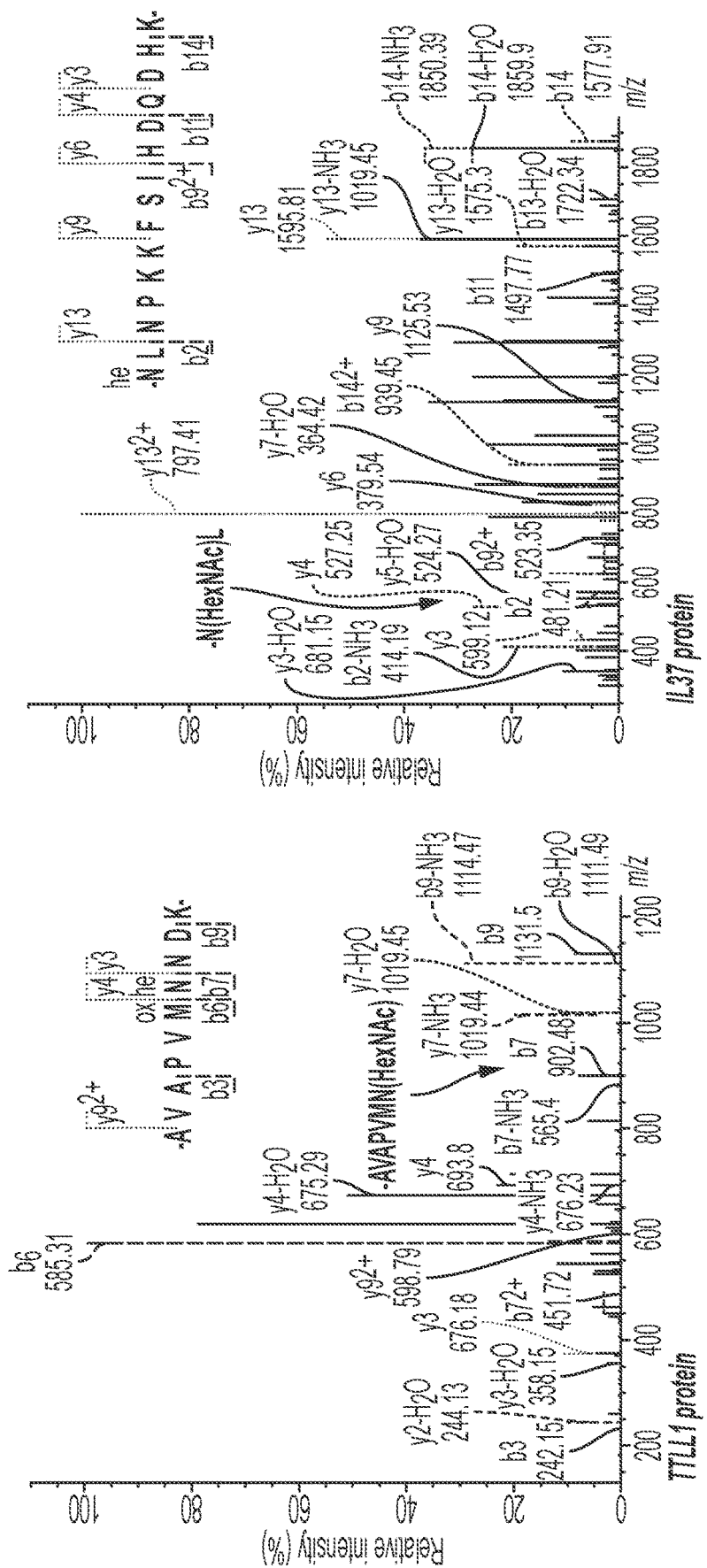
Figure 7B:
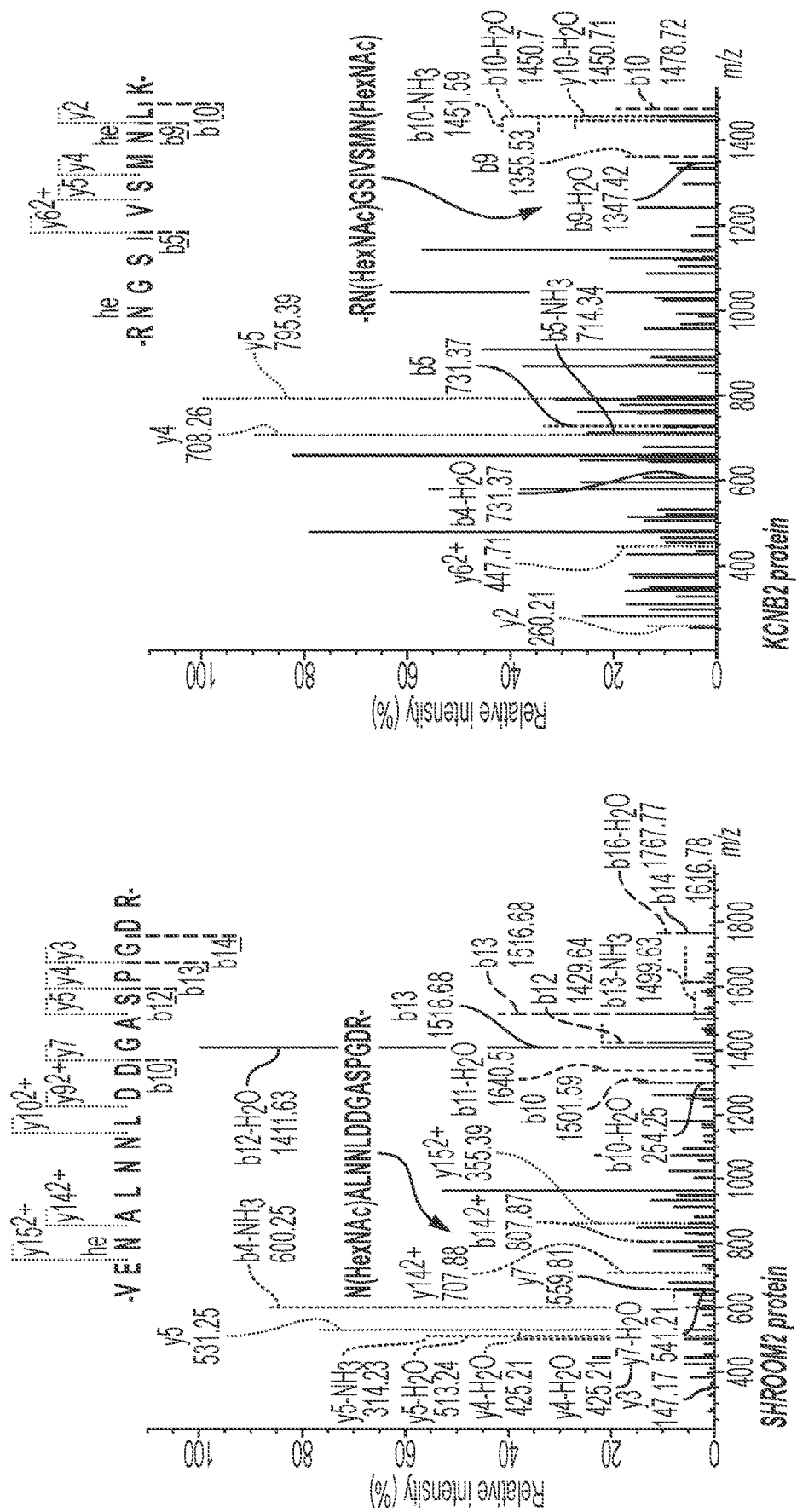
Figure 8A:
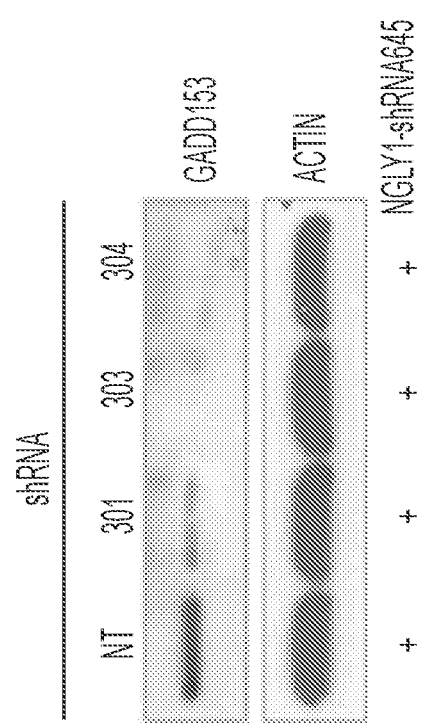
FIGS. 8A-8B show the attenuation of NGLY1 knockdown-induced apoptosis by GADD153 knockdown in melanoma cells.
Figure 8B:
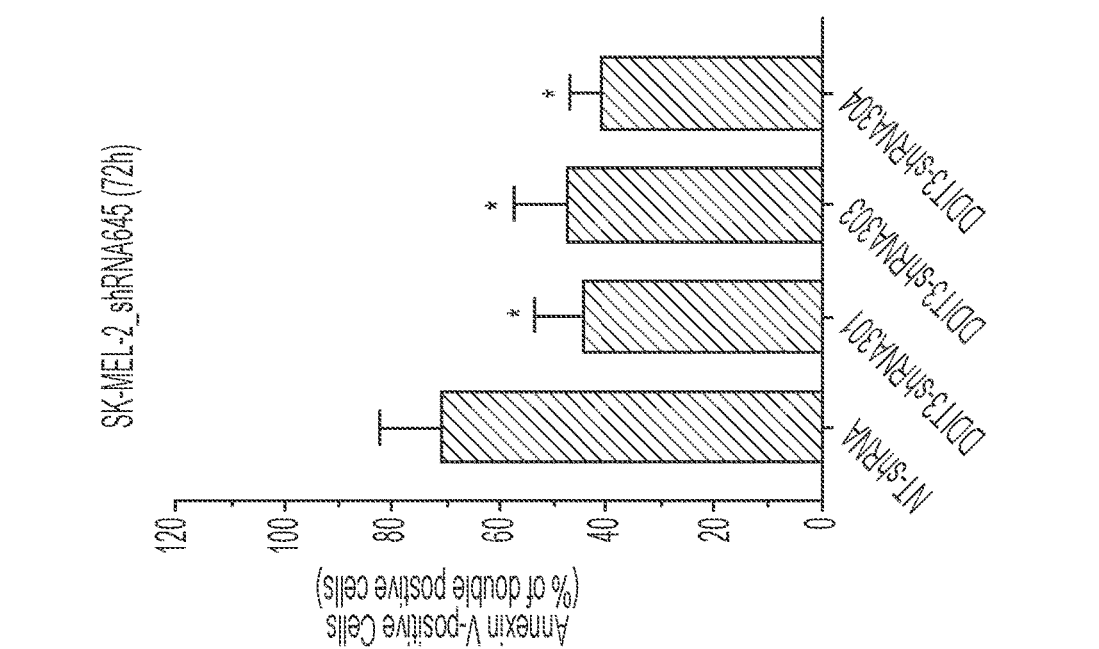
Figure 8B:
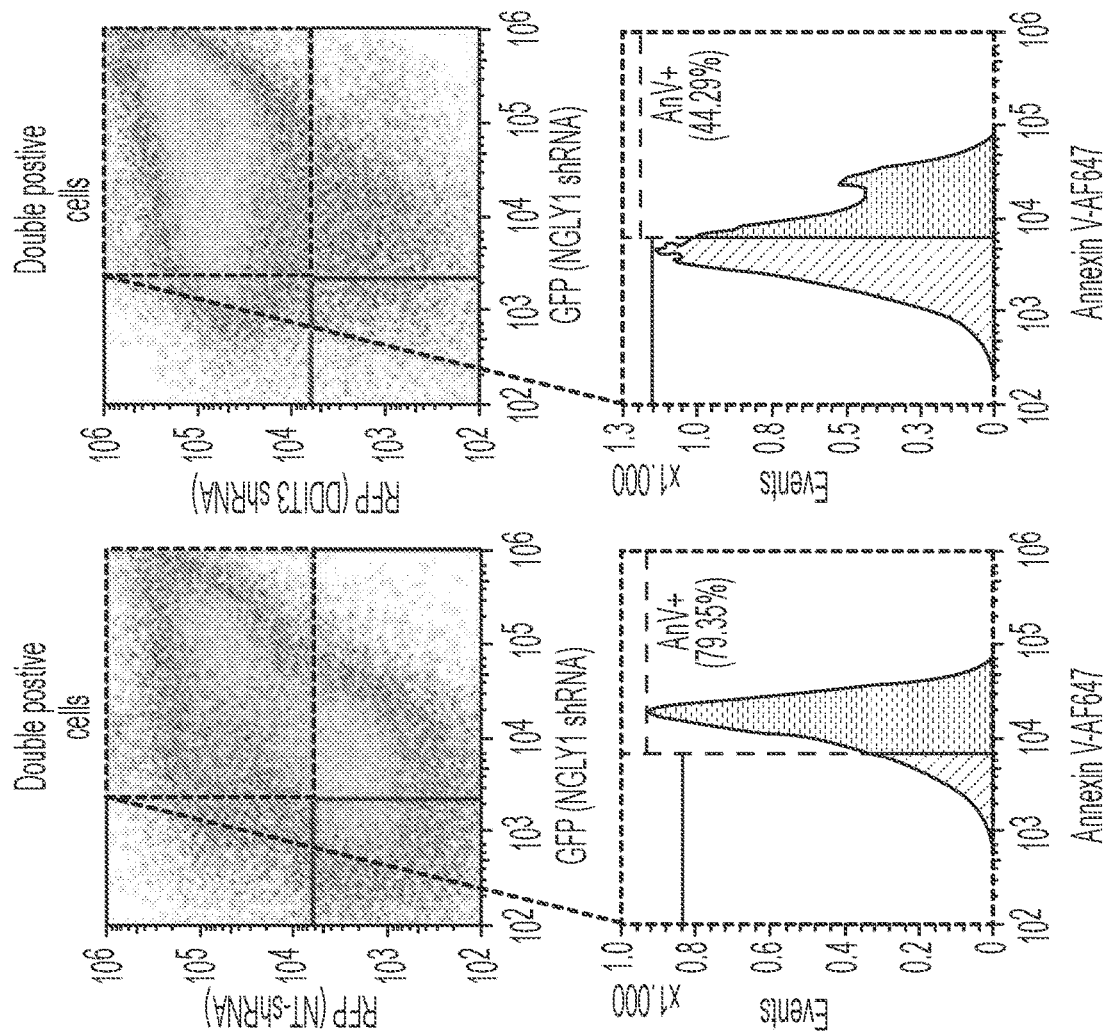

Upon NGLY1 suppression, ENGase has better access to the substrates and generates more products of glycopeptides containing GlcNAc-asparagine residues in cells (FIG. 7A) (Huang, et al., 2015). Using LC-MS/MS-based proteomics analysis, peptides containing GlcNAc-asparagine residues denoted as N(HexNAc) were identified in both control and NGLY1-knockdown samples (FIGS. 7B and 7C). Although the quantities of peptides containing GlcNAc-asparagine that can be detected among the biological replicates of different cell samples appeared to vary, compared with control cells, melanoma cells with NGLY1 knockdown reproducibly showed higher contents of peptides containing GlcNAc-asparagine residues, indicating the functional defect of NGLY1 and the perturbation of protein deglycosylation in the cells (FIG. 7D).

Through proteomic analysis, a higher content of peptides containing GlcNAc-asparagine residues were observed but also identified proteins showing altered abundance in melanoma cells with NGLY1 inhibition (Table 3). However, in transcriptomic analysis, the genes that encode several of these differentially abundant proteins (e.g., PPIA, VDAC1, PRKCSH, LASP1) did not appear differentially expressed at the RNA level in the NGLY1-inhibited cells, indicating that NGLY1 inhibition may affect cell signaling networks by perturbing post-transcriptional or post-translational regulatory mechanisms. The link between NGLY1 and post-translational regulatory mechanisms were also supported by the findings from several recent studies on NGLY1 (Koizumi, et al., 2016; Lehrbach and Ruvkun, 2016; Owings, et al., 2018; Tomlin, et al., 2017).

Although ATF4 and GADD153 were upregulated in NGLY1-knockdown melanoma cells, a clear upregulation of ER chaperones GRP78/94 (FIG. 5C) was not observed. In fact, the abundance of GRP78/94 proteins in melanoma cells determined by mass spectrometry appeared to drop in response to NGLY1 suppression (Table 3). The missing of GRP78/94 upregulation suggests that the NGLY1 suppression-induced activation of ATF4 and GADD153 in melanoma cells may not be directly caused by ER stress.

Example 4—Computational Homology Model for Human NGLY1

Figure 9:
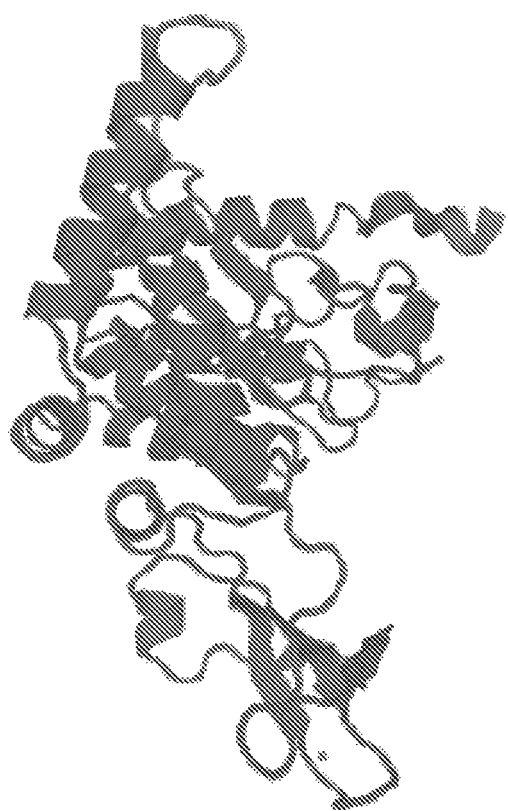
FIG. 9 shows human NGLY1 homology model.

High-resolution structural information based on crystallography data is currently unavailable for human NGLY1. Considering ~90% of the sequences that are identical between human and mouse NGLY1 proteins at the core domain, the crystal structure of mouse NGLY1 (PDB code: 2F4M) was used as a template to build a homology model for human NGLY1 core domain using a widely applied homology modeling web-server, SWISS-MODEL (Biasini et al., 2014). The structure of the human NGLY1 homology model is shown in FIG. 9. To test the use of the current homology model for human NGLY1, in silico docking analysis was performed using the homology model. It is reported that Z-VAD (a benzyloxycarbonyl-Val-Ala-Asp tripeptide) with fluoromethyl group at the C-terminal (Z-VAD-fmk) can penetrate cells and react with yeast and mouse NGLY1 (Misaghi et al., 2004; Zhao et al., 2006) by forming a covalent bond with the cysteine residue at the catalytic site. Using AutoDock (Morris et al., 2009), Z-VAD was docked to the human NGLY1 homology model. As expected, in the human NGLY1 model, the top scored binding poses of Z-VAD include the ones that are similar to the binding pose in the crystal structure of a mouse NGLY1 and Z-VAD complex, indicating that the Z-VAD may also serve as an inhibitor for human NGLY1 through binding to its catalytic site in a similar fashion that Z-VAD can inactivate mouse NGLY1. In addition, the result of this preliminary study also supports the accuracy and suitability of our human NGLY1 homology model for inhibitor screening.

Using the homology model, two published chitobiose-based PNGase inhibitors were evaluated, each with a reactive moiety that can form a covalent bond between the compound and cysteine residues in proteins (Witte et al., 2009). The docking poses showed that the reactive moiety of these known inhibitors pointing towards the cysteine residue at the catalytic site of NGLY1, indicating these chitobiose derivatives are also potential covalent modifiers for human NGLY1 at its catalytic site. Three compounds, L1, L2 and L3, were designed with electrophilic moieties as putative specific inhibitors for NGLY1 and the compounds were docked into the human NGLY1 homology model using AutoDock. The binding poses were evaluated as well as the binding affinities for these three compounds. The compounds were allowed to interact with any available binding pockets (the catalytic site included) in the protein during the docking process. The results suggested that all of the chitobiose-based as well as compounds L1, L2, and L3 may interact with the catalytic site of human NGLY1 in multiple poses among their top 10 binding poses (Table 2).

TABLE 2

Binding affinities between human NGLY1 and its ligands

| Mode | L1 BA | L2 BA | L3 BA | L4 BA | L5 BA | L6 BA |
|---|---|---|---|---|---|---|
| 0 | −6.7 | −6.5 | −6.5 | −7.8 | −6.9 | −7.5 |
| 1 | −6.4 | −6.2 | −6.4 | −7.7 | −6.9 | −7 |
| 2 | −6.3 | −6.1 | −6.3 | −7.5 | −6.8 | −6.8 |
| 3 | −6.2 | −5.9 | −6.2 | −7.4 | −6.8 | −6.6 |
| 4 | −6.1 | −5.9 | −6.2 | −7.2 | −6.7 | −6.5 |
| 5 | −6.1 | −5.9 | −6.2 | −7 | −6.6 | −6.5 |
| 6 | −5.9 | −5.8 | −6.1 | −7 | −6.6 | −6.4 |
| 7 | −5.9 | −5.7 | −6.1 | −7 | −6.6 | −6.3 |
| 8 | −5.9 | −5.7 | −6 | −6.8 | −6.5 | −6.2 |

L1-L3: designed compounds;
L4: Z-VAO;
L5-L6: chitobiosn-hated PNGase inhibitors.
BA = binding affinity values in unit of kcal/mol
Binding site at active site
Most favorable binding pose Among these poses, the pose with the electrophilic reactive moiety of the compound pointing toward the cysteine residue was highlighted. Since a covalent bond should be formed between the compound and the cysteine, these poses (highlighted in dark gray) were defined as the most favorable binding poses. The binding affinities of these most favorable poses for compounds L1, L2, and L3 are −5.9, −6.5 and −6.3 kcal/mol, respectively. The binding affinities of compounds L1, L2, and L3 are comparable with other tested inhibitors (L4, L5, and L6). Considering the variation of the binding affinities calculated in AutoDock is +/−2.0 kcal/mol, it is believed that the compounds of the present disclosure could have comparable inhibitory activity towards human NGLY1 as other potential inhibitors, which illustrates the attractiveness of these compounds as a starting point for further optimization. In it contemplated that this human NGLY1 homology model will be used for the virtual screening and evaluation of human NGLY1 inhibitors that will be developed in further research.

Figure 16A:
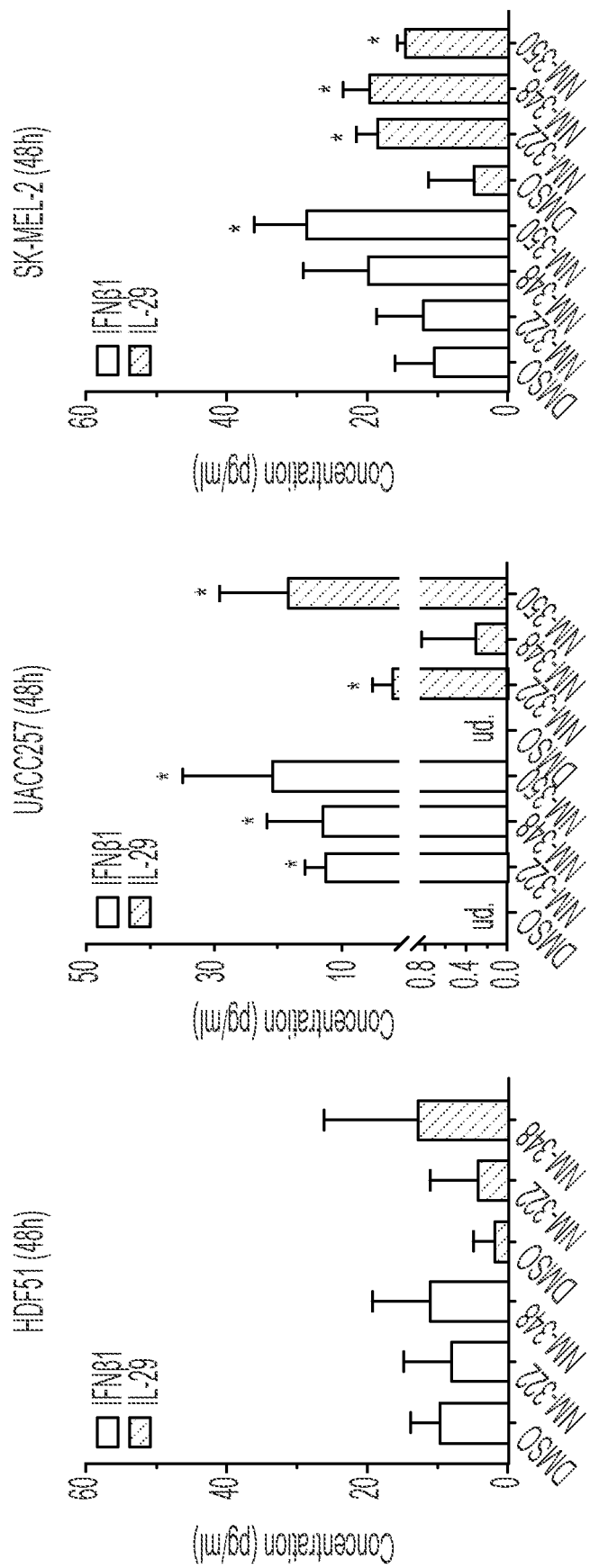
FIGS. 16A & 16B show the cytokine responses and glycopeptide features of melanoma cells treated with novel NGLY1 inhibitors.
Figure 16B:
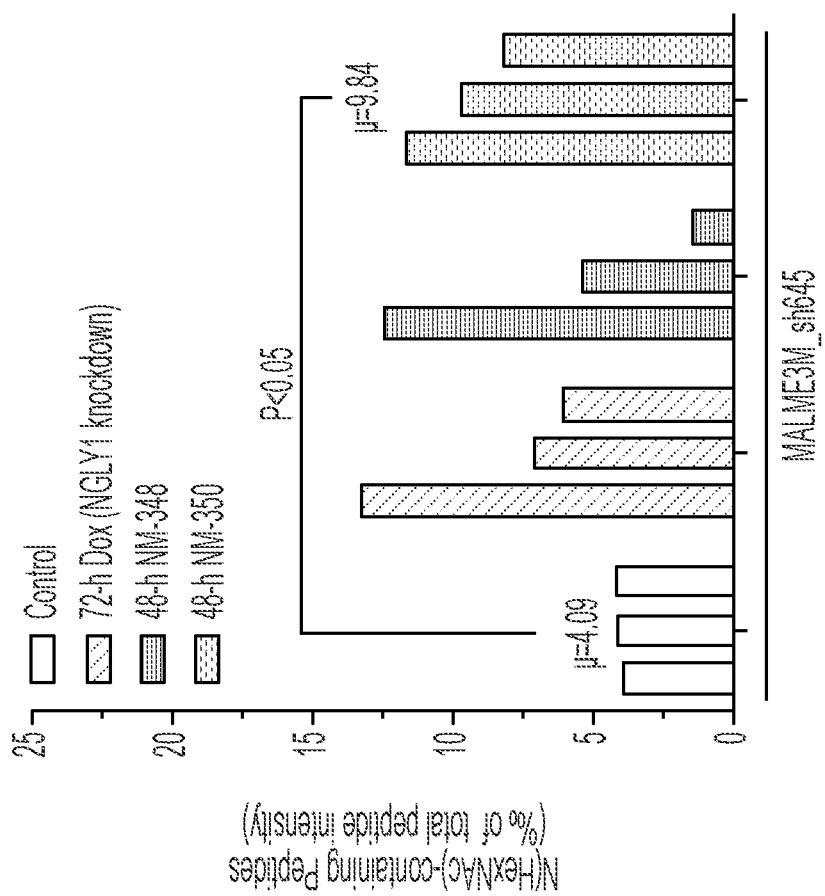

Based on the data of compounds L1, L2 and L3 in the computational study, the fourth analog was designed. As shown in FIG. 16B, these four compounds have been named/renamed as NM-322 (i.e., L1), NM-348 (i.e., L2), NM-350, and NM-354 (i.e., L3) in our later studies and re-evaluated in computational analysis.

Example 5—NGLY1 Suppression-Induced Alterations of Gene Expression in Human Melanoma Cells Global gene expression profiling was performed to study the NGLY1 deficiency-associated transcriptomic alterations in melanoma cells. Gene expression in the control and NGLY1-knockdown cells was analyzed using HT-12v4 array chips (Illumina). Total RNA from each cell sample was isolated using the mirVana RNA Isolation Kit (Thermo Fisher Scientific). The tagged cRNA copies of each mRNA in a total RNA sample was generated using the Illumina TotalPrep-96 RNA amplification kit (Thermo Fisher Scientific) and hybridized with the HT-12v4 array chips, according to the manufacturer's protocols that are frequently performed by the inventors or their colleagues (Jones et al., 2013; Liao et al., 2013; Nazor et al., 2012; Wang et al., 2011). The location of each sample on the array chips was assigned through randomization. The intensity of fluorescence on the array chips was determined using the HiScan array scanner (Illumina).

Figure 10A:
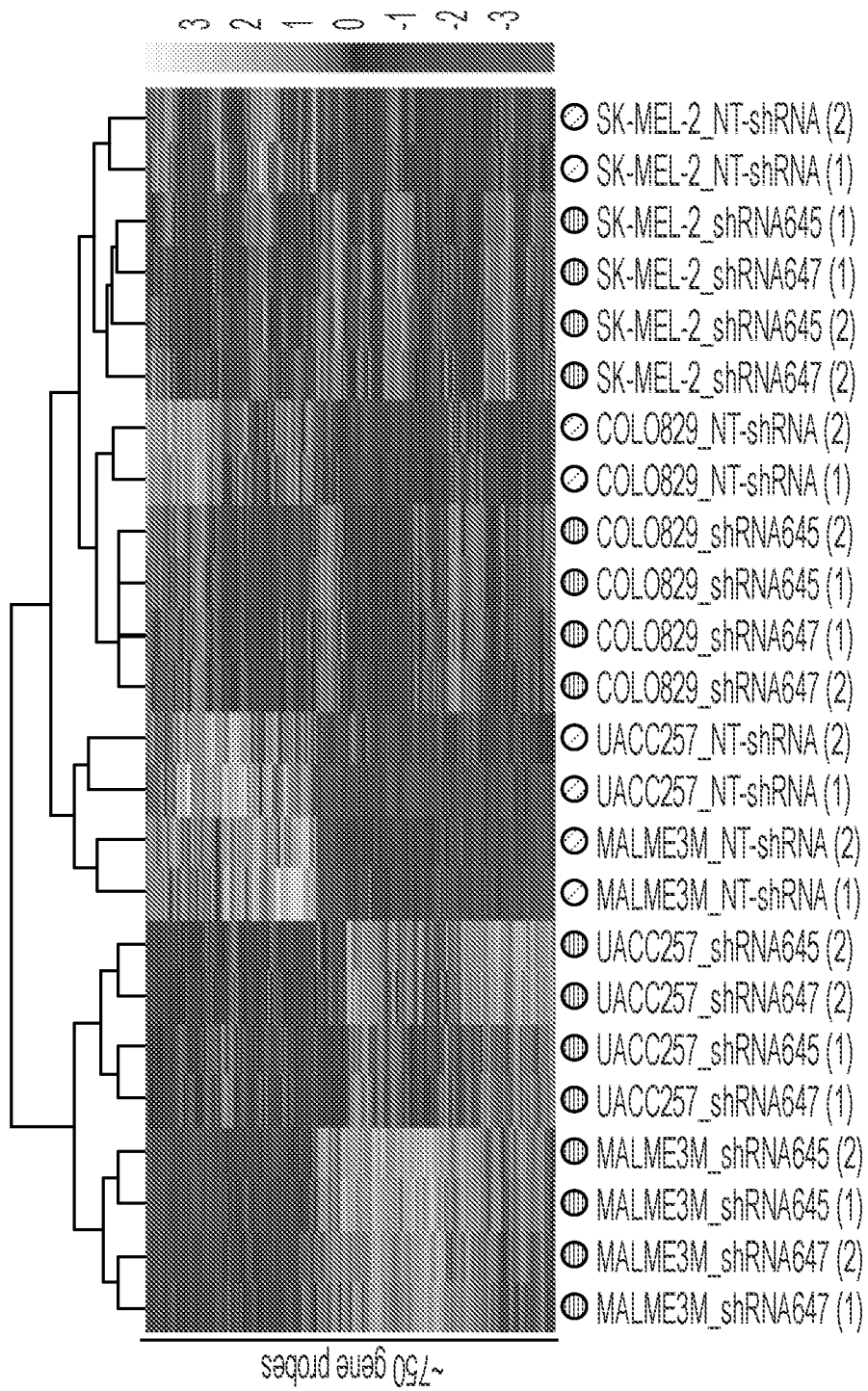

After the array data were acquired, the data of each sample was normalized using the LUMI package in R with the RSN method. Subsequently, the Qlucore Omics Explorer 3.0 was used to perform multivariate statistical analysis, unsupervised clustering and supervised clustering on the normalized array data to identify differentially expressed genes (P<0.01, fold change ≥2.0, prioritization of candidate genes according to their magnitudes of fold change) and examine the similarity of expression profiles among different samples (FIG. 10A). The differential expression of selected genes was validated by qRT-PCR using TaqMan gene expression assays (Thermo Fisher Scientific) (FIG. 10B; FIG. 10C). Gene ontology analysis was performed on the genes with NGLY1 knockdown-induced differential expression and found that the knockdown of NGLY1 expression in melanoma cells has pleiotropic effects on their molecular features and the regulation of signaling networks.

From the global gene expression profiling, it has been particularly noticed that the expression of many immune-relevant genes (e.g., IFNβ1, IL-29, HLA-F and CCL5 genes) is upregulated in melanoma cells with NGLY1 knockdown. This indicated that targeting NGLY1 in melanoma is likely to alter tumor immunity and trigger anticancer immune responses in cancer patients.

In proteomic analysis, many proteins also presented differential abundance in melanoma cells in response to NGLY1 knockdown (Table 3). Among the proteins with reduced abundance in the NGLY1-knockdown cells, several of them (e.g., VCP, PDIA4, HSPA5 and HIST1H4A) have been linked to the survival and drug resistance of cancer cells (Anderson, et al., 2015; Cerezo, et al., 2016; Kuo, et al., 2017; Wang, et al., 2017). Thus, part of the anti-melanoma responses associated with NGLY1 inhibition may be attributed to the modulation of these gene products.

Figure 10B:
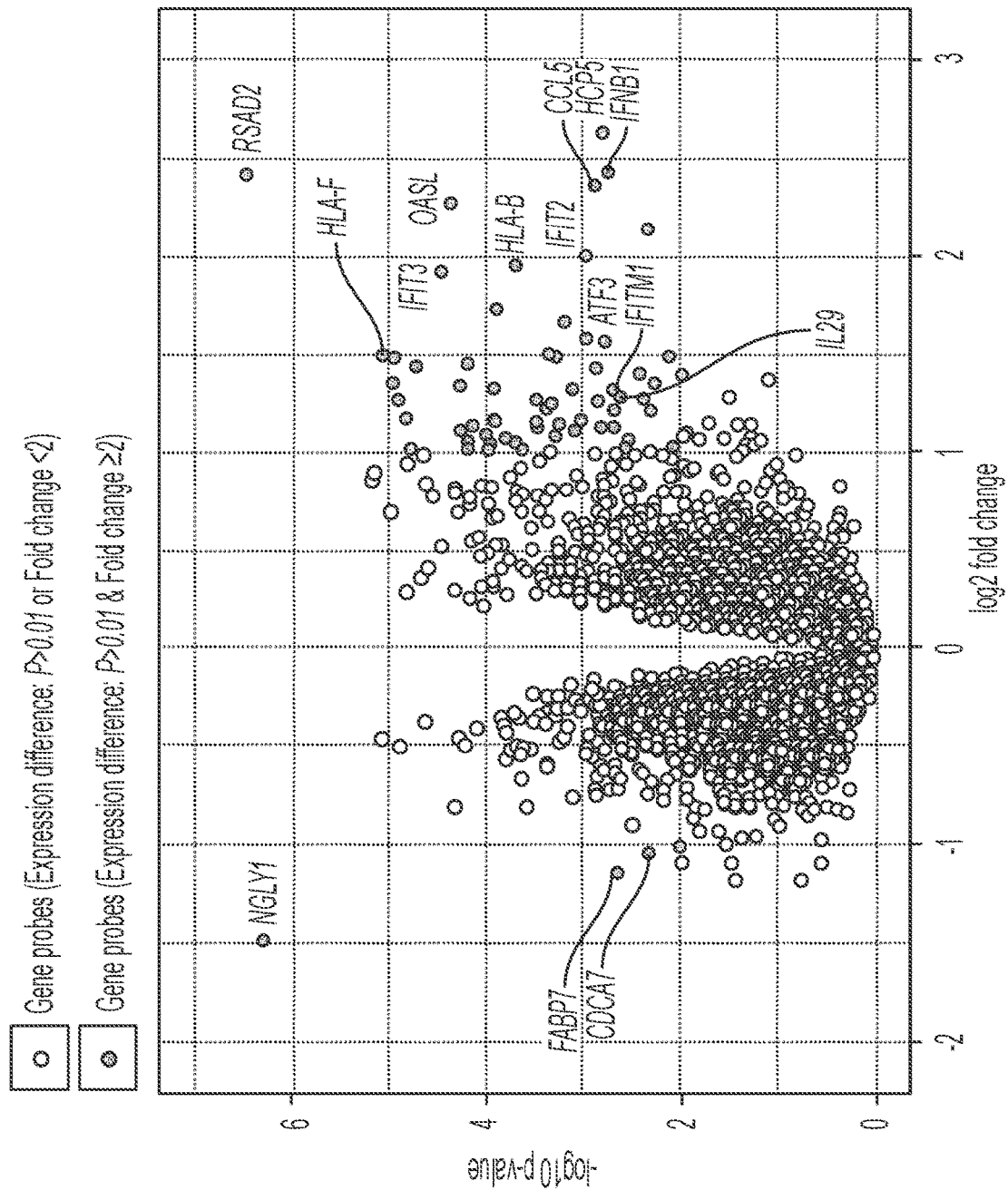
Figure 10C:
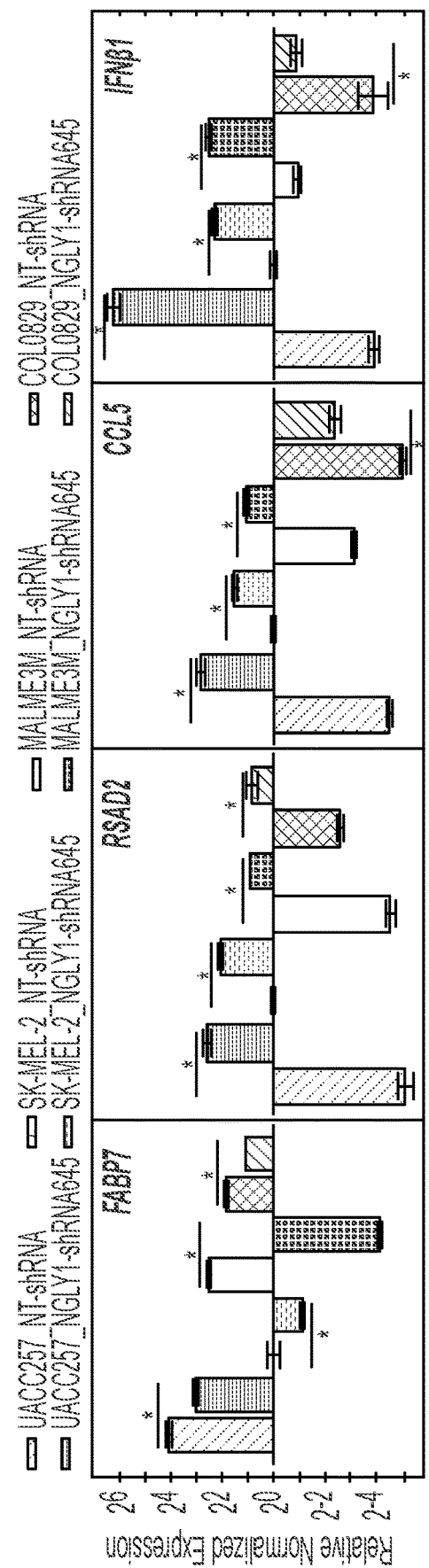
Figure 10B:
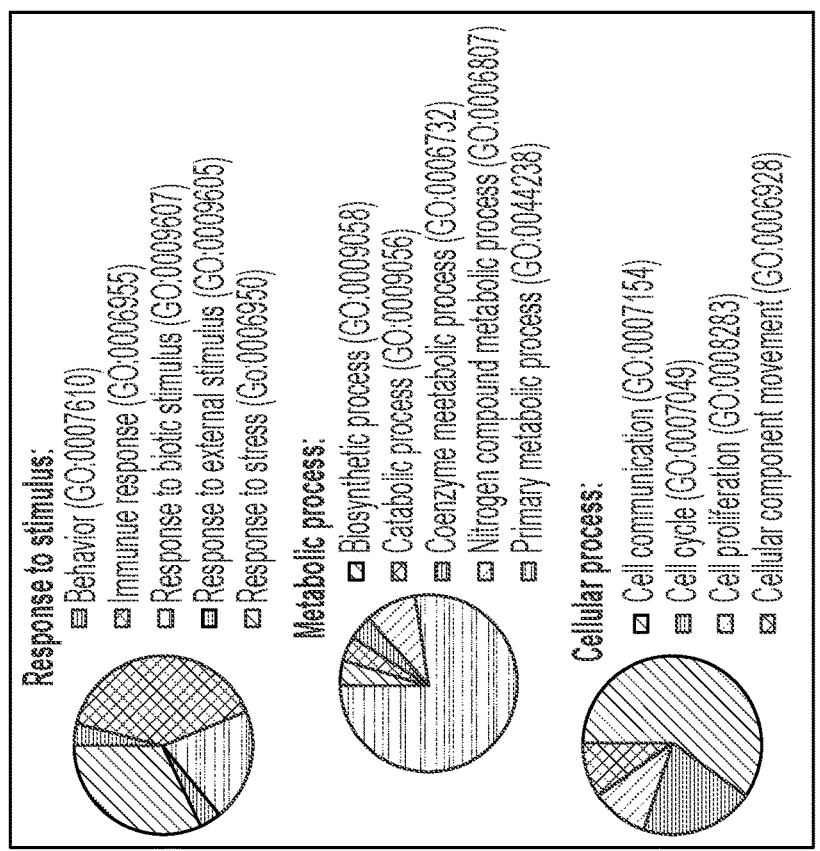
Figure 10B:
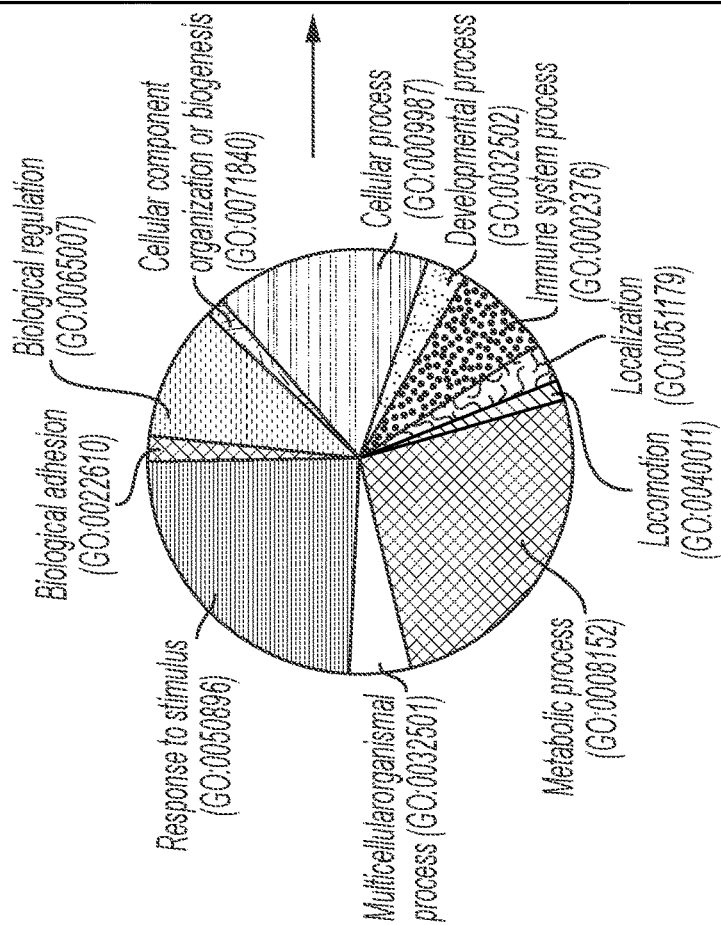

Through global gene expression profiling, it was discovered that, in addition to the activation of stress-response signaling, NGLY1 suppression in melanoma cells causes the significant upregulation of interferon genes that have well documented anticancer activity (FIG. 10B). The data (FIG. 11) demonstrated that the surge of IFNβ1 and IL-29 plays an important role in melanoma cell death as the consequence of NGLY1 inhibition. NGLY1 suppression-stimulated cytokine responses also offer direct evidence supporting the feasibility of immunomodulation, particularly in malignant cells, by targeting NGLY1. A recent study has revealed that the activation of type I interferon (e.g., Ifnb1) signaling and immunogenic cell death potentiates the antitumor efficacy of anti-PD-1 antibody in syngeneic mouse tumor models of colon and bladder cancer (Hossain, et al., 2018). Since anti-PD-1 antibodies such as nivolumab and pembrolizumab are used for treating patients with melanoma and non-small cell lung cancer, it is reasonable to consider the induction of cytokine surges, including IFNβ1, by targeting NGLY1 as a promising approach to enhance the efficacy of immune checkpoint therapies in these patients. Thus, NGLY1 suppression is likely to potentiate the anticancer activity of immune modulatory agents currently used in the clinic. In the future, the immune responses triggered by NGLY1 inhibition may be exploited for antiviral purposes because the NGLY1 suppression-activated cytokine signaling is also relevant to antiviral responses in cells (Ivashkiv and Donlin, 2014).

TABLE 3

NGLY1 inactivation-induced alterations in protein abundance detected by proteomics analysis

| | | MALME3M | | | SK-MEL-2 | | |
|---|---|---|---|---|---|---|---|
| Protein IDs | Genes | Avg. % of total peptides (Control, n = 3) | Avg. % of total peptides (NGLY1-KD, n = 3) | Abundance fold change (KD/Control)* | Avg. % of total peptides (Control, n = 3) | Avg. % of total peptides (NGLY1-KD, n = 3) | Abundance fold change (KD/Control)* |
| Proteins with increased abundance commonly found in MALME3M and SK-MEL-2 cells with NGLY1 knockdown | | | | | | | |
| P62937; Q9Y536 | PPIA | 1.3637 | 1.6296 | 1.1950 | 1.2622 | 4.4404 | 3.5180 |
| P49903 | SEPHS1 | 0.0000 | 0.0121 | n.d. in control samples | 0.0154 | 0.0397 | 2.5857 |
| Q71U36; P68363; Q13748; P68366; Q6PEY2 | TUBA1A; TUBA1B; TUBA3C; TUBA4A | 1.9826 | 2.4477 | 1.2346 | 1.5769 | 3.7260 | 2.3628 |
| P21796 | VDAC1# | 0.0696 | 0.1067 | 1.5331 | 0.1777 | 0.4163 | 2.3423 |
| Q7KZF4 | SND1 | 0.2903 | 0.3381 | 1.1646 | 0.2098 | 0.3684 | 1.7558 |
| Q5VTE0; P68104; Q05639 | EEF1A1P5; EEF1A1; EEF1A2 | 2.1861 | 2.6168 | 1.1970 | 2.0729 | 3.5754 | 1.7248 |

TABLE 3-continued

NGLY1 inactivation-induced alterations in protein abundance detected by proteomics analysis

| | | MALME3M | | | SK-MEL-2 | | |
|---|---|---|---|---|---|---|---|
| Protein IDs | Genes | Avg. % of total peptides (Control, n = 3) | Avg. % of total peptides (NGLY1-KD, n = 3) | Abundance fold change (KD/Control)* | Avg. % of total peptides (Control, n = 3) | Avg. % of total peptides (NGLY1-KD, n = 3) | Abundance fold change (KD/Control)* |
| P25705 | ATP5A1 | 0.3353 | 0.6229 | 1.8579 | 0.1367 | 0.2250 | 1.6451 |
| P63261; P60709; P63267; P68133; P68032; P62736 | ACTG1; ACTB; ACTG2; ACTA1; ACTC1; ACTA2 | 15.8514 | 19.9151 | 1.2564 | 12.4899 | 20.5437 | 1.6448 |
| P30101 | PDIA3 | 0.8989 | 1.4247 | 1.5849 | 0.4545 | 0.7444 | 1.6379 |
| P10809 | HSPD1# | 1.9390 | 2.3958 | 1.2356 | 1.8716 | 2.8825 | 1.5401 |
| O43707 | ACTN4 | 0.3716 | 0.5029 | 1.3533 | 0.4010 | 0.6119 | 1.5258 |
| P50991 | CCT4 | 0.2826 | 0.4360 | 1.5428 | 0.3104 | 0.4672 | 1.5052 |
| P49006 | MARCKSL1 | 0.5431 | 0.6807 | 1.2533 | 0.4021 | 0.4889 | 1.2160 |
| Q8NC51 | SERBP1 | 0.3675 | 0.5570 | 1.5155 | 0.4059 | 0.4819 | 1.1871 |
| Q15942 | ZYX | 0.0284 | 0.1168 | 4.1198 | 0.0282 | 0.0322 | 1.1419 |
| Q96QR8 | PURB | 0.0230 | 0.0302 | 1.3177 | 0.0370 | 0.0411 | 1.1104 |
| Proteins with reduced abundance commonly found in MALME3M and SK-MEL-2 cells with NGLY1 knockdown | | | | | | | |
| P14314 | PRKCSH | 0.1371 | 0.0000 | n.d. in NGLY1-KD samples | 0.5048 | 0.4438 | 0.8792 |
| P08670 | VIM# | 9.4669 | 6.9682 | 0.7361 | 6.3892 | 4.9337 | 0.7722 |
| P61978 | HNRNPK | 0.3374 | 0.2840 | 0.8418 | 0.4715 | 0.3634 | 0.7706 |
| P16949 | STMN1 | 0.1663 | 0.0000 | n.d. in NGLY1-KD samples | 0.2708 | 0.2026 | 0.7482 |
| P55072 | VCP# | 0.2390 | 0.1532 | 0.6412 | 0.2363 | 0.1755 | 0.7428 |
| Q99714 | HSD17B10 | 0.0246 | 0.0000 | n.d. in NGLY1-KD samples | 0.0513 | 0.0331 | 0.6443 |
| P11021 | HSPA5 (GRP78) | 0.4052 | 0.2222 | 0.5485 | 0.5763 | 0.3493 | 0.6062 |
| P14625; Q5BFF3 | HSP90B1 (GRP94) | 0.6381 | 0.2500 | 0.3918 | 0.2317 | 0.1370 | 0.5914 |
| P35268 | RPL22 | 0.3121 | 0.2614 | 0.8377 | 0.4938 | 0.2506 | 0.5075 |
| Q5JTV8 | TOR1AIP1 | 0.0220 | 0.0000 | n.d. in NGLY1-KD samples | 0.0031 | 0.0000 | n.d. in NGLY1-KD samples |
| P34932 | HSPA4 | 0.0063 | 0.0000 | n.d. in NGLY1-KD samples | 0.0063 | 0.0000 | n.d. in NGLY1-KD samples |
| P52907 | CAPZA1 | 0.0123 | 0.0000 | n.d. in NGLY1-KD samples | 0.0109 | 0.0000 | n.d. in NGLY1-KD samples |
| Q01082 | SPTBN1 | 0.0369 | 0.0000 | n.d. in NGLY1-KD samples | 0.0115 | 0.0000 | n.d. in NGLY1-KD samples |
| Q14847 | LASP1 | 0.0313 | 0.0000 | n.d. in NGLY1-KD samples | 0.0198 | 0.0000 | n.d. in NGLY1-KD samples |
| P40925 | MDH1 | 0.1165 | 0.0000 | n.d. in NGLY1-KD samples | 0.0219 | 0.0000 | n.d. in NGLY1-KD samples |
| P46779 | RPL28 | 0.0293 | 0.0000 | n.d. in NGLY1-KD samples | 0.0296 | 0.0000 | n.d. in NGLY1-KD samples |
| P13667 | PDIA4 | 0.2196 | 0.0000 | n.d. in NGLY1-KD samples | 0.0362 | 0.0000 | n.d. in NGLY1-KD samples |
| P35527; CON_P35527 | KRT9 | 0.0783 | 0.0000 | n.d. in NGLY1-KD samples | 0.0640 | 0.0000 | n.d. in NGLY1-KD samples |
| P06454 | PTMA | 0.0983 | 0.0442 | 0.4497 | 0.0767 | 0.0000 | n.d. in NGLY1-KD samples |
| P62829 | RPL23 | 0.0742 | 0.0000 | n.d. in NGLY1-KD samples | 0.1392 | 0.0000 | n.d. in NGLY1-KD samples |
| P62805 | HIST1H4A (histone H4) | 1.2159 | 0.2125 | 0.1748 | 0.4122 | 0.0000 | n.d. in NGLY1-KD samples |

Figure 10F:
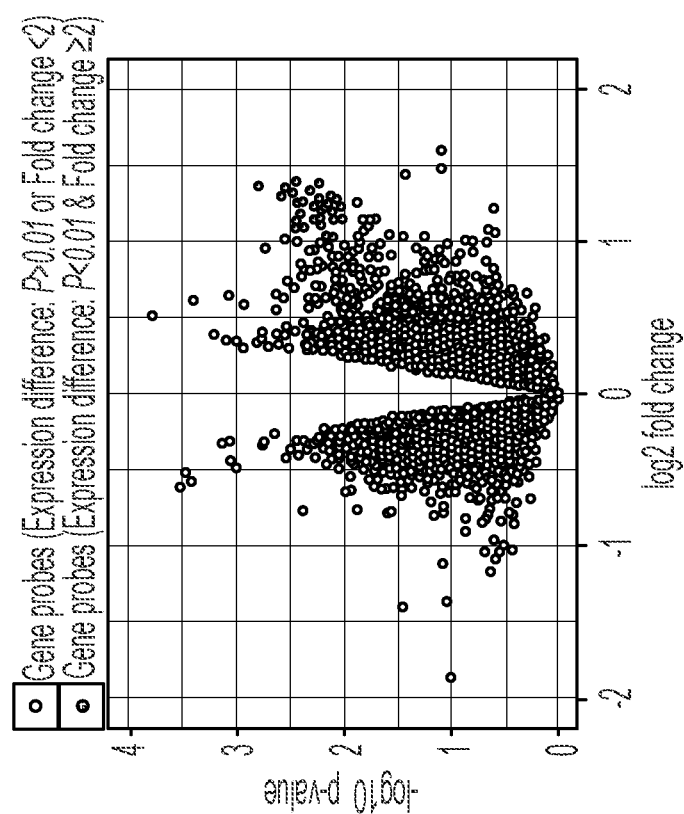
Figure 10E:
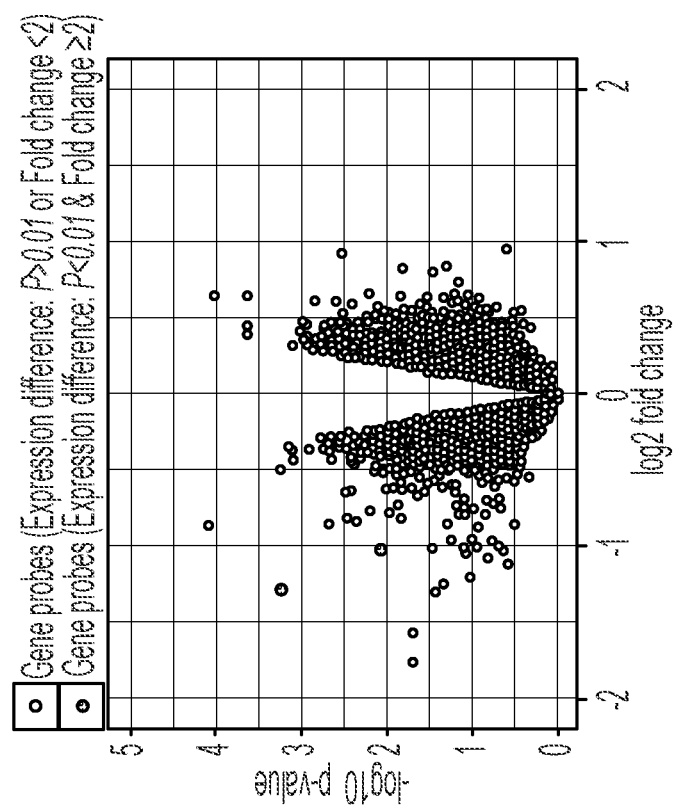
Figure 11A:
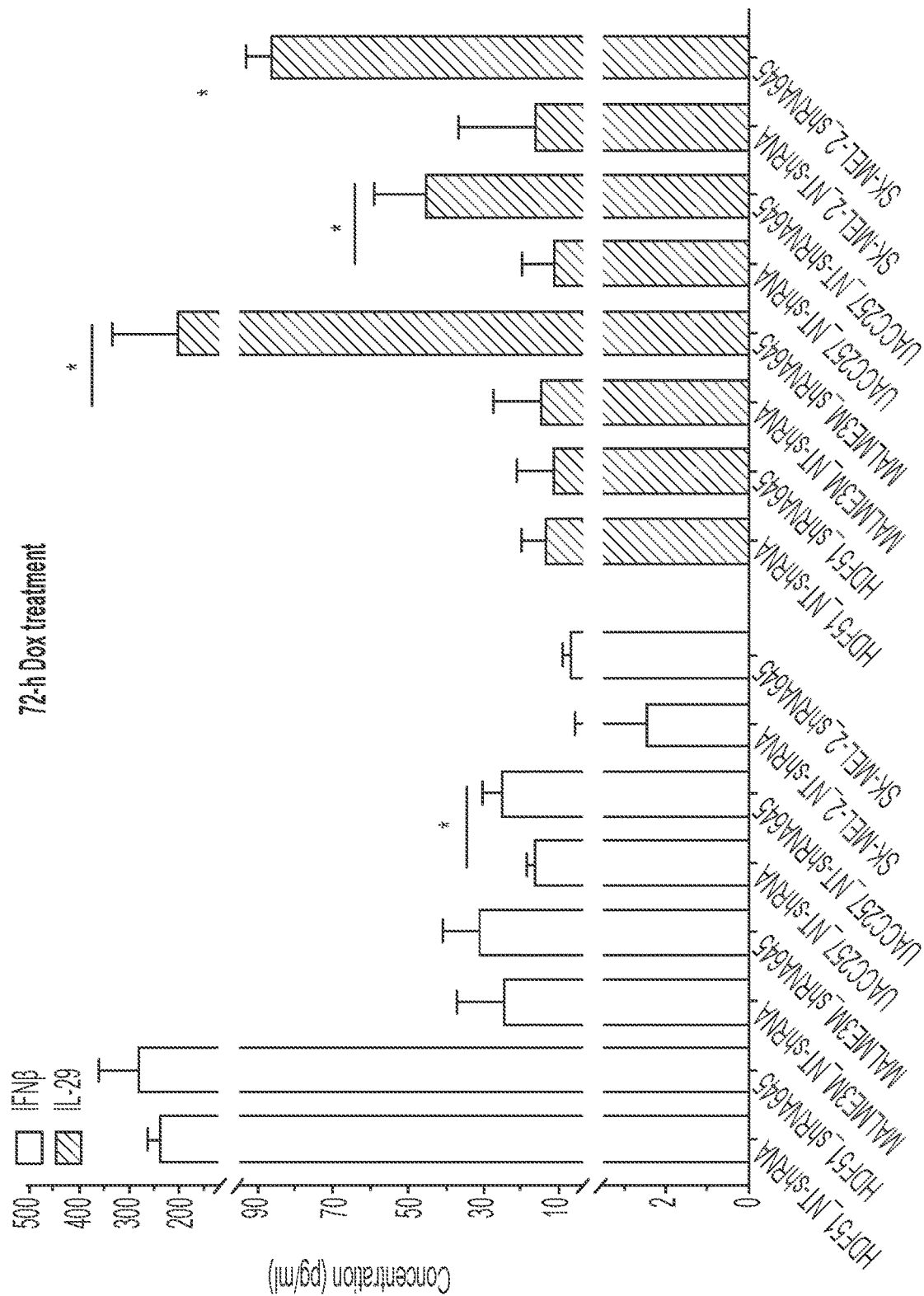
FIGS. 11A-11D show NGLY1 suppression enhanced the production of IFNβ1 and IL-29 that contributes to viability reduction in melanoma cells.
Figure 11B:
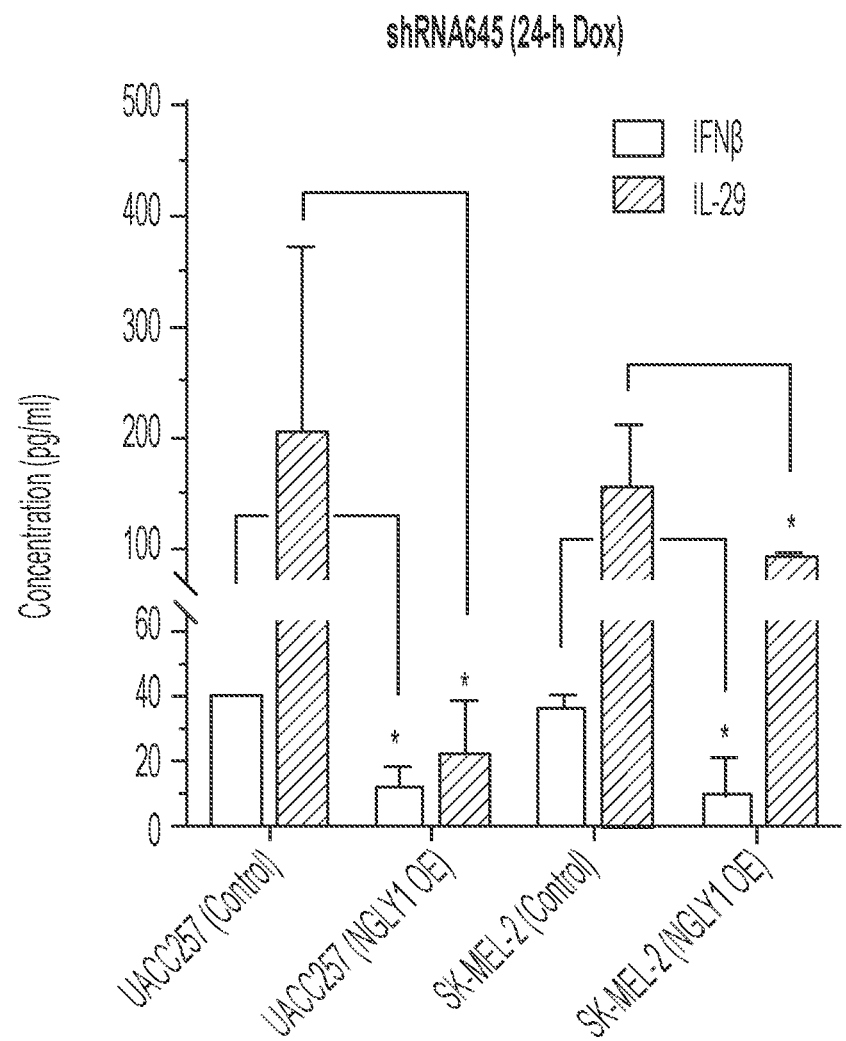
Figure 11C:
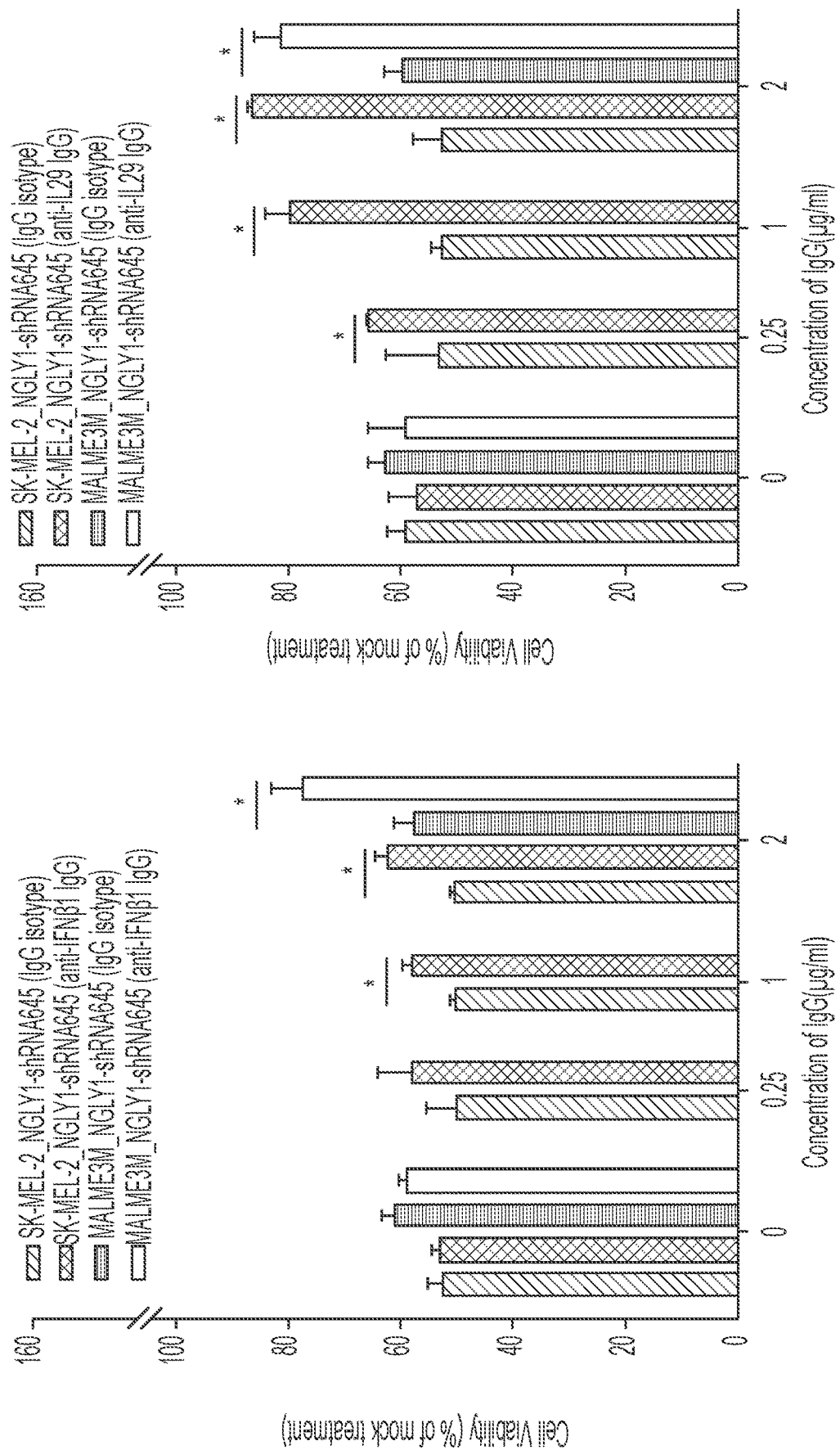
Figure 11D:
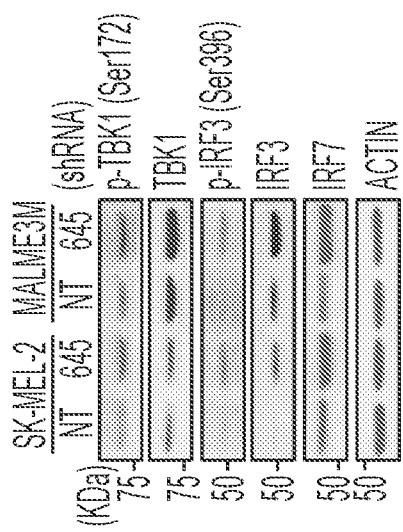

Genes highlighted in red showed increased abundance in SK-MEL-2 cells with the 48-hour treatment of 200 μM NM-350, in comparison with control cells.
Genes highlighted in blue showed reduced abundance in SK-MEL-2 cells with the 48-hour treatment of 200 μM NM-350, in comparison with control cells.
*n.d., non-detectable.
Less than 10% of abundance fold changes in SK-MEL-2 cells with the 48-hour treatment of 200 μM NM-350, in comparison with control cells Using transcriptomic analysis, a group of genes (~750 gene probes corresponding to ~700 genes) were identified that were significantly (P<0.01) and commonly upregulated or downregulated between control and NGLY1-knockdown melanoma cells. The hierarchical clustering of all the cell samples based on the expression of these genes showed that, within the same cell line, all the NGLY1-kockdown samples were similar and segregated from the control samples (FIG. 10A). Data analysis with an additional filtering criterion (expression fold change ≥2) showed that NGLY1 suppression appeared to primarily induce gene upregulation. Many of these upregulated genes, including the IFN #1 and IL-29 genes, are highly associated with cytokine responses in cells (FIG. 10B). The expression of differentially expressed genes was also validated using qRT-PCR (FIG. 10C). In addition to the cytokine signaling-relevant genes, many genes like XAF, ATF3, PMAIP1 (NOXA), AXUD1 and CDKN2C that have been linked to anticancer activity (Bidwell, et al., 2012; Hassan, et al., 2008; Ishiguro, et al., 2001; Jalili, et al., 2012; Reu, et al., 2006; Vert, et al., 2017) were significantly upregulated in the NGLY1-knockdown cells, while genes like FABP7, CRYAB and GAPDHS that have been associated with the survival, proliferation and invasiveness of cancer cells or with a poor prognosis in melanoma patients (Falkenius, et al., 2013; Goplen, et al., 2010; Slipicevic, et al., 2008) were significantly downregulated (Table 4). Ontology analysis showed that ~60 differentially expressed genes (P<0.01, expression fold change ≥2) are highly involved in multiple biological processes (FIG. 10D), including response to stimulus (e.g., immune response and response to stress), metabolic process (e.g., primary metabolic process), and cellular process (e.g., cell communication and cell cycle). In contrast to substantial perturbation induced by NGLY1 knockdown in melanoma transcriptomes, the disruption of NGLY1 expression in normal hPSCs and their differentiated derivatives caused limited changes in their gene expression networks (FIGS. 10E and 10F). None of the differentially expressed genes (P<0.01, expression fold change ≥2) identified in NGLY1-knockdown melanoma cells showed significant expression alterations in NGLY1-deficient hPSCs and their differentiated derivatives, highlighting the fundamental differences of normal and malignant cells in response to NGLY1 inhibition.

TABLE 4

Differentially expressed genes (P < 0.05 & Average fold change ≥ 2) in human melanoma cells with NGLY1 knockdown

| gene probe # | Gene name[a] | Average fold change (log2)[b] | P value |
|---|---|---|---|
| 13 | ATF3 | 1.568 | 0.0016611 |
| 36 | AXUD1 | 1.252 | 0.0004843 |
| 57 | BEX2 | 1.112 | 0.0114698 |
| 51 | BIRC3 | 1.132 | 0.0198327 |
| 6 | CCL5 | 2.125 | 0.0047061 |
| 4 | CCL5 | 2.369 | 0.0012786 |
| 7 | CDCA7 | -1.035 | 0.0046373 |
| 68 | CDKN2C | 1.058 | 0.0276974 |
| 44 | CENTA1 | 1.162 | 0.0010219 |
| 53 | CFB | 1.122 | 0.0392379 |
| 78 | CRYAB | -1.015 | 0.0098900 |
| 65 | DDIT3 | 1.062 | 0.0105068 |
| 56 | DDX58 | 1.113 | 0.0008328 |
| 25 | DHX58 | 1.354 | 0.0000114 |
| 28 | EGR1 | 1.328 | 0.0001190 |
| 38 | EGR2 | 1.223 | 0.0004354 |
| 12 | EPSTI1 | 1.584 | 0.0010029 |
| 48 | FABP7 | -1.133 | 0.0022050 |
| 84 | FOS | 0.999 | 0.0013192 |
| 59 | GAPDHS | -1.101 | 0.0327541 |
| 37 | GBP1 | 1.249 | 0.0014629 |
| 63 | GPM6B | -1.072 | 0.0100371 |
| 1 | HCP5 | 2.630 | 0.0015499 |
| 52 | HERC5 | 1.127 | 0.0000739 |
| 8 | HLA-B | 1.951 | 0.0002007 |
| 30 | HLA-C | 1.303 | 0.0020300 |
| 61 | HLA-F | 1.098 | 0.0114828 |
| 15 | HLA-F | 1.491 | 0.0000087 |
| 43 | HMGCL | 1.174 | 0.0001207 |
| 35 | IFI44 | 1.261 | 0.0000125 |
| 31 | IFI44L | 1.277 | 0.0024527 |
| 18 | IFIH1 | 1.478 | 0.0000116 |
| 49 | IFIT1 | 1.133 | 0.0005623 |
| 29 | IFIT1 | 1.313 | 0.0007546 |
| 7 | IFIT2 | 1.997 | 0.0010418 |
| 10 | IFIT3 | 1.724 | 0.0001275 |
| 9 | IFIT3 | 1.922 | 0.0000341 |
| 23 | IFITM1 | 1.407 | 0.0037163 |
| 2 | IFNB1 | 2.436 | 0.0017186 |
| 27 | IL29 | 1.335 | 0.0054003 |
| 83 | IL8 | 1.002 | 0.0422249 |
| 33 | IRF1 | 1.272 | 0.0039862 |
| 85 | IRF7 | 0.996 | 0.0004498 |
| 46 | IRF7 | 1.154 | 0.0003181 |
| 34 | ISG15 | 1.263 | 0.0003385 |
| 21 | KLF4 | 1.428 | 0.0013494 |
| 41 | LOC100008588 | -1.177 | 0.0371693 |
| 19 | LOC100132564 | 1.475 | 0.0073257 |
| 45 | LOC100133565 | -1.154 | 0.0022528 |
| 17 | NGLY1 | -1.481 | 0.0000005 |
| 26 | OAS1 | 1.338 | 0.0000529 |
| 22 | OAS1 | 1.421 | 0.0000192 |
| 70 | OAS2 | 1.045 | 0.0001903 |
| 54 | OAS2 | 1.119 | 0.0003339 |
| 67 | OAS3 | 1.060 | 0.0001514 |
| 16 | OASL | 1.485 | 0.0005257 |
| 5 | OASL | 2.274 | 0.0000435 |
| 76 | PARP12 | 1.023 | 0.0079003 |
| 58 | PARP9 | 1.101 | 0.0000546 |
| 11 | PMAIP1 | 1.660 | 0.0006323 |
| 39 | PSMB9 | 1.213 | 0.0049945 |
| 24 | PTGS2 | 1.394 | 0.0099303 |
| 77 | RARRES3 | 1.022 | 0.0000657 |
| 32 | RN5S9 | 1.274 | 0.0325331 |
| 3 | RSAD2 | 2.411 | 0.0000004 |
| 71 | RTP4 | 1.045 | 0.0002050 |
| 62 | SAMD9 | 1.078 | 0.0005239 |
| 40 | SAMD9L | 1.204 | 0.0020208 |
| 81 | SEMA5A | -1.006 | 0.0287923 |
| 55 | SERTAD1 | 1.117 | 0.0013974 |
| 14 | SLC15A3 | 1.500 | 0.0004396 |
| 86 | SP110 | 0.996 | 0.0000227 |
| 69 | SP110 | 1.050 | 0.0000635 |
| 42 | SP110 | 1.175 | 0.0000145 |
| 72 | TAP1 | 1.038 | 0.0001089 |
| 64 | TMEM140 | 1.068 | 0.0029536 |
| 73 | TNFRSF12A | 1.037 | 0.0453292 |
| 66 | TNFSF10 | 1.061 | 0.0145028 |
| 50 | TRIM22 | 1.133 | 0.0020824 |
| 47 | USP18 | 1.150 | 0.0001262 |
| 75 | XAF1 | 1.033 | 0.0028008 |
| 20 | XAF1 | 1.447 | 0.0000637 |
| 79 | ZC3HAV1 | 1.015 | 0.0002501 |
| 60 | ZC3HAV1 | 1.100 | 0.0000965 |
| 80 | ZNFX1 | 1.011 | 0.0001059 |

[a] The upregulation of underlined genes was observed in human melanoma cells in response to IL-29 treatment (Guenterberg, et al., 2010). The expression of genes in italics previously have been liked to anticancer activity (e.g., cell cycle arrest, apoptosis, or mobility suppression in cancer cells), while the expression of genes in bold have been associated with the survival, proliferation and invasiveness of cancer cells or with a poor prognosis in melanoma patients.
[b] Positive values indicate expression changes in upregulation. Negative values indicate expression changes in downregulation.

Example 6—Combinatorial Approaches to Eliminate Melanoma Cells by Targeting NGLY1

Despite the frequent failure of chemotherapy in patients with melanoma, chemotherapy remains a frontline approach for treatment, especially in many patients who cannot afford immunotherapy or targeted therapy. In addition, patients presenting with significant tumor regression following the initial treatment of targeted therapies like vemurafenib do not always maintain long-term disease remission. Identifying novel approaches to enhance the efficacy of chemotherapy and targeted therapy agents in melanoma will greatly benefit many cancer patients. Having agents that synergize with NGLY1 suppression to eliminate cancer cells also helps to reduce the effective dose and extend the application of novel NGLY1-targeting strategies that wait to be developed for cancer treatment. In addition, these agents may have a great use for preventing or overcoming cancer cells that eventually develop resistance to NGLY1 suppression. Cisplatin and dacarbazine have been tested as representative chemotherapy agents since they have been commonly used for the treatment of patients with metastatic melanoma (www.uptodate.com/contents/cytotoxic-chemotherapy-for-metastatic-melanoma). The stable clones of melanoma cells with inducible NGLY1 shRNA and without dox induction were treated with cisplatin and dacarbazine at doses of 0-160 µM. To determine the $IC_{50}$ of each drug in each stable clone, cells seeded into 96-well plates and treated with drugs for 72 hours was subjected to MTT assays. The $IC_{50}$ of each drug treatment in each cell clone was calculated using CalcuSyn 2.0. Test results revealed that UACC257 and MALME3M cells showed moderate growth inhibition without increase of cell death after the 72-hour treatment of 20 µM cisplatin and dacarbazine, suggesting that UACC257 and MALME3M cells present certain resistance to these chemotherapy agents.

To determine the $IC_{50}$ of each drug in each stable clone, cells seeded into 96-well plates and treated with drugs for 72 hours was subjected to MTT assays. The dose effect of dox-induced expression of NGLY1 shRNA in each cell clone was also determined. The $IC_{50}$ of each drug treatment in each cell clone was calculated using CalcuSyn 2.0. To determine the interaction between NGLY1 knockdown and each anticancer agent, cells were exposed to four-dose combinations of dox and an anticancer agent at a fixed dose ratio. The combination index (CI) value was calculated using CalcuSyn 2.0. CI values of less than 1 are considered a synergistic interaction. CI values equal to and larger than 1 are considered additive and antagonistic effects, respectively.

Figure 5F:
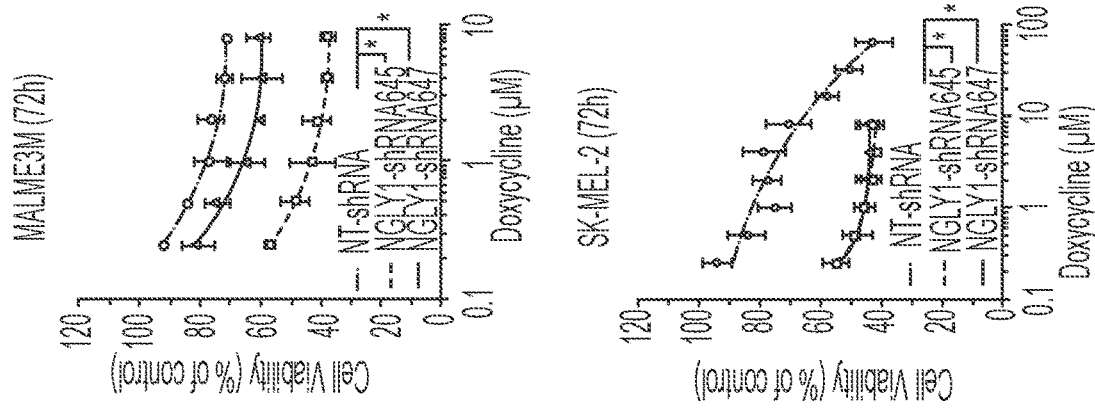
Figure 5F:
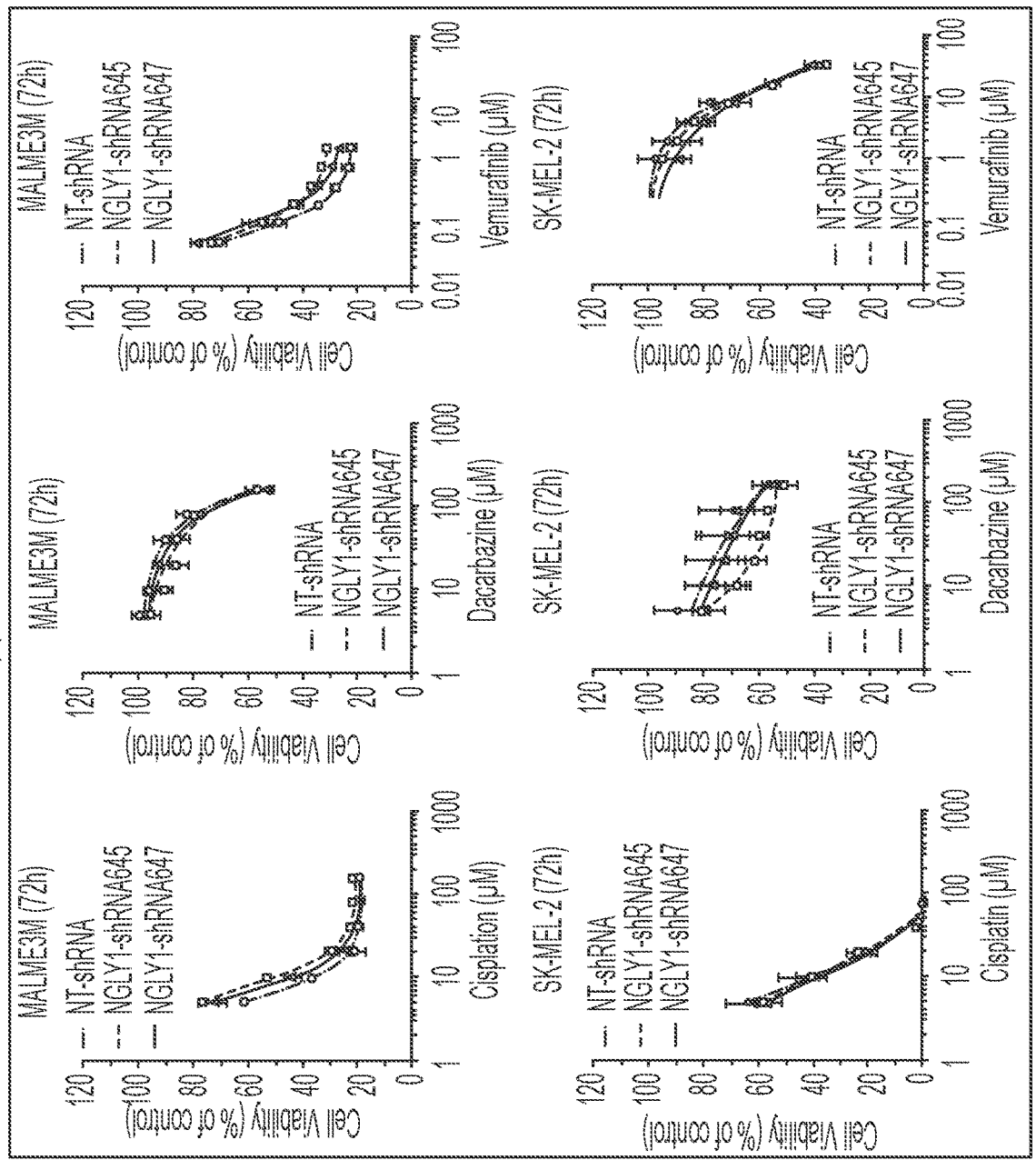
Figure 5G:
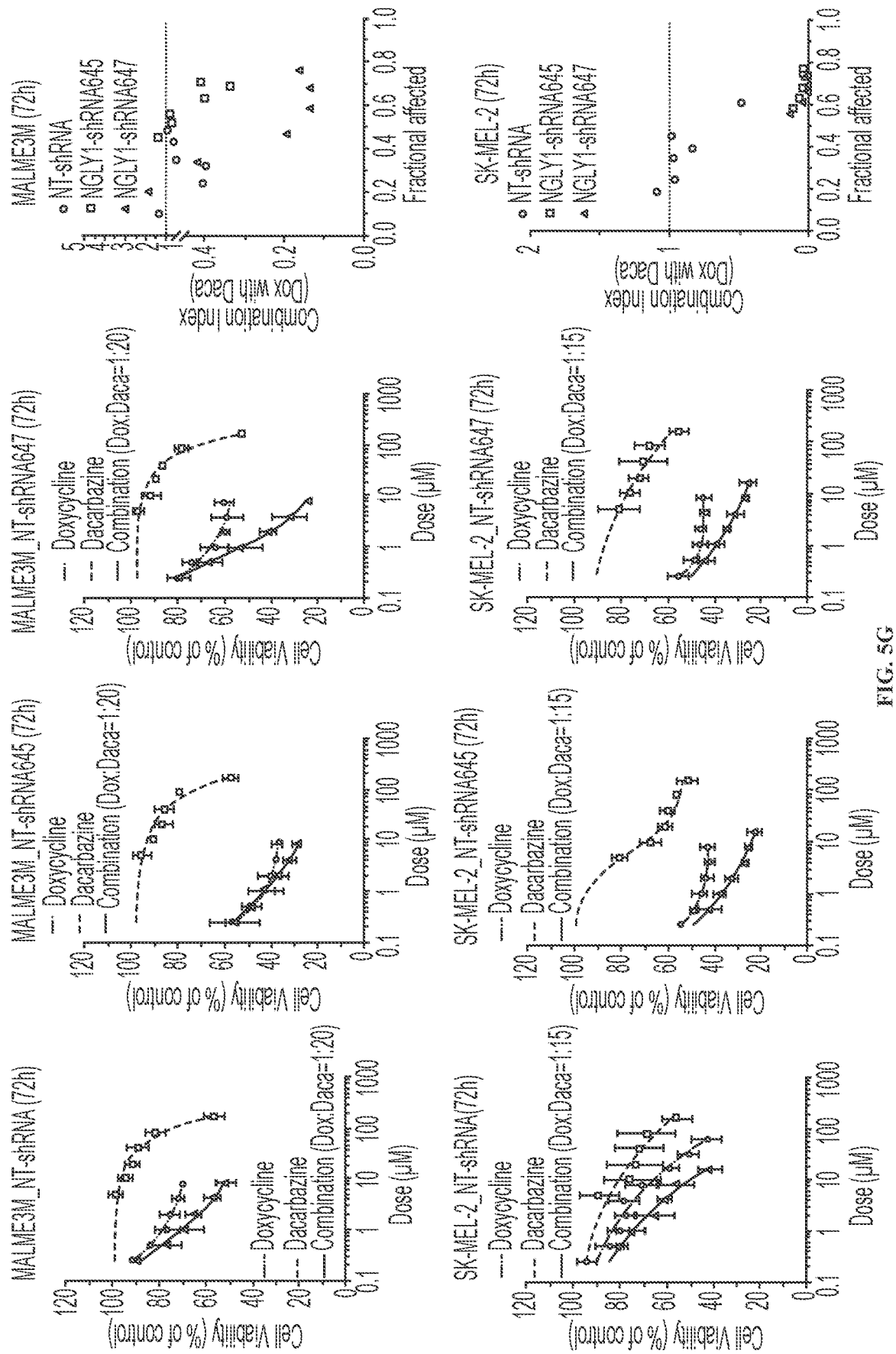
Figure 12:
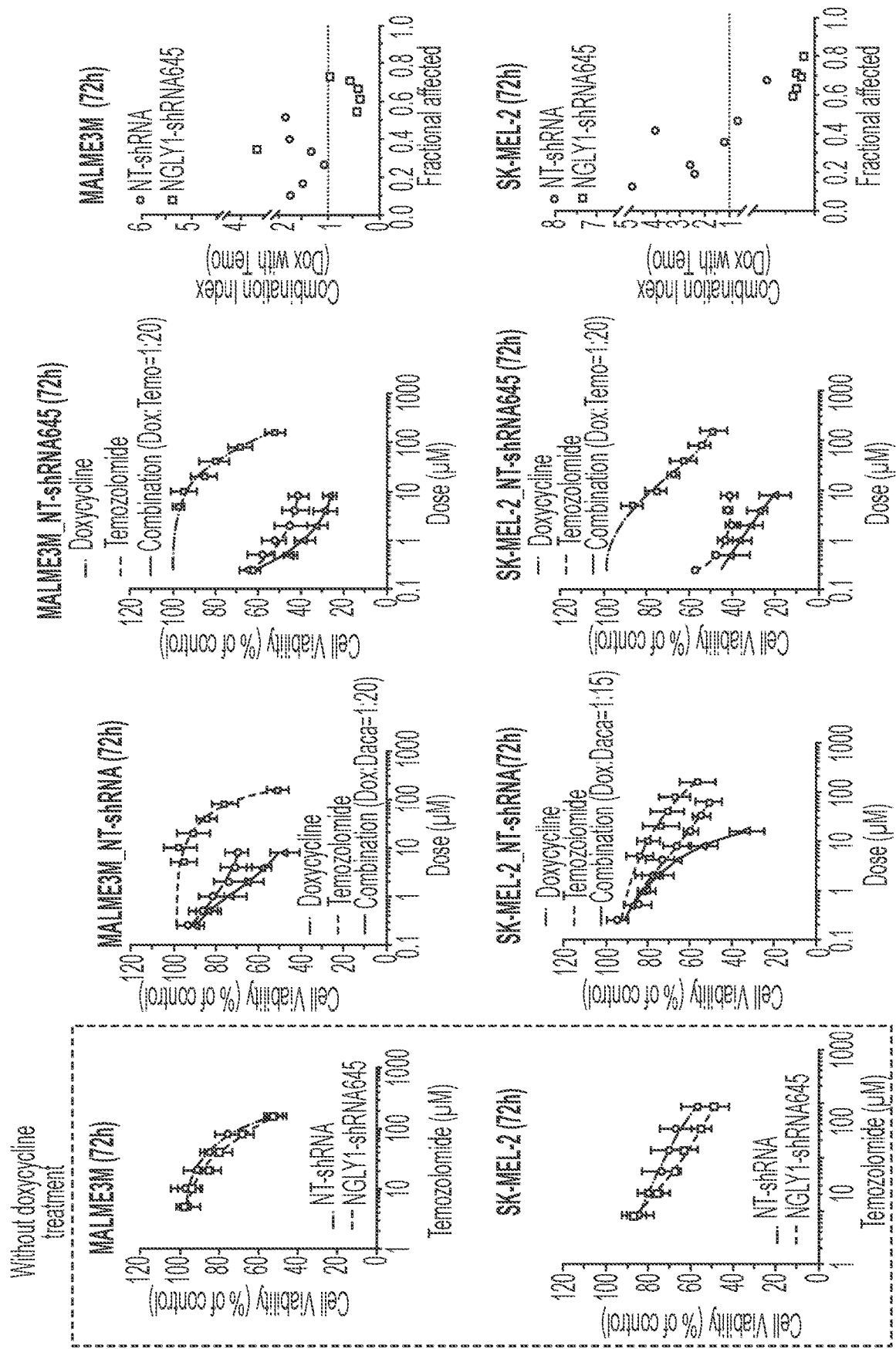
FIG. 12 shows the synergistic anticancer responses of NGLY1 knockdown and temozolomide treatment in MALME3M and SK-MEL-2 melanoma cells. The calculation of combination indexes was performed using Calcusyn software. A combination index value <1 was considered synergistic. A combination index value <0.2 was considered highly synergistic. All cell viability data were presented as mean±standard deviation (n=3).

Unlike the treatment of an ER stress inducer, tunicamycin, NGLY1 knockdown activates apoptotic factors like ATF4 and GADD153 without upregulating ER chaperones GRP78/94 (FIG. 5C). Many chemotherapeutic drugs including DNA alkylating agents also induce GADD153 in cancer cells (Luethy and Holbrook, 1992). Thus, NGLY1 suppression may synergize with DNA alkylating agents like dacarbazine and temozolomide to eliminate melanoma cells, at least partially, through intensified activation of GADD153. It was also tested whether NGLY1 suppression enhances the anticancer activity of dacarbazine and temozolomide that are commonly used to treat melanoma. Unlike MALME3M cells with the $BRAF^{V600E}$ mutation and high sensitivity to vemurafenib (Yang, et al., 2010), SK-MEL-2 cells with the $NRAS^{Q61R}$ mutation (Yang, et al., 2010) are resistant to vemurafenib (FIG. 5F). The knockdown of NGLY1 compromised the viability of MALME3M and SK-MEL-2 cells (FIG. 5F) in viability assays where we also observed a highly synergistic effect of NGLY1 knockdown in combination with the cytotoxicity of either dacarbazine or temozolomide (FIG. 5G; FIG. 12). These results indicate that the suppression of NGLY1 could overcome melanoma cells with resistance to BRAF inhibitors as well as sensitize the cells to conventional chemotherapy agents that frequently lead to unsatisfactory outcomes in the treatment of patients with melanoma. A similar synergistic effect may also exist in other chemotherapy-insensitive melanoma cells such as UACC257 cells and can be further exploited for a significant advantage in therapy.

Figure 13:
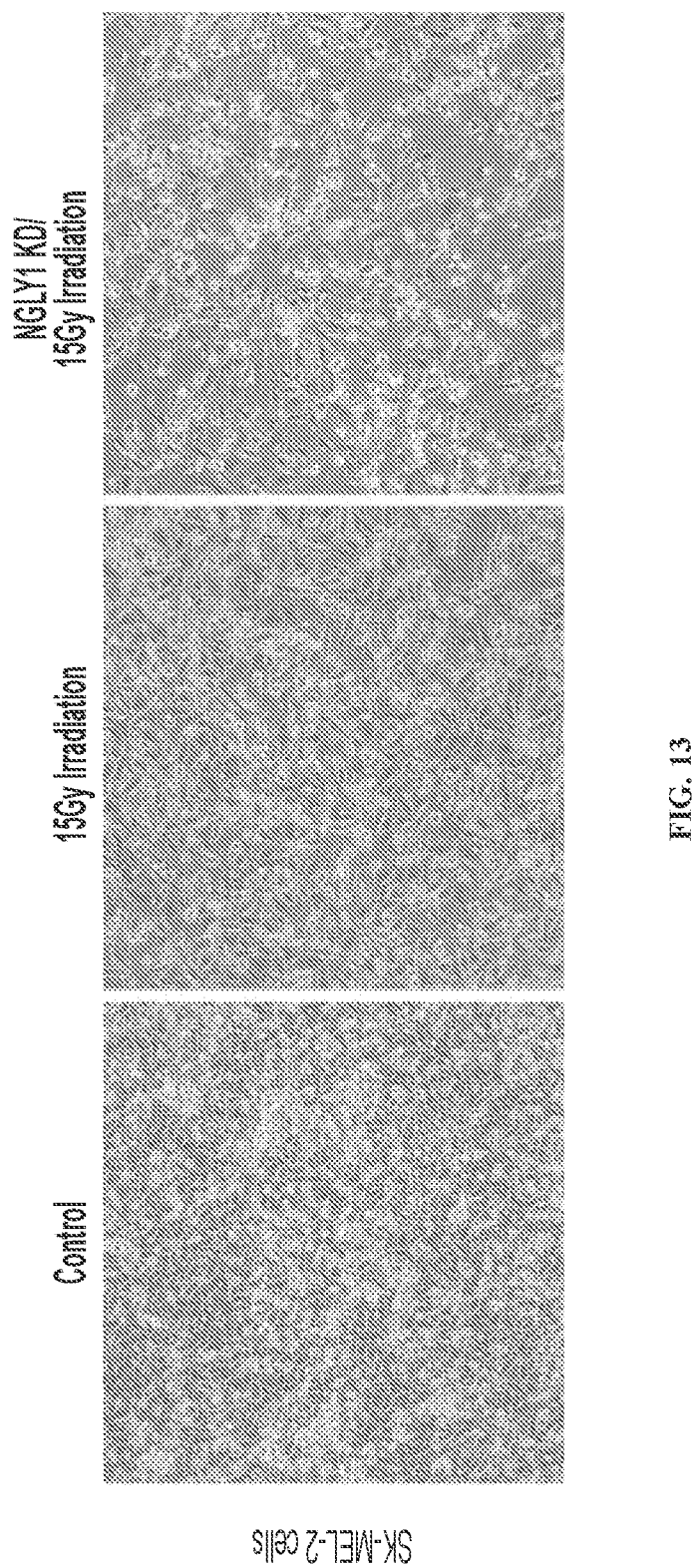
FIG. 13 shows SK-MEL-2 melanoma cells with inducible NGLY1-targeting shRNA showed enhanced apoptosis (cell death) in response to the knockdown of NGLY1 followed by 15Gy X-ray irradiation. Forty-eight hours prior to irradiation, cells (2×10$^5$/well) were seeded into culture plates. Twenty-four hours prior to irradiation, shRNA-mediated NGLY1 knockdown was induced. Seventy-two hours after irradiation, images of the cell morphology were taken. Control cells received neither the induction of NGLY1 knockdown nor irradiation.

Additionally, the suppression of NGLY1 can sensitize cancer cells to X-ray irradiation as shown in FIG. 13. SK-MEL-2 melanoma cells with inducible NGLY1-targeting shRNA showed enhanced apoptosis (cell death) in response to the knockdown of NGLY1 followed by 15Gy X-ray irradiation. Forty-eight hours prior to irradiation, cells ($2\times10^5$/well) were seeded into culture plates. Twenty-four hours prior to irradiation, shRNA-mediated NGLY1 knockdown was induced. Seventy-two hours after irradiation, images of the cell morphology were taken. Control cells received neither the induction of NGLY1 knockdown nor irradiation. These data suggest that the combination of X-ray irradiation with NGLY1 inhibition can lead to synergistic effects.

Example 7—NGLY1 Inhibition in Melanoma Tumors and Novel NGLY1 Inhibitors

Figure 14A:
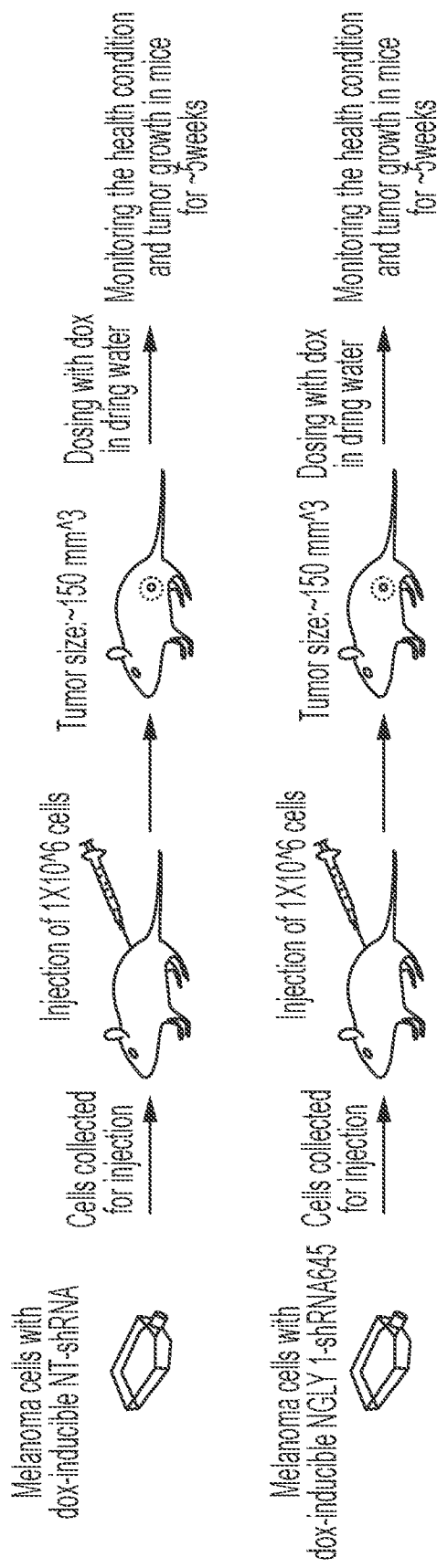
FIGS. 14A-14D shows the in vivo antitumor activity of targeting NGLY1 in melanoma cells.
Figure 14B:
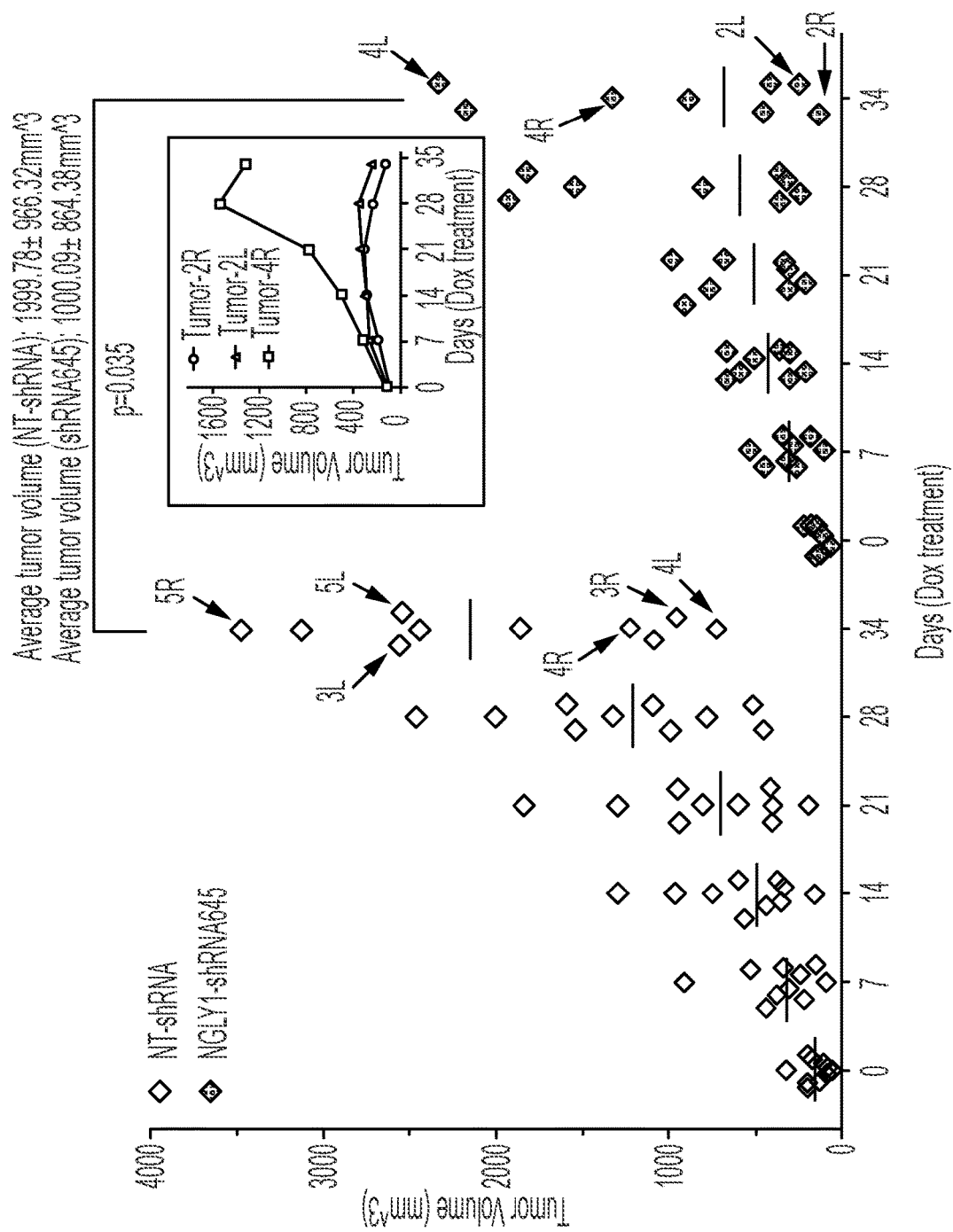
Figure 14C:
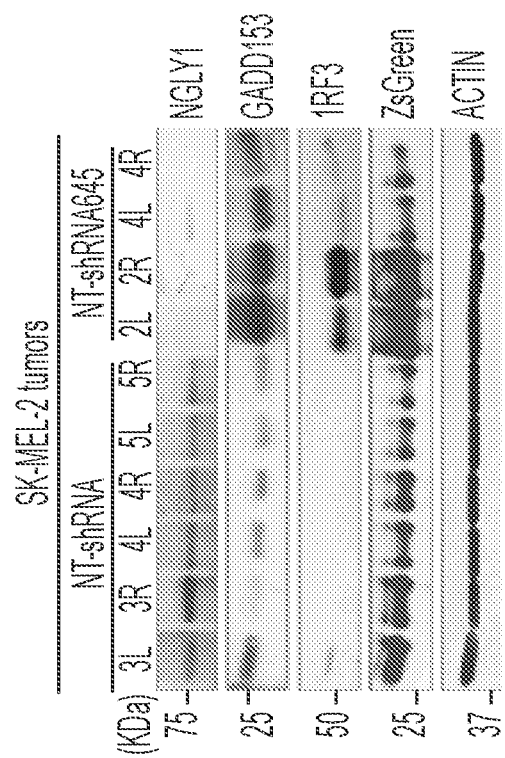
Figure 14D:
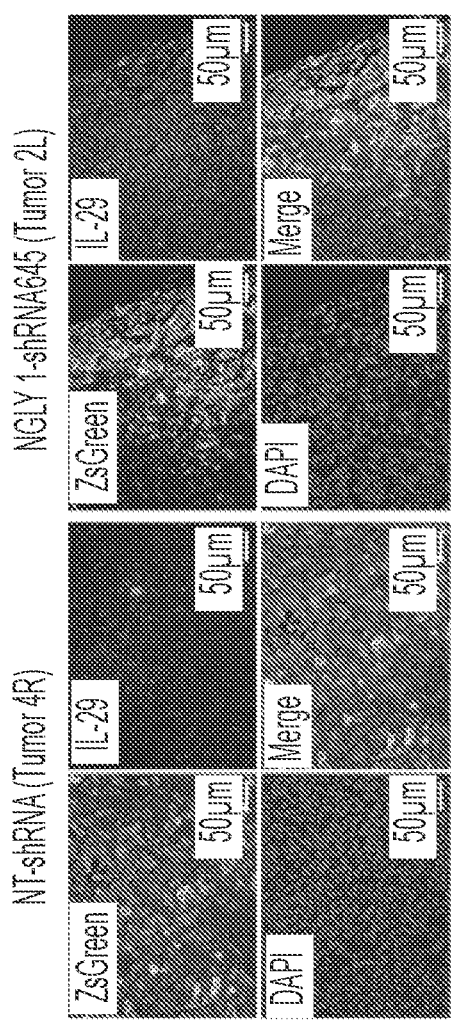

Using a xenograft tumor model (FIG. 14A), the anti-melanoma response of NGLY1 suppression was tested. The growth of melanoma tumors established with SK-MEL-2 cells in mice was impeded by the induced knockdown of NGLY1 (FIGS. 14B and 14C). It was also noticed that three out of eight tumors with NGLY1-targeting shRNA that increased their size during the initial 3-4 weeks of dox treatment showed regression at the end of the study (FIG. 14B, inset). The enhanced expression of GADD153, IRF3 and IL-29 was also detected in the NGLY1-knockdown tumors (FIGS. 14C and 14D). These findings attest to the in vivo antitumor efficacy of NGLY1 inhibition that was expected from our in vitro studies.

Figure 15A:
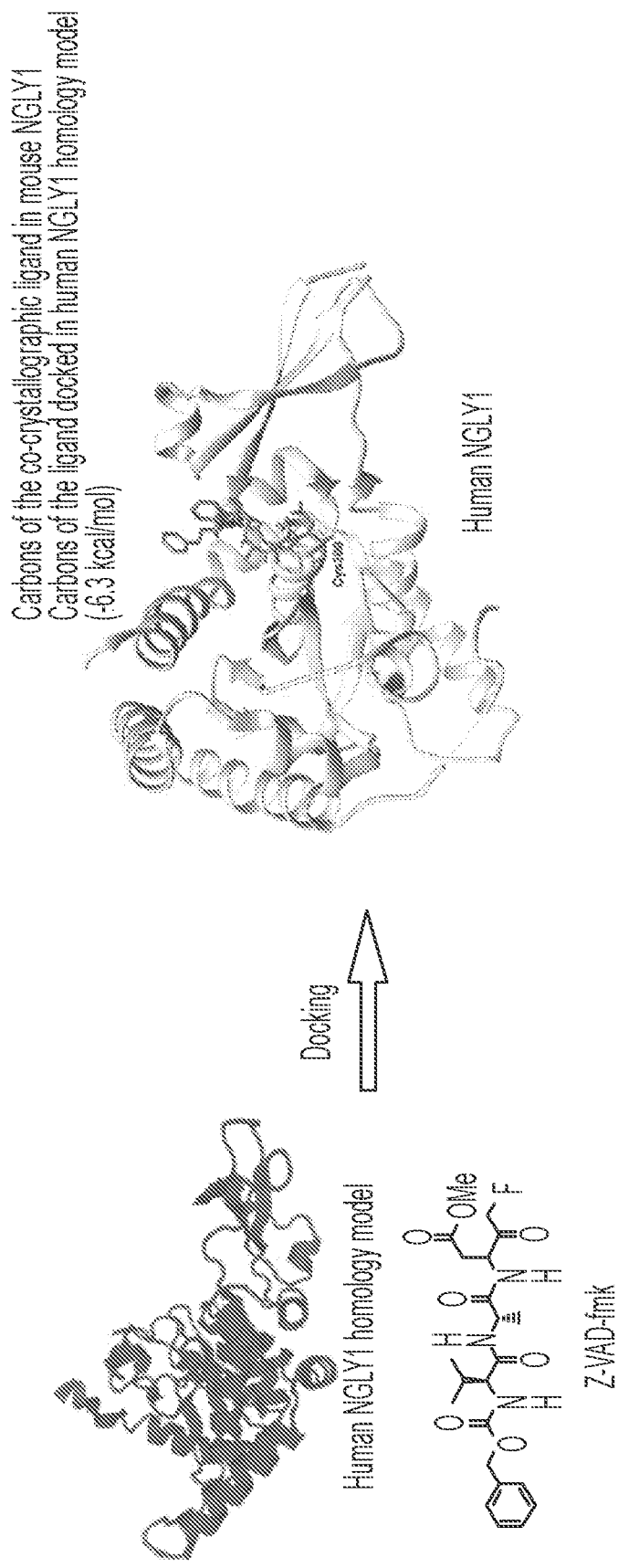
FIGS. 15A-15F shows anticancer responses induced by novel covalent modifiers that target the catalytic site of human NGLY1 in melanoma cells. The computational homology model of human NGLY1 core domain was generated and used for studying interactions between NGLY1 and novel small molecules that are designed to covalently modified and inactivate the catalytic site of NGLY1.
Figure 15B:
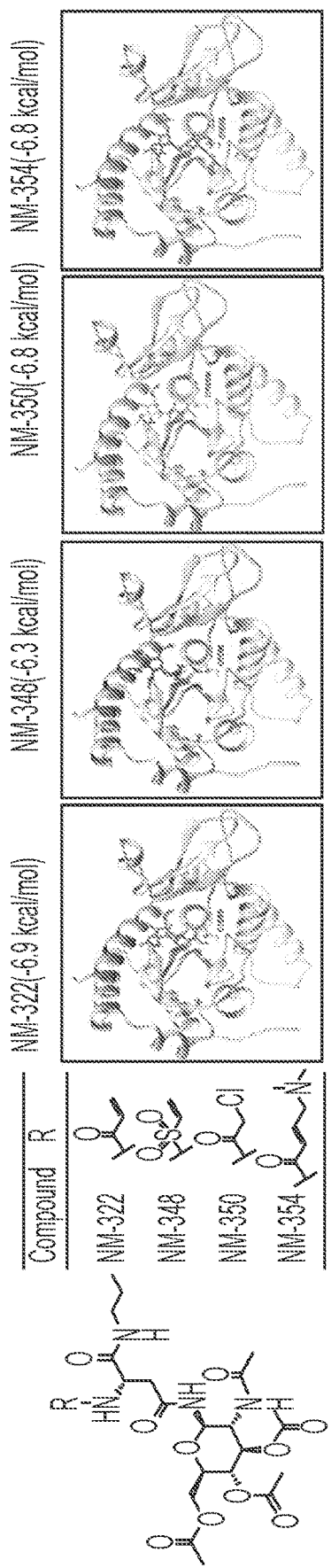

Due to the lack of optimized small molecules that specifically inactivate human NGLY1, additional NGLY1 inhibitors were developed and test their potential anti-melanoma use. Based on the crystal structure of mouse NGLY1 [PDB code: 2F4M, (Zhao, et al., 2006)] as a model-building template, a homology model of the human NGLY1 core domain (FIG. 15A) was built using a homology-modeling web server SWISS-MODEL. To test the human NGLY1 homology model, we used it to perform in silico docking analysis of known molecules that may inactivate human NGLY1. Since Z-VAD-fmk (a benzyloxycarbonyl-Val-Ala-Asp tripeptide with fluoromethyl group at the C-terminal) penetrates cells and reacts with yeast, mouse and human NGLY1 (Misaghi, et al., 2004; Tomlin, et al., 2017; Zhao, et al., 2006) by forming a covalent bond with the cysteine residues at the catalytic sites (e.g., Cys309 in human NGLY1), Z-VAD-fmk was docked to the human NGLY1 homology model using AutoDock. As expected, the top-scored binding poses of Z-VAD-fmk in the homology model include the ones that are similar to the binding pose in the crystal structure of a mouse NGLY1 and Z-VAD-fmk complex (PDB code: 2F4O; FIG. 15B), indicating that Z-VAD-fmk can bind to and inactivate the catalytic site of human NGLY1 in a similar fashion. This result also supports the accuracy and suitability of our NGLY1 homology model for inhibitor screening.

Figure 15C:
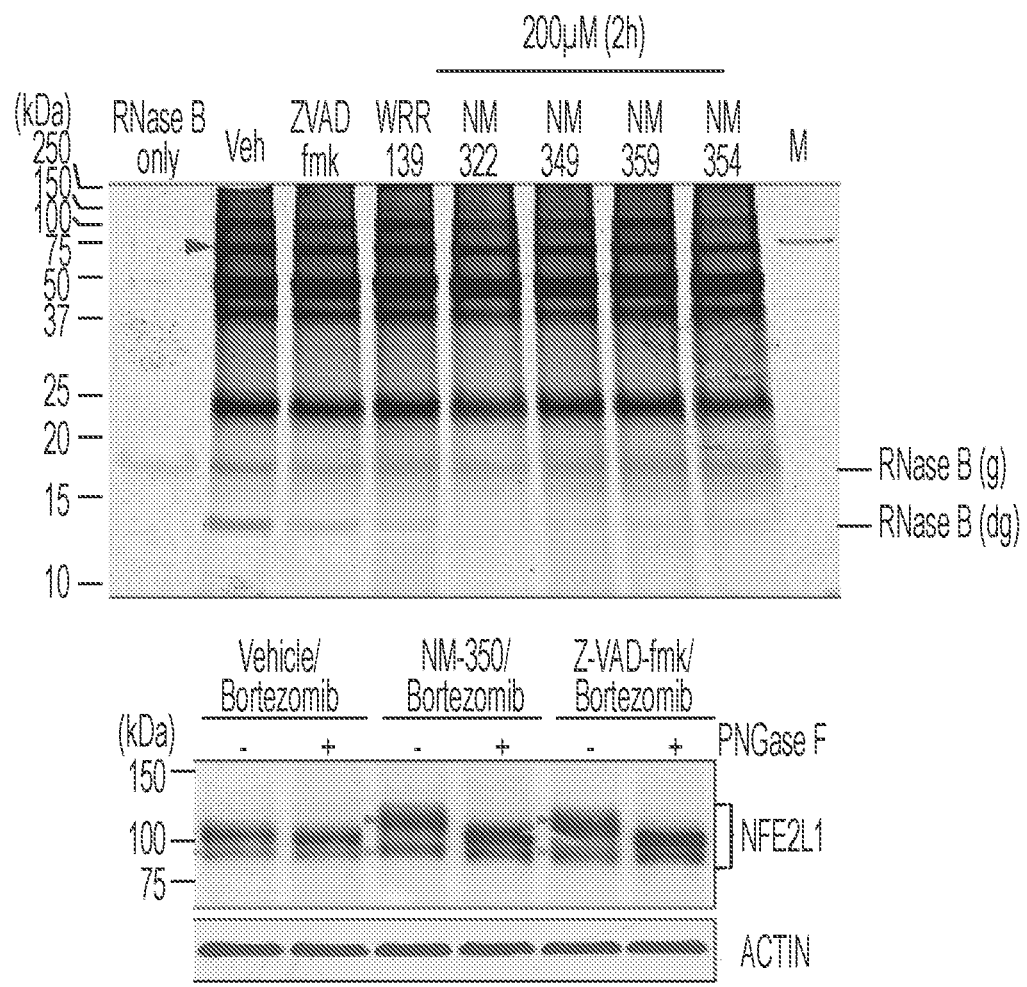

Four small molecules (NM-322, NM-348, NM-350 and NM-354) were designed that mimiced the N-acetylglucosamine (GlcNAc)-linked asparagine substrates of NGLY1 and contained strategically positioned electrophilic groups (FIG. 15B). Their preferred binding poses in the human NGLY1 homology model included catalytic poses where the electrophilic reactive moieties of compounds were oriented toward Cys309. The binding energy of these compounds in their most favorable catalytic poses ranged from −6.3 to ~6.9 kcal/mol. Since the binding energy of the most favorable binding pose of Z-VAD-fmk in the homology model was estimated as −6.3 kcal/mol, considering the ±2.0 kcal/mol variation of binding energy calculation in AutoDock, it is believable that our novel compounds could have comparable inhibitory activity towards human NGLY1 as Z-VAD-fmk. Like Z-VAD-fmk and WRR139 (Tomlin, et al., 2017), our compounds caused NGLY1 inhibition and blocked the deglycosylation of denatured RNase B in vitro (FIG. 15C, upper panel). Since NGLY1 inactivation hinders the deglycosylation and proteolytic processing of NFE2L1 (Tomlin, et al., 2017) in proteasome inhibitor-treated cells, the inhibitors were tested and may interfere with NFE2L1 deglycosylation. HEK293T cells (a sub-clone of HEK293 cells) were used in this test because HEK293 cells have been used in a similar study and appear to tolerate NGLY1 suppression well (Tomlin, et al., 2017). HEK293T cells pretreated with NM-350 showed clear retention of N-glycans on NFE2L1, indicated by the electrophoretic mobility shift of full-length NFE2L1 (FIG. 15C, lower panel).

Figure 15D:
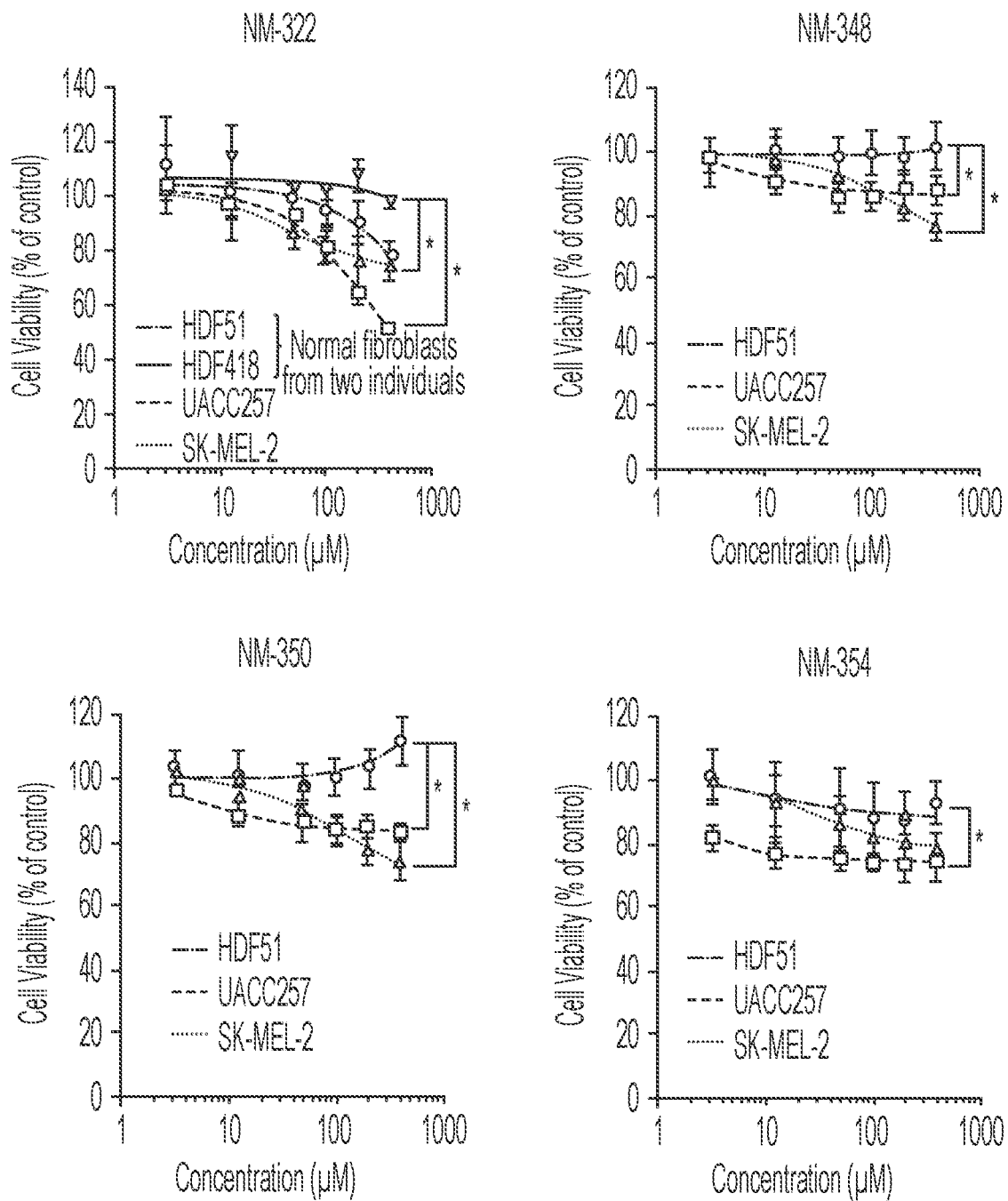
Figure 15E:
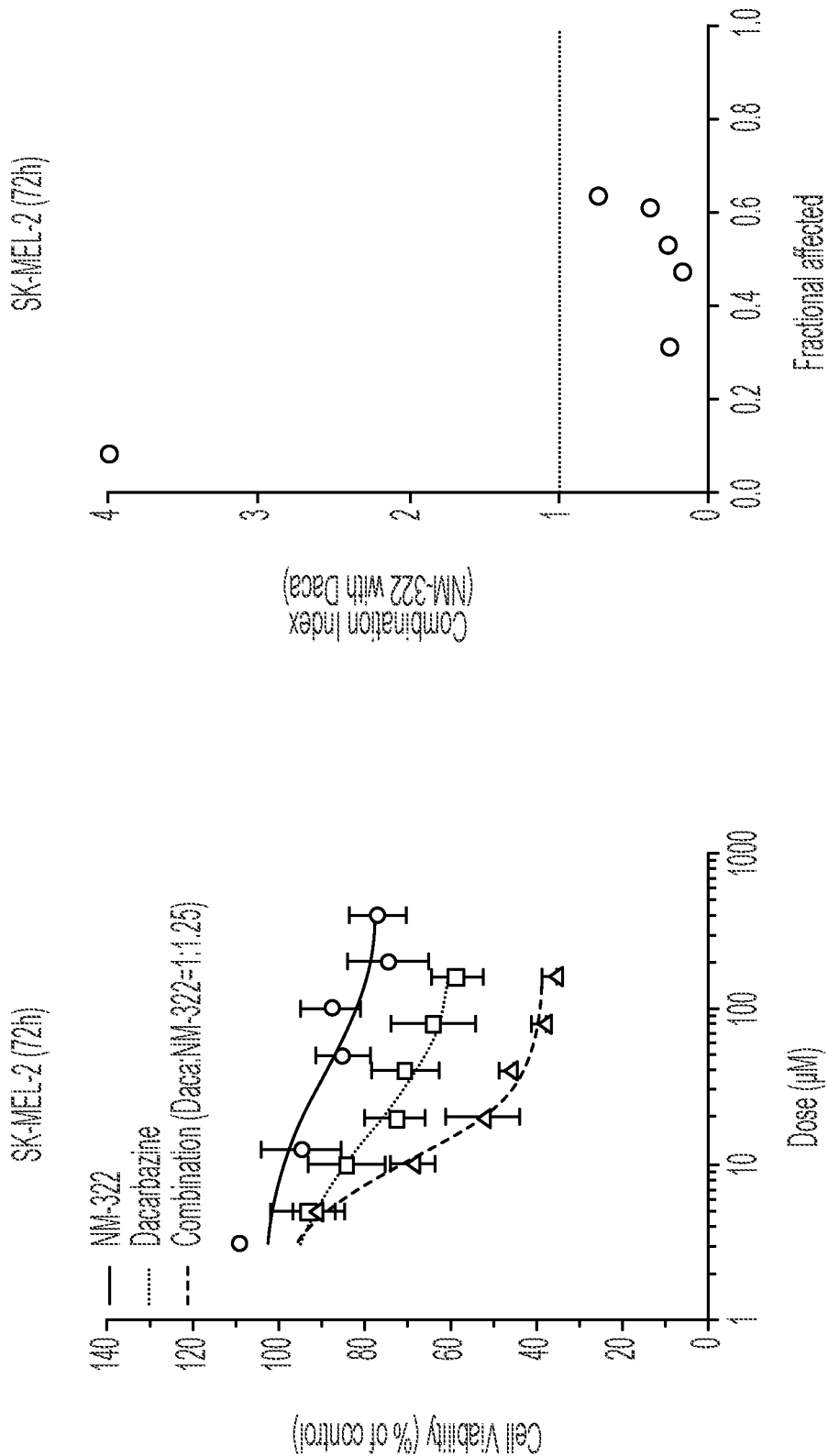
Figure 15F:
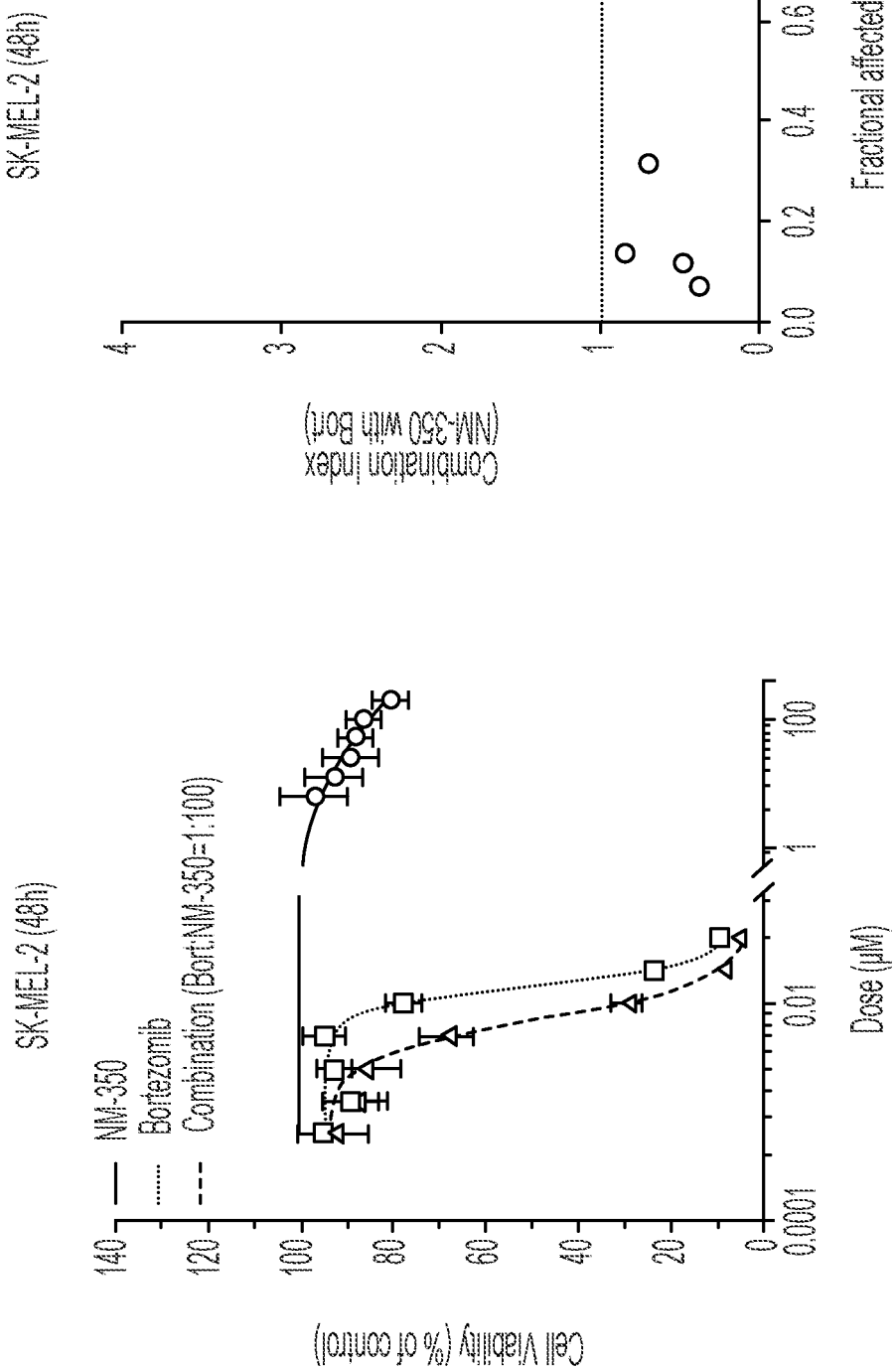

As shown in FIG. 15D, the new compounds preferentially inhibited melanoma cell viability and had limited impact on normal cells. The treatment of the inhibitors also enhanced the production and release of IFNβ and IL-29 in melanoma cells but not normal cells (FIG. 16A). Similar to the synergism between NGLY1 knockdown and dacarbazine treatment, NM-322 and dacarbazine caused a synergistic effect on the suppression of SK-MEL-2 cells (FIG. 15E). Consistent with the potentiation of proteasome inhibitor cytotoxicity caused by WRR139-mediated NGLY1 inhibition (Tomlin, et al., 2017), NM-350 and bortezomib synergistically suppressed the viability of SK-MEL-2 cells (FIG. 15F). These results highlight that pharmacological inactivation of NGLY1 reduces melanoma cell viability and can be exploited for cancer therapy purposes.

Having elevated contents of GlcNAc-asparagine-containing peptides and the differential abundance of specific proteins detected in NGLY1-knockdown melanoma cells (FIG. 7; Table 3), proteomic changes in melanoma cells treated with our NGLY1 inhibitors were examined. Like the NGLY1-knockdown cells, cells treated with the inhibitors showed relatively high contents of GlcNAc-asparagine-containing peptides (FIG. 16B), suggesting that the inhibitors are likely to suppress NGLY1 activity and allow ENGase to generate more enzymatic products with the GlcNAc-asparagine signature. Similar alteration patterns associated with the differentially abundant proteins identified in the NGLY1-knockdown cells were observed in melanoma cells treated with NM-350 (Table 3), further supporting the NGLY1-inhibitory and anticancer activity of the compounds.

Example 8—NGLY1 Inhibition in Non-Melanoma Cancers

Figure 17A:
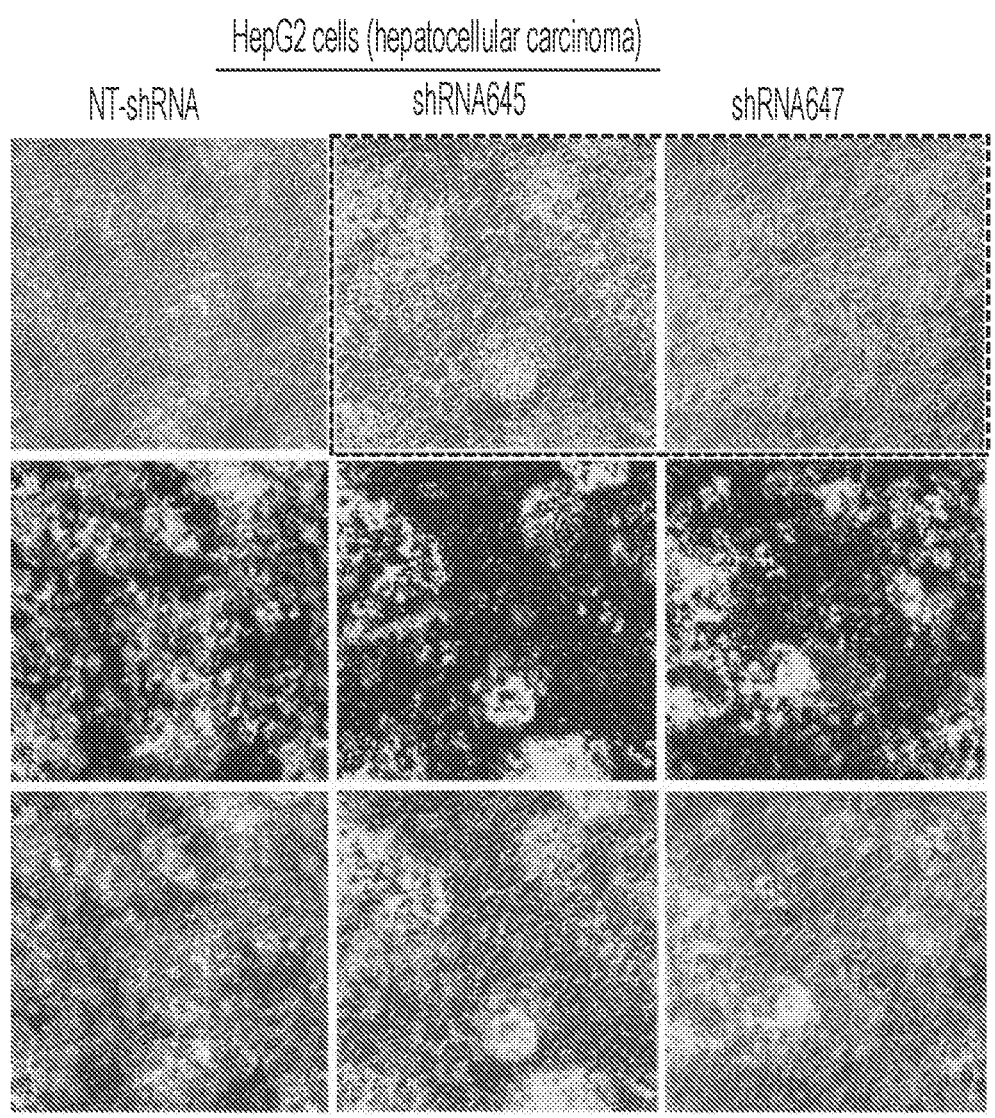
FIGS. 17A & 17B show (FIG. 17A) HepG2 liver cancer cells showed a morphology of apoptosis (cell death) in response to the knockdown of NGLY1 (NT-shRNA: non-targeting shRNA; shRNA645 and shRNA647: two NGLY1-targeting shRNA sequences).
Figure 17B:
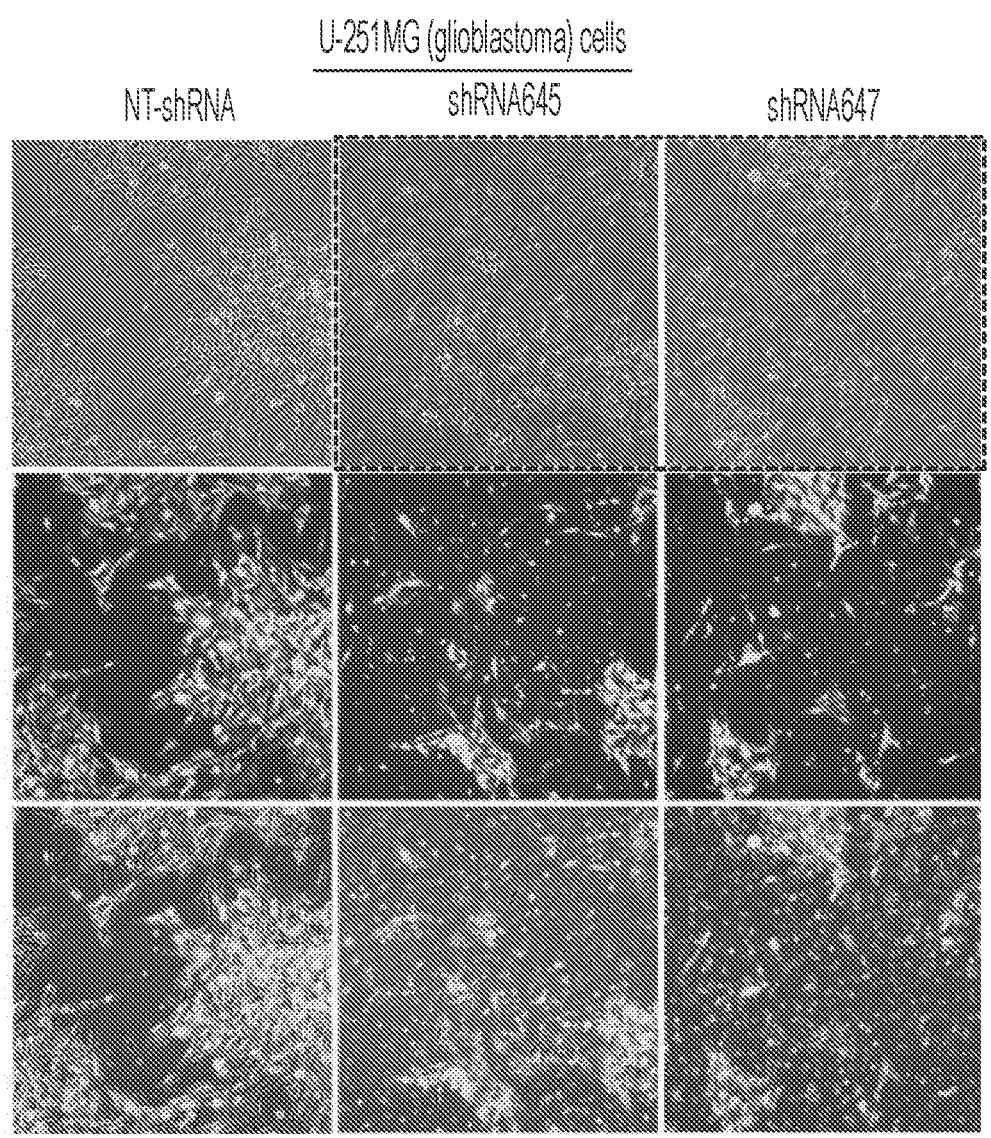

As shown in FIG. 17A & 17B, inhibition of NGLY1 is sufficient to induce cell death in HepG2 cells (a model of hepatocellular carcinoma) and U-251MG cells (a model of glioblastoma).

Figure 18:
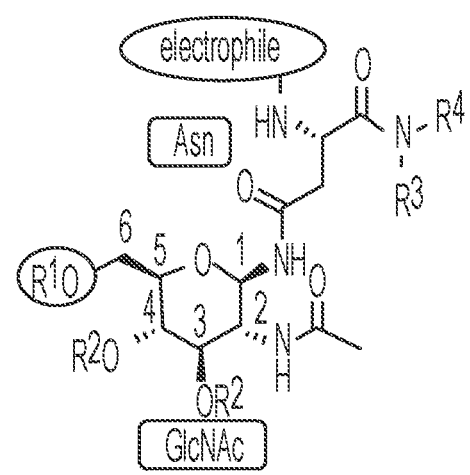
FIG. 18 shows general concept for the design of irreversible inhibitors of NGLY1. Electrophile: electrophilic group; Asn: asparagine subunit; GlcNAc: N-acetylglucoasmine subunit; $R^1$, $R^3$, and $R^4$: sites for modification.

Example 9—the Design of Small-Molecule Inhibitors that Specifically Inactivate NGLY1 Activity in Human Cells Since NGLY1 cleaves the amide bond between an asparagine (Asn) residue of an N-glycoprotein and an N-acetylglucosamine (GleNAc) group, the design of synthetic analogs that maintain these residues within the core structure is a logical starting point (FIG. 18). It is contemplated to prepare derivatives at the Asn amine that contain electrophilic moieties capable of reacting with Cys[309] of human NGLY1. The design of small molecule inhibitors that form covalent bonds with reactive cysteine residues is a well-documented strategy in cancer drug discovery (Liu et al., 2013). Moreover, it has been estimated that of all enzyme targets with an associated FDA approved drug, approximately one-third have an example of at least one approved therapeutic that acts via an irreversible mechanism (Singh et al., 2011).

Example 10—Synthesis of Compounds

A robust and economical synthesis of the requisite precursors to our target analogs was developed as described below.

Synthesis and Purification.

Air sensitive reactions were carried out under a nitrogen atmosphere (Airgas Catalog No. NI UHP300). The following solvents were employed for chemical reactions: dichloromethane (99.9%, Extra Dry, AcroSeal™, Acros Organics Catalog No. 610300010), N,N-dimethylformamide (Anhydrous, 99.8%, packaged under Argon in resealable Chem-Seal™ bottles, Catalog No. 43997) and ethyl alcohol (Absolute, anhydrous, ACS/USP grade, Pharmco-AAPER Catalog No. 111000200). The following solvents were employed for compound extractions: ethyl acetate (Certified ACS grade, Fisher Chemical Catalog No. E145-20) and dichloromethane (Not Stabilized, HPLC grade, Fisher Chemical Catalog No. D150-4). Saturated aqueous $NaHCO_3$ was prepared from deionized water and sodium bicarbonate (Reagent grade, Fisher Chemical Catalog No. S25533B). Brine was prepared from deionized water and sodium chloride (Reagent grade, Fisher Chemical Catalog No. S25541B). Organic extracts were dried over anhydrous sodium sulfate (Lab grade, Fisher Chemical Catalog No. S25568A). Thin layer chromatography (TLC) was conducted on glass plates coated with Silica Gel 60 $F_{254}$ from Millipore Sigma (Catalog No. 1057150001). Normal phase flash chromatography was carried out on either a CombiFlash® EZ Prep or CombiFlash® Rf+ automated flash chromatography system, both from Teledyne ISCO. Normal phase flash chromatography was carried out using RediSep® Rf normal phase disposable flash columns (40-60 micron) from Teledyne ISCO (Catalog Nos. 69-2203-304, 69-2203-312, 69-2203-324, 69-2203-340, 69-2203-380, and 69-2203-320). The following solvents were employed for TLC and normal phase chromatography: hexanes (Certified ACS grade, Fisher Chemical Catalog No. H292-20), ethyl acetate (Certified ACS grade, Fisher Chemical Catalog No. E145-20), dichloromethane (Not Stabilized, HPLC grade, Fisher Chemical Catalog No. D150-4), and methanol (HPLC grade, Fisher Chemical, Catalog No. A452-4). Reverse phase chromatography was carried out on a CombiFlash® EZ Prep automated flash chromatography system using a RediSep® Rf C18 column from Teledyne ISCO (Catalog No. 69-2203-413). Reverse phase preparative HPLC was carried out on a CombiFlash® EZ Prep automated flash chromatography system equipped with a RediSep® Prep C18 10×250 mm, 100 Å, 5 µm HPLC preparative column from Teledyne ISCO (Catalog No. 692203809). The following solvents were employed for reverse phase chromatography: acetonitrile (HPLC grade, Fisher Chemical Catalog No. A998SK-4) and water purified using a Milli-Q® Advantage A10 Water Purification System from Millipore Sigma.

Characterization.

All NMR spectra were recorded on a 300 MHz Bruker Fourier 300HD NMR spectrometer equipped with a dual $^1H$ and $^{13}C$ probe with Z-Gradient and automatic tuning and matching, full computer control of all shims with Top-Shim™, 24-sample SampleCase™ automation system, and TopSpin™ software. All NMR samples were prepared with either methyl sulfoxide-$d_6$ with 0.03% TMS, 99.8 atom % D, Acros Organics Catalog No. 360000100) or chloroform-d with 0.03% TMS, 99.8+ atom % D, Acros Organics Catalog No. 209561000). $^1H$ and $^{13}C$ chemical shifts are reported in δ values in ppm downfield with tetramethylsilane (TMS) as the internal standard. Data are reported as follows: chemical shift, multiplicity (s=singlet, d=doublet, t=triplet, q=quartet, b=broad, m=multiplet), integration, coupling constant (Hz). High resolution mass spectrometry was conducted on an Agilent 6230 Accurate-Mass Time-of-Flight (TOF) LC/MS with ESI source equipped with MassHunter Walkup software. MS parameters were as follows: fragmentor: 175 V, capillary voltage: 3500 V, nebulizer pressure: 35 psig, drying gas flow: 11 L/min, drying gas temperature: 325° C. Samples were introduced via an Agilent 1260 Infinity UHPLC comprised of a G4225A HiP Degasser, G1312B binary pump, G1367E ALS, G1316A TCC, and G1315C DAD VL+ with a 5 µL semi-micro flow cell with a 6 mm path length. UV absorption was observed at 220 nm and 254 nm with a 4 nm bandwidth. Column: Agilent Zorbax SB-C18, Rapid Resolution HT, 1.8 μm, 2.1×50 mm. Gradient conditions: Hold at 5% CH$_3$CN in H$_2$O (0.1% formic acid) for 1.0 min, 5% to 95% CH$_3$CN in H$_2$O (0.1% formic acid) over 5 min, hold at 95% CH$_3$CN in H$_2$O (0.1% formic acid) for 1.0 min, 0.5 mL/min. All analogs were at least 95% pure according to these analytical methods.

Synthesis of Analogs.

Analogs were prepared according to the scheme shown on the next page.

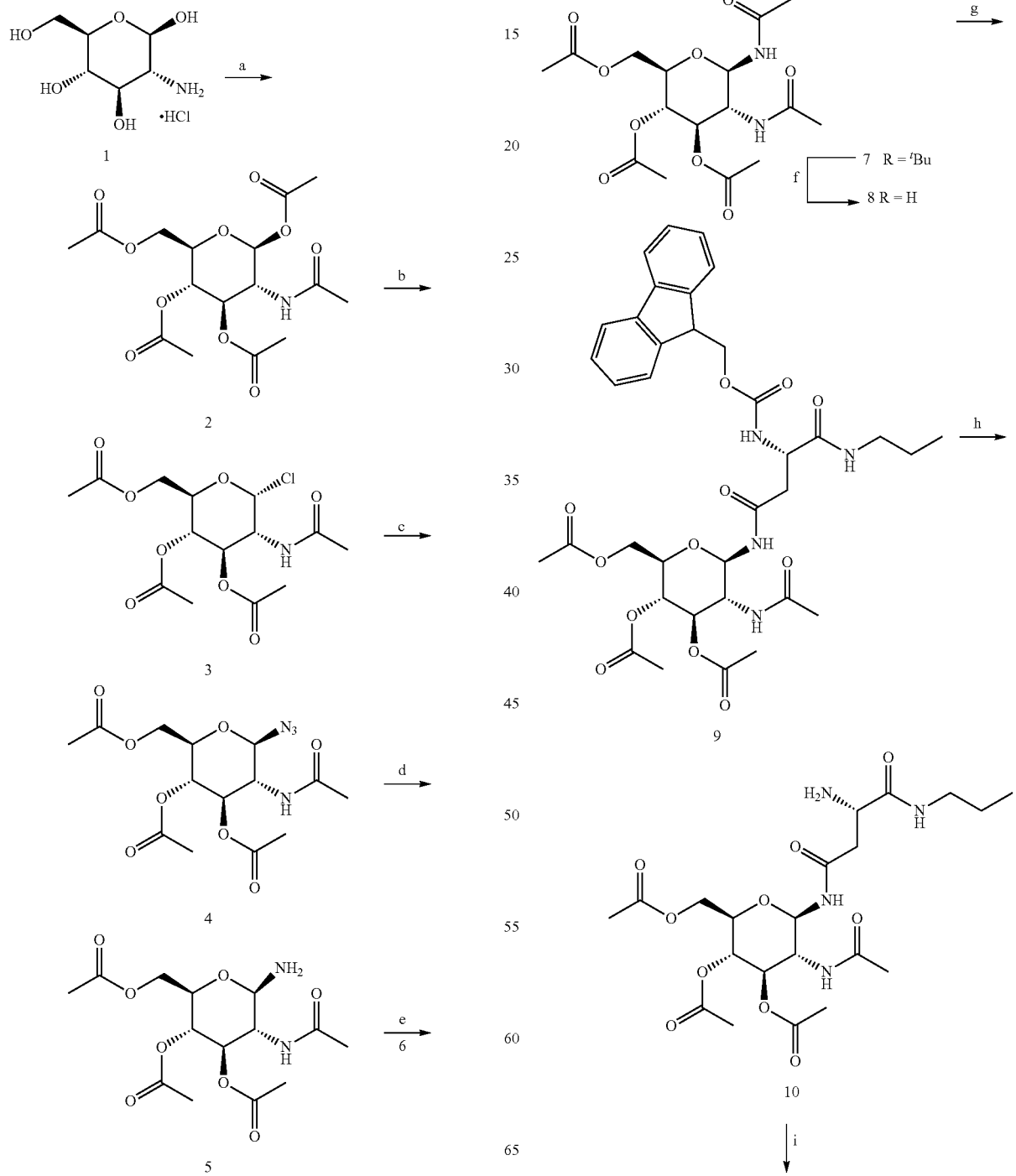

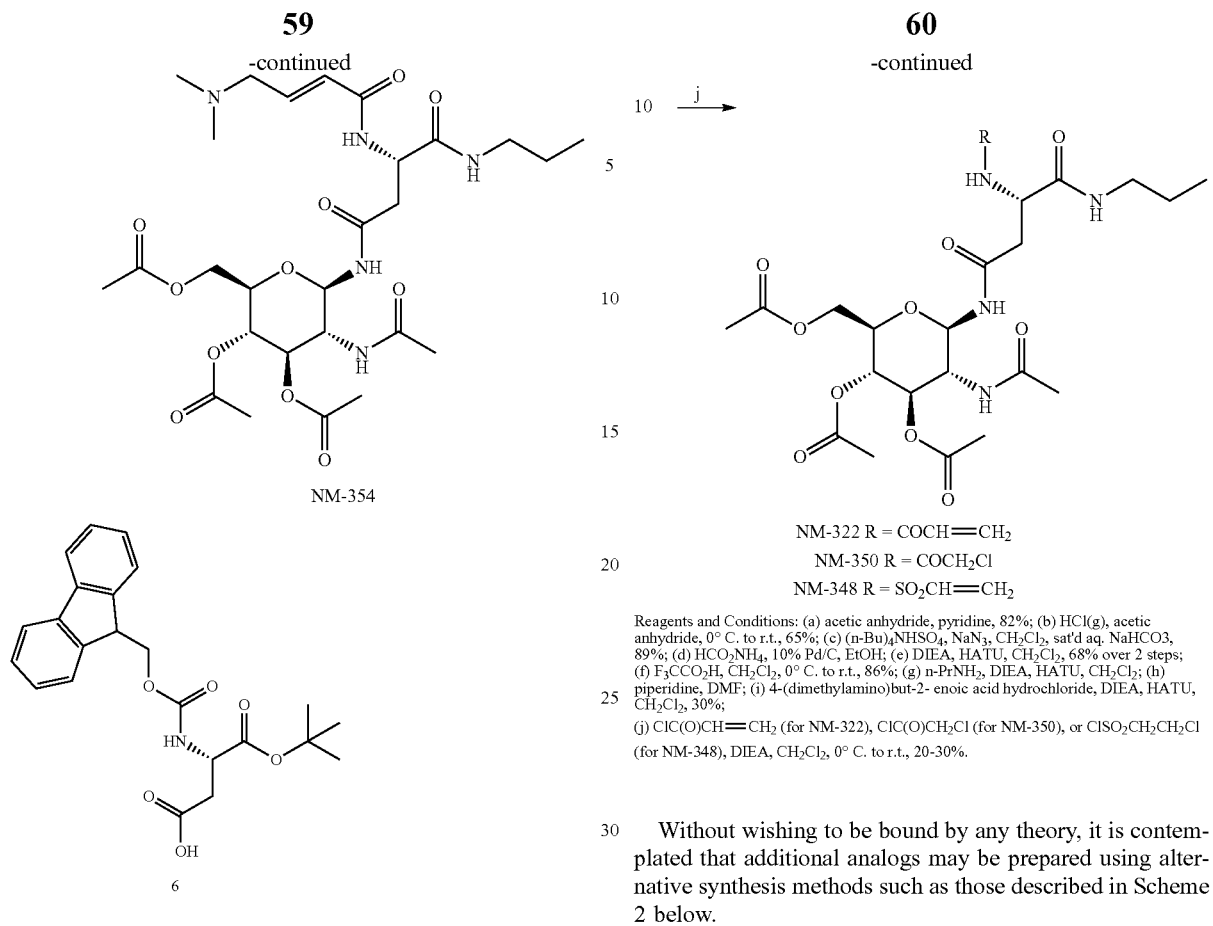

Reagents and Conditions: (a) acetic anhydride, pyridine, 82%; (b) HCl(g), acetic anhydride, 0° C. to r.t., 65%; (c) (n-Bu)₄NHSO₄, NaN₃, CH₂Cl₂, sat'd aq. NaHCO3, 89%; (d) HCO₂NH₄, 10% Pd/C, EtOH; (e) DIEA, HATU, CH₂Cl₂, 68% over 2 steps; (f) F₃CCO₂H, CH₂Cl₂, 0° C. to r.t., 86%; (g) n-PrNH₂, DIEA, HATU, CH₂Cl₂; (h) piperidine, DMF; (i) 4-(dimethylamino)but-2- enoic acid hydrochloride, DIEA, HATU, CH₂Cl₂, 30%;

(j) ClC(O)CH═CH₂ (for NM-322), ClC(O)CH₂Cl (for NM-350), or ClSO₂CH₂CH₂Cl (for NM-348), DIEA, CH₂Cl₂, 0° C. to r.t., 20-30%.

Without wishing to be bound by any theory, it is contemplated that additional analogs may be prepared using alternative synthesis methods such as those described in Scheme 2 below.

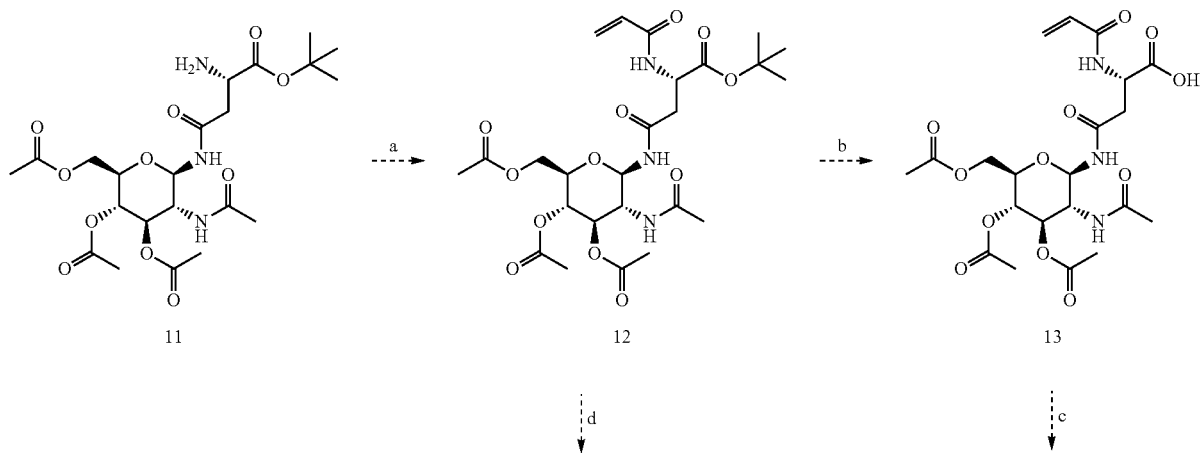

-continued

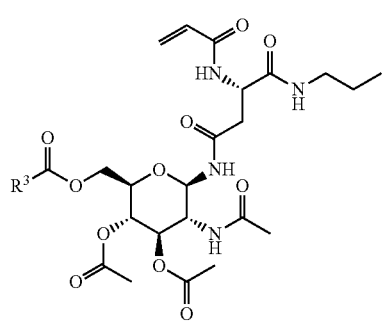

16

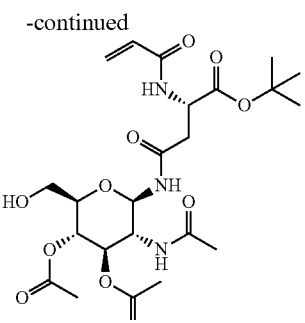

15

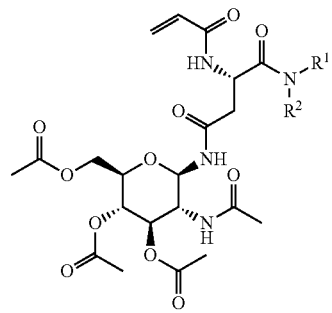

14

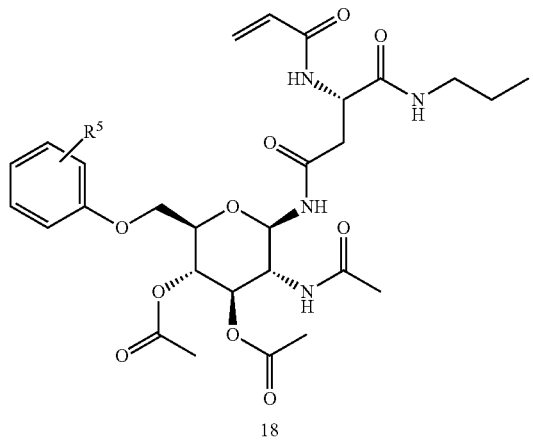

18

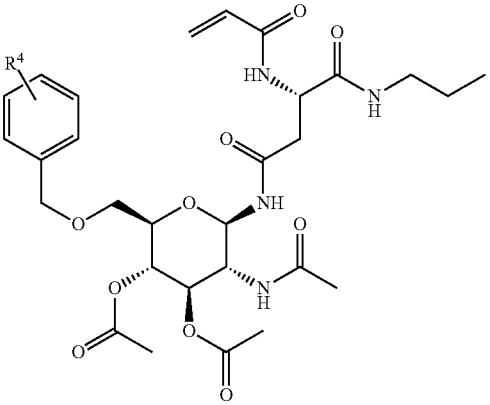

17

Reagents and Conditions: (a) acryloyl chloride, DIEA, CH$_2$Cl$_2$; (b) F$_3$CCO$_2$H; CH$_2$Cl$_2$; (c) R$^1$R$^2$NH, HATU, DIEA, DMF; (d) [$^t$Bu$_2$SnOH(Cl)]$_2$, MeOH, THF; (e) R$^3$COCl, NEt$_3$, CH$_2$Cl$_2$; (f) R$^4$C$_6$H$_4$CH$_2$O-N-(4-nitrophenyl)trifluoroacetimidate, Me$_3$SiOTf, CH$_2$Cl$_2$; (g) R$^5$C$_6$H$_4$OH, PPh$_3$, DIAD, THF; (h) ClCO$_2$Et, NEt$_3$, THF; then NH$_4$Cl, H$_2$O, -15°C.

An immediate goal for further optimization of the NGLY1 irreversible inhibitors will be achieved through variation of two additional portions of the chemotype. Synthesis of such compounds is made possible by the orthogonal protecting groups of intermediate 7 and is illustrated above. Suppose for example that a simple acrylamide proved an optimal electrophilic group for attachment to the Asn amine. In that case, reaction of 11 (accessed from 7 via cleavage of the Fmoc group) with acryloyl chloride will provide acrylamide 12. Cleavage of the tert-butyl ester will be accomplished with acid to afford acid 13. Intermediate 13 can be reacted with a host of commercially available primary and secondary amines to provide amide analogs 14. On the other hand, intermediate 12 may be reacted with a neutral organotin catalyst to selectively remove the primary acetate group to yield alcohol 15 (Orita et al., 2001), which may be converted to a host of alternative esters 16. For incorporation of non-labile groups at the C$_6$ hydroxyl, reaction of 15 with O-benzyl N-(4-nitrophenyl)trifluoroacetimidates can be used to install substituted benzyl groups to yield ethers 17 (Tsabedze et al., 2013). Likewise, Mitsunobu reactions with substituted phenols can be used to access ethers 18 (Li et al., 2009).

(2S,3R,4R,5S,6R)-3-Acetamido-6-(acetoxymethyl) tetrahydro-2H-pyran-2,4,5-triyl triacetate (2)

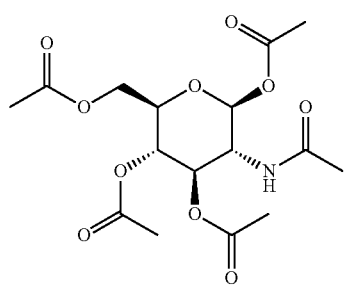

2

According to the method previously described (Dang et al., 2014), D-(+)-Glucosamine hydrochloride (USP grade, Chem-Impex Catalog No. 01450) (1.00 g, 4.64 mmol), pyridine (Anhydrous, DriSolv®, Millipore Sigma Catalog No. PX2012) (10 mL), and acetic anhydride (Certified ACS grade, Fisher Chemical Catalog No. A 10-500) (2.62 mL, 27.9 mmol) were placed in a round bottom flask. The mixture was stirred at room temperature for 12 h. The reaction was monitored by TLC. After completion of the reaction, cold water was added and the resulting solution was extracted with ethyl acetate. The organic layer was washed with saturated aqueous NaHCO$_3$, brine, dried over anhydrous Na$_2$SO$_4$, and concentrated in vacuo. The crude product was purified by flash chromatography using hexane and ethyl acetate as eluent and obtained as a white solid (1.48 g, 82%): $^1$H NMR (300 MHz, CDCl$_3$) δ 6.18 (d, J=3.6 Hz, 1H), 5.54 (d, J=8.9 Hz, 1H), 5.31-5.12 (m, 2H), 4.49 (td, J=9.7, 9.7, 3.8 Hz, 1H), 4.26 (dd, J=12.4, 4.0 Hz, 1H), 4.09-3.98 (m, 2H), 2.20 (s, 3H), 2.10 (s, 3H), 2.06 (s, 3H), 2.05 (s, 3H), 1.95 (s, 3H); $^{13}$C NMR (75 MHz, CDCl$_3$) δ 171.64, 170.68, 169.97, 169.09, 168.65, 90.65, 70.61, 69.67, 67.46, 61.51, 50.99, 23.02, 20.93, 20.70, 20.69, 20.56.

(2R,3S,4R,5R,6R)-5-Acetamido-2-(acetoxymethyl)-6-chlorotetrahydro-2H-pyran-3,4-diyl diacetate (3)

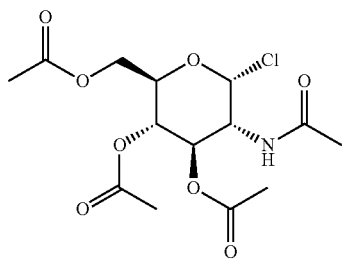

3

According to the method previously described (Greig et al., 2009), a solution of 2 (1.00 g, 2.73 mmol) in acetic anhydride (Certified ACS grade, Fisher Chemical Catalog No. A10-500) (10 mL) was cooled to 0° C. and HCl (g) was added until the solution was saturated. The HCl(g) was generated by the slow dropwise addition of concentrated sulfuric acid (Fisher Chemical Catalog No. S25597) to sodium chloride (Reagent grade, Fisher Chemical Catalog No. S25541B) in a separate flask and transferred via tubing and needle to the reaction flask. The reaction mixture was allowed to warm to room temperature and stirred for 2 days. Upon completion of the reaction, the solvent was partially removed in vacuo. Water (25 mL) was added, and the solution was extracted with ethyl acetate (2×). The combined organic phases were washed with saturated aqueous NaHCO$_3$ and brine, dried over anhydrous Na$_2$SO$_4$, and concentrated in vacuo. The crude product was purified by flash chromatography using hexane and ethyl acetate as eluent and obtained as white solid (0.650 g, 65%): $^1$H NMR (300 MHz, CDCl$_3$) δ 6.19 (d, J=3.7 Hz, 1H), 5.80 (d, J=8.7 Hz, 1H), 5.41-5.15 (m, 2H), 4.54 (ddd, J=10.5, 8.8, 3.7 Hz, 1H), 4.35-4.22 (m, 2H), 4.19-4.08 (m, 1H), 2.11 (s, 3H), 2.06 (s, 3H), 2.06 (s, 3H), 1.99 (s, 3H); $^{13}$C NMR (75 MHz, CDCl$_3$) δ 171.40, 170.55, 170.15, 169.12, 93.65, 70.88, 70.10, 66.99, 61.14, 53.44, 23.04, 20.67, 20.54.

(2R,3S,4R,5R,6R)-5-Acetamido-2-(acetoxymethyl)-6-azidotetrahydro-2H-pyran-3,4-diyl diacetate (4)

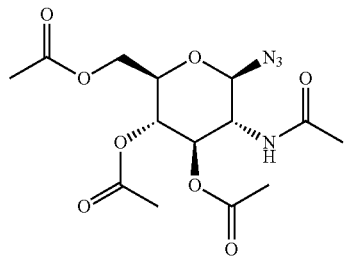

4

According to the previously described methods (Premdjee et al., 2011; Tropper et al., 1992), to a solution of 3 (1.97 g, 5.39 mmol), tetrabutylammonium hydrogen sulfate (TCI America Catalog No. T0835) (1.83 g, 5.39 mmol) and sodium azide (99%, extra pure, Acros Organics Catalog No. 190381000) (1.75 g, 26.9 mmol) in dichloromethane (19.7 mL) was added saturated aqueous NaHCO$_3$ (19.7 mL). The mixture was vigorously stirred at room temperature for 2-3 h, and the progress of reaction was monitored by TLC. After completion of the reaction, ethyl acetate (~200 mL) was added. The organic phase was separated, washed with saturated aqueous NaHCO$_3$, water, and brine. The organic phase was dried over anhydrous Na$_2$SO$_4$ and concentrated in vacuo. The crude product was purified by flash chromatography using hexane and ethyl acetate as eluent, dried, and obtained as white solid (1.78 g, 89%). Spectral data ($^1$H and $^{13}$C NMR) were found in accordance with those previously published (Premdjee et al., 2011).

(2R,3S,4R,5R,6R)-5-Acetamido-2-(acetoxymethyl)-6-aminotetrahydro-2H-pyran-3,4-diyl diacetate (5)

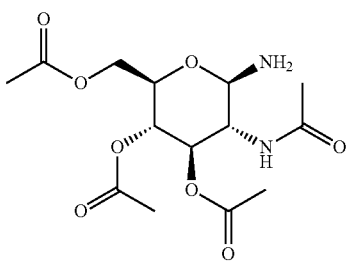

5

Ammonium formate (Sigma-Aldrich Catalog No. 156264) (139 mg, 2.20 mmol) and 10% palladium on carbon (Type 487, dry, Alfa Aesar Catalog No. A12012) (118 mg) were added to a solution of compound 4 (328 mg, 0.881 mmol) in dry ethanol (8 mL) and sealed in screw cap vial. The mixture was allowed to stir for 2 h at room temperature. After completion of reaction, methanol (5 mL) was added to the reaction mixture, and it was filtered through a syringe filter (0.2 μm). The filtrate was concentrated in vacuo and used directly in the next step without further purification. Spectral data ($^1$H and $^{13}$C NMR) were found in accordance with those previously published (Premdjee et al., 2011).

(2R,3S,4R,5R,6R)-6-((S)-3-((((9H-Fluoren-9-yl)methoxy)carbonyl)amino)-4-(tert-butoxy)-4-oxobutanamido)-5-acetamido-2-(acetoxymethyl)tetrahydro-2H-pyran-3,4-diyl diacetate (7)

N2-(((9H-fluoren-9-yl)methoxy)carbonyl)-N4-((2R,3R,4R,5S,6R)-3-acetamido-4,5-diacetoxy-6-(acetoxymethyl)tetrahydro-2H-pyran-2-yl)-L-asparagine (8)

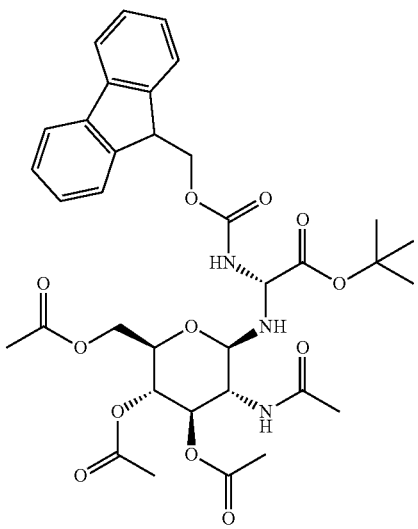

7

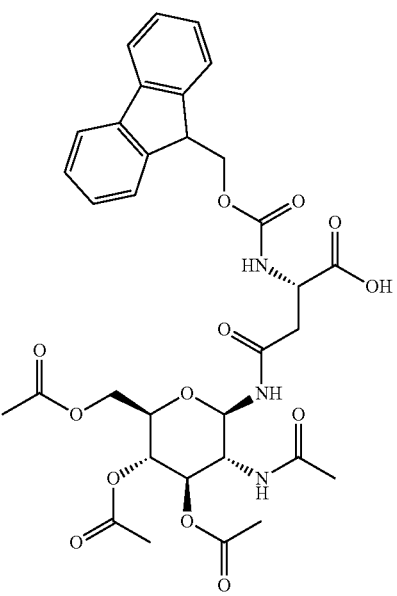

8

N,N'-Diisopropylethylamine (DIEA) (Chem-Impex Catalog No. 00141) (0.295 mL, 1.69 mmol) was added to a mixture of amino acid 6 (351 mg, 0.853 mmol) and O-(7-Aza-1H-benzotriazol-1-yl)-N,N,N',N'-tetramethyluronium hexafluorophosphate (HATU) (Matrix Scientific Catalog No. 067222) (643 mg, 1.69 mmol) in dichloromethane (5 mL) under a $N_2$ atmosphere, and the reaction mixture was allowed to stir at room temperature. After 15 min, a solution of compound 5 (291 mg, 0.840 mmol) in dichloromethane (4 mL) was added, and the reaction mixture was stirred for an additional 12 h at room temperature. The progress of the reaction was monitored by TLC and LCMS. After completion of the reaction, water (10 mL) was added, and the mixture was extracted with dichloromethane (2×). The combined organic layers were dried over anhydrous $Na_2SO_4$ and concentrated in vacuo. The crude product was purified by flash chromatography using dichloromethane and methanol as eluent and obtained as a yellow solid (850 mg, 68%). Spectral data (1H and 13C NMR) were found in accordance with those previously published (Premdjee et al., 2011).

Compound 7 (1.05 g, 1.42 mmol) was dissolved in dichloromethane (500 μL) with stirring and cooled in an ice bath. 95% Trifluoracetic acid (Alfa Aesar Catalog No. A12198) in dichloromethane (5 mL) was added, and the reaction mixture was stirred at room temperature for 2 h. The progress of the reaction was monitored by TLC and LCMS. After completion of the reaction, solvent was removed in vacuo, and the crude product was purified by reverse phase chromatography using acetonitrile and water as eluent. The product was obtained as a white solid (835 mg, 86%). Spectral data (1H and 13C NMR) were found in accordance with those previously published (Premdjee et al., 2011).

(2R,3S,4R,5R,6R)-6-((S)-3-((((9H-Fluoren-9-yl)methoxy)carbonyl)amino)-4-oxo-4-(propylamino)butanamido)-5-acetamido-2-(acetoxymethyl)tetrahydro-2H-pyran-3,4-diyl diacetate (9)

9

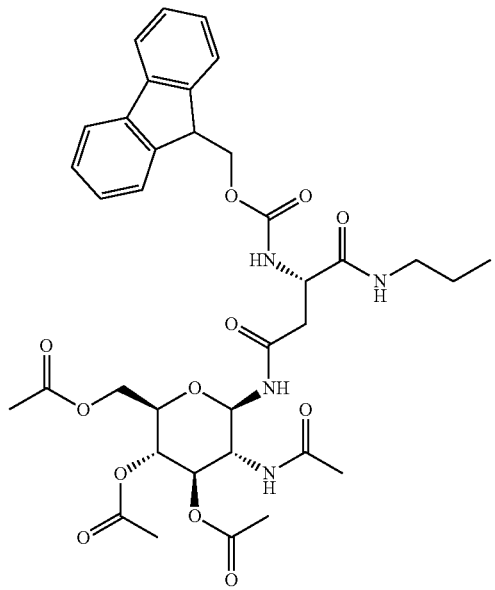

DIEA (Chem-Impex Catalog No. 00141) (141 µL, 0.878 mmol) was added to a mixture of compound 8 (300 mg, 0.439 mmol) and HATU (Matrix Scientific Catalog No. 067222) (335 mg, 0.878 mmol) in dichloromethane (10 mL) under a nitrogen atmosphere. The reaction mixture was allowed to stir at room temperature. After 15 mins, n-propylamine (Alfa Aesar Catalog No. 36635) (181 µL, 2.20 mmol) in dichloromethane (1 mL) was added. Stirring continued for 12-15 h at room temperature. The progress of the reaction was monitored by TLC and LCMS. After completion of the reaction, solvent was removed in vacuo, and the crude product was used in the next step without any further purification.

(2R,3S,4R,5R,6R)-5-Acetamido-2-(acetoxymethyl)-6-((S)-3-amino-4-oxo-4-(propylamino)butanamido)tetrahydro-2H-pyran-3,4-diyl diacetate (10)

10

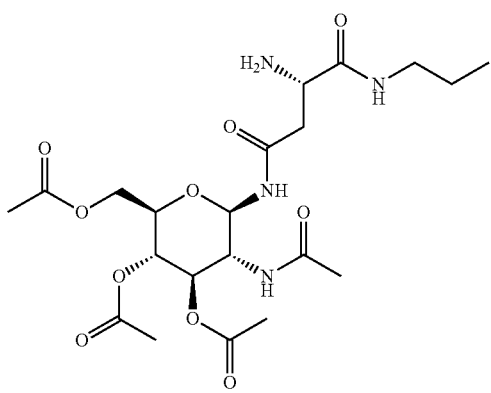

Compound 9 (300 mg, 0.413 mmol) was dissolved in 20% piperidine (Sigma-Aldrich Catalog No. 104094) solution in DMF (4 mL), and the solution was stirred for one hour at room temperature. After completion of the reaction as judged by LCMS, the solvent was removed in vacuo, and the crude product was purified by reverse phase chromatography using acetonitrile and water as eluent to afford the product as a white solid (175 mg, 84%): $^1$H NMR (300 MHz, DMSO-$d_6$) δ 8.71 (d, J=9.5 Hz, 1H), 8.00-7.79 (m, 2H), 5.12 (dd, J=18.5, 9.0 Hz, 2H), 4.82 (t, J=9.7, 1H), 4.26-4.11 (m, 1H), 4.02-3.76 (m, 3H), 3.51-3.37 (m, 1H), 3.34-3.22 (m, 1H), 3.01 (q, J=7.0 Hz, 3H), 2.00 (s, 3H), 1.97 (s, 3H), 1.91 (s, 3H), 1.74 (s, 3H), 1.40 (q, J=7.2 Hz, 2H), 0.83 (t, J=7.4 3H).

Final Analogs

(2R,3S,4R,5R,6R)-5-acetamido-2-(acetoxymethyl)-6-((S)-3-acrylamido-4-oxo-4-(propylamino)butanamido)tetrahydro-2H-pyran-3,4-diyl diacetate (NM-322)

NM-322

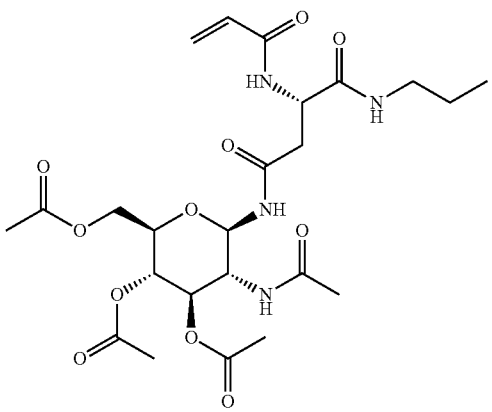

A solution of acryloyl chloride (Alfa Aesar Catalog No. L10363) (9.68 µL, 0.119 mmol) in DCM (500 µL) was added dropwise via syringe to a mixture of compound 10 (50 mg, 0.099 mmol) and triethylamine (Acros Organics Catalog No. 157911000) (30 µL, 0.22 mmol) in dichloromethane (3 mL) in an ice bath. The mixture was allowed to warm to room temperature and stirred for an additional 3-4 h. After completion of the reaction, the solvent was removed in vacuo, and the crude compound was purified by preparative HPLC using acetonitrile and water as eluent to afford the product as a white solid (21 mg, 38%): $^1$H NMR (300 MHz, DMSO-$d_6$) δ 8.51 (d, J=9.5 Hz, 1H), 8.25 (d, J=8.2 Hz, 1H), 7.88 (d, J=9.1 Hz, 1H), 7.79 (t, J=5.7 Hz, 1H), 6.27 (dd, J=17.1, 10.1 Hz, 11H), 6.07 (dd, J=17.1, 2.3 Hz, 11H), 5.58 (dd, J=10.0, 2.3 Hz, 1H), 5.13 (dt, J=19.9, 9.7 Hz, 2H), 4.81 (t, J=9.7 Hz, 1H), 4.63 (q, J=7.5 Hz, 1H), 4.17 (dd, J=12.4, 4.2 Hz, 1H), 3.99-3.75 (m, 3H), 2.99 (q, J=6.3 Hz, 2H), 2.59 (dd, J=15.9, 6.2 Hz, 1H), 2.39 (dd, J=16.0, 7.4 Hz, 1H), 1.99 (s, 3), 1.96 (s, 3H), 1.90 (s, 3H), 1.73 (s, 3H), 1.42-1.34 (m, 2H), 0.80 (t, J=7.4, 3H); $^3$C NMR (75 MHz, DMSO-$d_6$) δ 170.90, 170.51, 170.29, 169.97, 169.94, 169.79, 164.72, 132.08, 125.86, 78.37, 73.81, 72.67, 68.79, 62.28, 52.61, 50.63, 49.77, 37.89, 23.11, 22.68, 21.00, 20.88, 20.84, 11.74; HRMS, calc'd for $C_{24}H_{37}N_4O_{11}^+$ [M+H], 557.2453; found 557.2454.

(2R,3S,4R,5R,6R)-5-Acetamido-2-(acetoxymethyl)-6-((S)-3-(2-chloroacetamido)-4-oxo-4-(propylamino)butanamido)tetrahydro-2H-pyran-3,4-diyl diacetate (NM-350)

(2R,3S,4R,5R,6R)-5-Acetamido-2-(acetoxymethyl)-6-((S)-4-oxo-4-(propylamino)-3-(vinylsulfonamido)butanamido)tetrahydro-2H-pyran-3,4-diyl diacetate (NM-348)

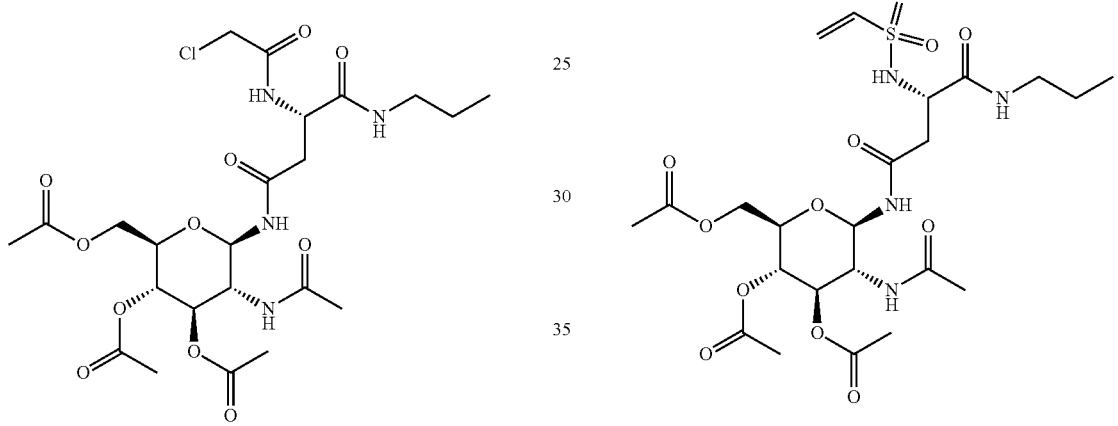

A solution of chloracetyl chloride (Alfa Aesar Catalog No. A15846) (10.8 mg, 0.095 mmol) in DCM (500 µL) was added dropwise via syringe to a mixture of compound 10 (40 mg, 0.079 mmol) and triethylamine (Acros Organics Catalog No. 157911000) (25 µL, 0.18 mmol) in dichloromethane (3 mL) in an ice bath. The mixture was allowed to warm to room temperature and stirred for an additional 3-4 h. After completion of the reaction, the solvent was removed in vacuo, and the crude compound was purified by preparative HPLC using acetonitrile and water as eluent to afford the product as a white solid (25 mg, 54%): $^1$H NMR (300 MHz, DMSO-$d_6$) δ 8.53 (d, J=9.4 Hz, 1H), 8.34 (d, J=8.3 Hz, 1H), 7.88 (d, J=9.3 Hz, 1H), 7.82 (t, J=5.9 Hz, 1H), 5.13 (dt, J=19.8, 9.7 Hz, 2H), 4.81 (t, J=9.8 Hz, 1H), 4.54 (q, J=7.0 Hz, 1H), 4.20-4.11 (m, 1H), 4.09 (s, 2H), 4.03-3.77 (m, 3H), 2.99 (q, J=6.1 Hz, 2H), 2.57 (dd, J=15.9, 5.9 Hz, 1H), 2.48-2.39 (m, 1H), 1.99 (s, 3H), 1.96 (s, 3H), 1.90 (s, 3H), 1.74 (s, 3H), 1.38 (h, J=7.2 Hz, 2H), 0.81 (t, J=7.4 Hz, 3H); $^{13}$C NMR (75 MHz, DMSO-$d_6$) δ 170.49, 170.40, 170.38, 170.33, 169.97, 169.77, 166.00, 78.39, 73.85, 72.71, 68.82, 62.30, 52.57, 50.08, 43.11, 37.74, 23.08, 22.76, 22.68, 20.99, 20.87, 20.84, 11.74; HRMS, calc'd for $C_{23}H_{36}ClN_4O_{11}^+$ [M+H], 579.2064; found 579.2067.

A solution of 2-Chloroethanesulfonyl chloride (TCI America Catalog No. C1142) (14.5 mg, 0.089 mmol) in DCM (500 µL) was added dropwise via syringe to a mixture of compound 10 (45 mg, 0.089 mmol) and triethylamine (Acros Organics Catalog No. 157911000) (25 µL, 0.18 mmol) in dichloromethane (3 mL) in an ice bath. The mixture was allowed to warm to room temperature and stirred for an additional 3-4 h. After completion of the reaction, the solvent was removed in vacuo, and the crude compound was purified by preparative HPLC using acetonitrile and water as eluent to afford the product as a white solid (27 mg, 50%): $^1$H NMR (300 MHz, DMSO-$d_6$) δ 8.64-8.44 (m, 1H), 7.90 (d, J=9.06 Hz, 1H), 7.83 (t, J=5.80 Hz, 2H), 7.57 (s, 1H), 6.63 (dd, J=16.5, 9.9 Hz, 1H), 6.10-5.77 (m, 2H), 5.26-5.03 (m, 2H), 4.82 (t, J=9.8, 1H), 4.18 (dd, J=12.3, 4.1 Hz, 1H), 4.10-3.72 (m, 4H), 2.99 (q, J=6.5 Hz, 2H), 2.56 (d, J=6.0 Hz, 1H), 2.46-2.31 (m, 1H), 2.00 (s, 3H), 1.97 (s, 3H), 1.91 (s, 3H), 1.76 (s, 3H), 1.41 (dt, J=14.3, 7.4 Hz, 2H), 0.82 (t, J=7.3 Hz, 2H); $^{13}$C NMR (75 MHz, DMSO-$d_6$) δ 170.50, 170.13, 170.08, 170.02, 170.00, 169.77, 137.86, 125.71, 78.43, 73.77, 72.69, 68.84, 62.31, 53.30, 52.60, 52.04, 39.03, 23.12, 22.63, 20.99, 20.88, 20.84, 11.75; HRMS, calc'd for $C_{23}H_{37}N_4O_{12}S^+$ [M+H], 593.2123; found 593.2135.

(2R,3S,4R,5R,6R)-5-Acetamido-2-(acetoxymethyl)-6-((S)-3-((E)-4-(dimethylamino)but-2-enamido)-4-oxo-4-(propylamino)butanamido)tetrahydro-2H-pyran-3,4-diyl diacetate (NM-354)

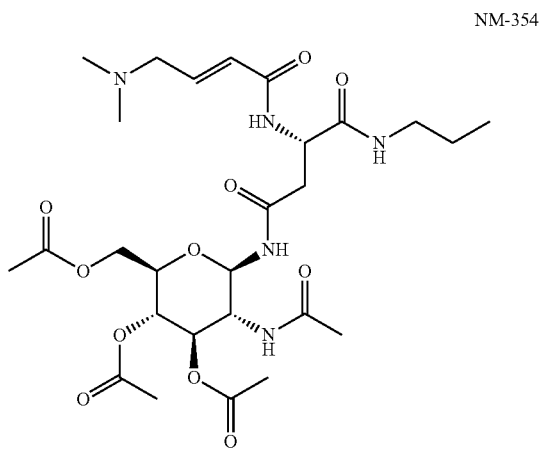 [SMILES: CCCNC(=O)[C@H](CC(=O)N[C@@H]1O[C@H](COC(C)=O)[C@@H](OC(C)=O)[C@H](OC(C)=O)[C@H]1NC(C)=O)NC(=O)/C=C/CN(C)C]

NM-354

DIEA (Chem-Impex Catalog No. 00141) (31 µL, 0.191 mmol) was added to the mixture of Compound 10 (48 mg, 0.0956 mmol) and HATU (Matrix Scientific Catalog No. 067222) (48 mg, 0.124 mmol) in dichloromethane (3 mL) under a nitrogen atmosphere and stirred for 15 min. A solution of 4-(dimethylamino)but-2-enoic acid hydrochloride (Ark Pharm Catalog No. AK-44120) (16 mg, 0.0965 mmol) in dichloromethane (2 mL) was added to the mixture, and it was stirred for an additional 10 h. After completion of the reaction, the solvent was removed in vacuo, and the crude product was purified by preparative HPLC using acetonitrile and water as eluent to afford the product (17.2 mg, 30%): $^1$H NMR (300 MHz, CD$_3$OD) δ 8.61 (d, J=9.1 Hz, 1H), 8.44 (d, J=8.0 Hz, 1H), 8.15 (d, J=9.2 Hz, 1H), 7.95 (t, J=5.6 Hz, 1H), 6.71 (dt, J=14.7, 7.3 Hz, 1H), 6.40 (d, J=15.3 Hz, 1H), 5.29-5.11 (m, 2H), 5.05-4.92 (m, 2H), 4.24 (dd, J=12.4, 4.4 Hz, 1H), 4.12-3.85 (m, 4H), 3.85-3.79 (m, 1H), 3.20-3.04 (m, 2H), 2.90 (s, 6H), 2.81-2.56 (m, 2H), 2.02 (s, 3H), 2.00 (s, 3H), 1.98 (s, 3H), 1.87 (s, 3H), 1.51 (h, J=7.2 Hz, 2H), 0.90 (t, J=7.4 Hz, 3H); $^{13}$C NMR (75 MHz, CD$_3$OD) δ 172.33, 171.10, 171.08, 170.86, 170.37, 169.90, 164.45, 132.06, 130.24, 78.22, 73.31, 73.26, 68.50, 61.88, 57.40, 52.76, 50.09, 41.84, 40.97, 37.16, 22.12, 21.34, 19.20, 19.17, 19.13, 10.26; HRMS, calc'd for C$_{27}$H$_{44}$N$_5$O$_{11}{}^+$ [M+H], 614.3032; found 614.3037.

Figure 19:
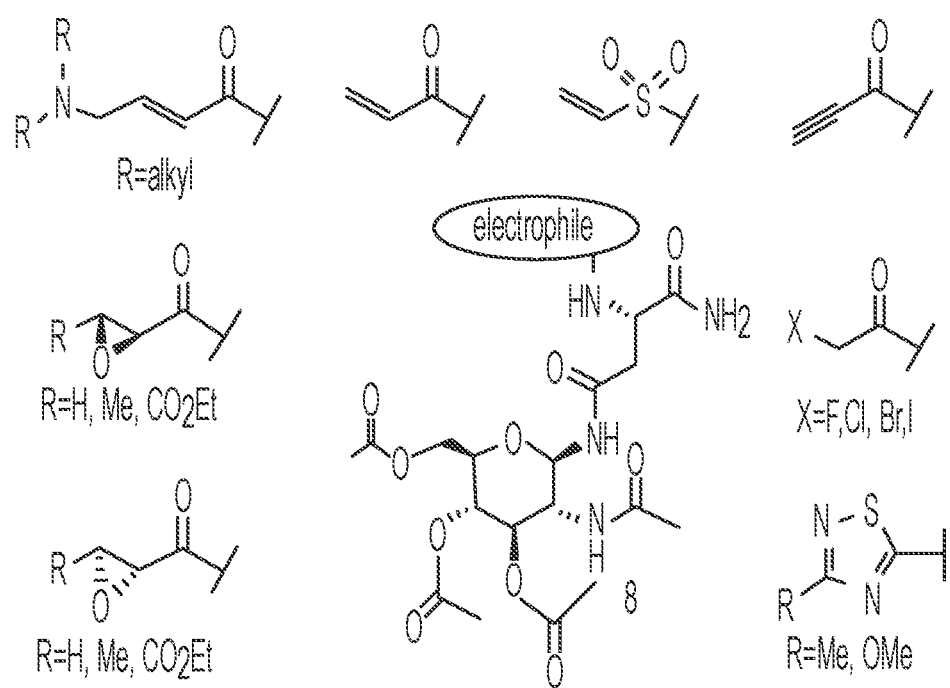
FIG. 19 shows initial targets for synthesis and evaluation as irreversible inhibitors of NGLY1.

Example 11—Compound Docking and Molecular Dynamics Simulations to Evaluate Newly Designed Compounds Using in silico analysis, the newly designed compounds contemplated (FIGS. 18 and 19) will be docked into the human NGLY1 homology model for estimation of binding affinity. The compounds with the most promising binding affinity with human NGLY1 will be subject to molecular dynamics simulation using a simulation package Assisted Model Building with Energy Refinement (AMBER). The binding energies of compounds will be further analyzed using Molecular Mechanics/Poisson-Boltzmann Surface Area (MM-PBSA) methods. Each residue contributions to the binding affinities will be calculated to identify key residues and key elements of ligands that contribute most to the binding affinities. The key structural fragments of ligands involved in the ligand-protein interactions will be identified to provide guidance to further improve the designed compounds.

Example 12—Chemical Synthesis Plan for the Derivation of Additional Glycosylamine Analogs as Potential NGLY1 Inhibitors Based on the core structure illustrated in FIG. 18, additional glycosylamine analogs will be generated according to the synthesis plan described herein to test their activity of NGLY1 inhibition.

Example 13—Virtual Screening for New Class of Inhibitors

Ligand-based and structure-based screening will also be performed to further empower the ability for designing specific inhibitors that target human NGLY1. For the ligand-based screening, using the compounds identified from preliminary studies as templates, molecular fingerprints will be performed and three-dimensional (3D) similarity searching based on the identified structural fragments involved in the key interactions between ligand and protein to search for NGLY1 selective compounds. Ligand-based 3D similarity search will be performed using free software OpenBabel. On the other hand, structure-based screening will be performed using the catalytic site of human NGLY1 as the binding pocket. The ZINC database, NIH Molecular Library Small Molecule Repository (MLSMR) collection and DrugBank collection of compounds will be used in both ligand-based and structure-based screening. Both commercially available software, Glide® from Schrödinger Inc. (Friesner et al., 2005), and free docking software, AutoDock, will be employed to carry out proposed virtual screening calculations to validate our docking results. Ranked by overall score, the top compounds will be selected for energy minimization and re-scored using different scoring functions such as AutoDock and LigScore. After removing the duplicates, the NGLY1 complexes with the most promising chemical ligands will be subjected to a 100 ps molecular dynamics simulation in implicit solvent to evaluate the complex stability. The binding free energies will be evaluated with MM-PBSA methods to rank all tested compounds. Compounds with top 25 scores for binding human NGLY1 determined by both ligand-based and structure-based screening will be selected for purchase and/or synthesis so that they may be biologically tested. It is likely that the hits identified from this structure-based screening will not contain any electrophilic moiety. They can be strong candidates for the use as competitive inhibitors by themselves or as optimization leads.

Example 14—Compound Evaluation

Synthesis and purification of all disclosed compounds is carried out or is to be carried out using the latest in synthetic chemistry technology. Where applicable, microwave-assisted organic synthesis (MAOS) (Wolkenberg et al., 2005), polymer supported scavengers and reagents (Ley et al., 2000), and automated preparatory normal and reverse phase chromatography will be utilized. LC-MS and proton NMR are used to ensure that each new analog is at least 95% pure. All new analogs are prepared on a 10-20 mg scale for initial characterization and testing. For instances where scale-up of select compounds for advanced studies is necessary, the targeted amount of compound will be determined on a case by case basis. Compounds are analyzed using a cell-based test for studying their ability to inhibit human NGLY1 in cultured cells and for testing their potential anticancer effects on melanoma cells. The specific synthesis and characterization is included below.

Example 15—Materials and Methods

A. Cell Culture

Human dermal fibroblasts were cultured in DMEM (Thermo Fisher Scientific, Carlsbad, CA) containing 10% fetal bovine serum (FBS; Thermo Fisher Scientific, Carlsbad, CA) at 37° C. HEMI and HEMd (ScienCell Research Laboratories, Carlsbad, CA) cells were cultured in melanocyte medium (MelM; ScienCell Research Laboratories, Carlsbad, CA). Human melanoma cells were cultured using RPMI-1640 medium (Thermo Fisher Scientific, Carlsbad, CA) or DMEM/F12 medium (Thermo Fisher Scientific, Carlsbad, CA) containing 10% FBS. WA09 human embryonic stem cells (hESCs) were obtained from the WiCell Stem Cell Bank (WiCell Research Institute, Madison, WI). HMi-506 (Jones, et al., 2013) and NGLY1Pt1i-509 hiPSCs were established using CytoTune Sendai Reprogramming Kit (Thermo Fisher Scientific, Carlsbad, CA). We followed the previously described method (Wang, et al., 2011) for culturing undifferentiated human pluripotent stem cells (hPSCs) in a feeder cell-free condition, except the use of TeSR-E8 medium (Stemcell Technologies, Vancouver, Canada) and L7 hPSC passaging solution (Lonza, Walkersville, MD) in this study. The detailed information of cells used in this study was summarized in Table 5. The experiments using hPSCs were performed in compliance with the guidelines and approval of the institutional biosafety committee at UNTHSC. All cells were periodically tested using the MycoAlert *mycoplasma* detection kit (Lonza, Walkersville, MD) and free of *mycoplasma*.

TABLE 5

| Sample Name | Registry Name[a] | Note[b] |
|---|---|---|
| Human embryonic stem cells | | |
| WA09 | WA09 | Obtained from the WiCell Stem Cell Bank: feeder cell-free culture on Metrigel, passaged using L7 hPSC passaging solution |
| Induced pluripotent stem cells from Human Dermal Fibroblasts (HDF) | | |
| NGLY1Pt1i-507 | N/A | Sendal virus-mediated reprogramming in NGLY1-deficient patient's dermal fibroblasts (GM25990): feeder cell-free culture on Matrigel, passaged using L7 hPSC passaging solution |
| NGLY1Pt1i-508 | N/A | Sendal virus-mediated reprogramming in NGLY1-deficient patient's dermal fibroblasts (GM25990): feeder cell-free culture on Matrigel, passaged using L7 hPSC passaging solution |
| NGLYPt1i-509 | N/A | Bendal virus-mediated reporgramming in NGLY1-deficient patient's dermal fibroblasts (GM25990): fesder cell-free culture on Matrigel, passaged using L7 hPSC passaging solution |
| Normal somatic cells | | |
| HDF51 (HDF-f)[c] | N/A | Human dermal fibroflasts, fetal skin: purchased from Sciencell |
| HM(HEMI)[c] | N/A | Human epidermal melanocytes (light), neonatal skin; purchased from Sciencell |
| HEMd | N/A | Human epidermal melanocytes (dark), neonatal skin: purchased from Sciencell |
| HDF418 | N/A | Human dermal fibroblasts: isolated from the forearm skin biopsy sample of an adult male |
| Cancer cells | | |
| UACC257 | N/A | Human melanoma cells cultured using RPMI-1640 medium containing 10% FBS, enzymatic passaged using trypsin-EDTA |
| COLO829 | N/A | Human melanoma cells cultured using RPMI-1640 medium containing 10% FBS, enzymatic passaged using trypsin-EDTA |
| SK-MEL-2 | N/A | Human melanoma cells cultured using RPMI-1640 medium containing 10% FBS, enzymatic passaged using trypsin-EDTA |
| SK-MEL-5 | N/A | Human melanoma cells cultured using RPMI-1640 medium containing 10% FBS, enzymatic passaged using trypsin-EDTA |
| 451Lu | N/A | Human melanoma cells cultured using RPMI-1640 medium containing 10% FBS, enzymatic passaged using trypsin-EDTA |
| MEL1617 | N/A | Human melanoma cells cultured using RPMI-1640 medium containing 10% FBS, enzymatic passaged using trypsin-EDTA |
| MALME3M | N/A | Human melanoma cells cultured using DMEM medium containing 10% FBS, enzymatic passagd using trypsin-EDTA |
| Cells using for reprogramming | | |
| HDF (GM25990) | N/A | Human dermal fibroblasts derived from the skin biopsy sample of a patient with NGLY1 deficiency, cultured using DMEM medium containing 10% FBS, obtained from Corieil Biorepository |

[a]Name of cell line submitted to University of Massachusetts (UMass) international Stem Cell Registry
[b]Somatic cell type, reprogramming method, culture condition, source of cells
[c]Nomenclature used by the vendor B. Melanoma Patient Samples The RNA samples of tumor tissues from randomly selected melanoma patients were obtained from OriGene Technologies (Rockville, MD). The tissue arrays that contain 8 cases of human normal skin and 36 cases of melanoma tumors were acquired from BioChain Institute (Newark, CA).

C. CRISPR-Cas9-Mediated Gene Editing

For CRISPR-Cas9-mediated gene editing to knockout the expression of NGLY1 in hPSCs, we designed two NGLY1-targeting sgRNA sequences (sgRNA37: 5'CATTCAACAGCTCCTCTGAC3' (SEQ ID NO: 3) and sgRNA39: 5'GATCTGATGACTGCCCTTGA3' (SEQ ID NO: 4)) using the CRISPR Design Tool (crispr.mit.edu). These two sgRNA sequences were independently cloned into a lentiCRISPRv2 plasmid (Addgene, Cambridge, MA) to generate two constructs of an one-vector system for sgRNA and Cas9 expression. WA09 hESCs transduced with the sgRNA and Cas9 expression constructs were selected using puromycin and subjected to a single-cell cloning process. Using a surveyor mutation detection kit (Integrated DNA Technologies, Coralville, IA) to examine indel mutations at the editing sites followed by Western blotting to test NGLY1 expression, hESCs with NGLY1 gene mutations that lead to the ablation of NGLY1 expression were chosen and further expanded.

D. Knockdown of NGLY1 and GADD153

The knockdown of NGLY1 expression in melanoma cells was achieved by the transduction of pZIP-TRE3GS lentiviral expression vectors that carry two independent shRNA sequences (Below; TransOMIC Technologies, Huntsville, AL). A pZIP-TRE3GS vector that carries a NT-shRNA sequence was used as the control. The expression of the shRNA sequences and an open reading frame of the ZsGreen reporter is driven by the TRE3GS doxycycline-inducible promoter. The transduced cells were selected using puromycin for a prolonged period (~4 weeks) to obtain the stable clones of cancer cells that carry inducible NT-shRNA, NGLY1-shRNA645 and NGLY1-shRNA647 sequences.

The knockdown of GADD153 expression in melanoma cells was achieved by the transduction of pZIP-hEF1a-RFP lentiviral expression vectors that carry three independent shRNA sequences (Below; TransOMIC Technologies, Huntsville, AL). A pZIP-hEF1a-RFP lentiviral expression vector carries a NT-shRNA sequence was used as the control. The expression of the shRNA sequences and an open reading frame of the RFP reporter is driven by the human EF1α gene promoter.

E. Overexpression of Human NGLY1

A pLenti expression vector that carries a Myc-DDK-tagged-human NGLY1 open reading frame driven by a CMV promoter (OriGene Technologies, Rockville, MD) was transduced into cells for the overexpression of NGLY1. A pLenti-C-Myc-DDK empty vector was used as the transduction control.

F. Immunohistochemistry (IHC) and Fluorescence Staining

The general procedure for antibody-mediated fluorescence staining was previously described (Wang, et al., 2011) and provided below. The detailed information of primary antibodies was summarized in Table 6.

TABLE 6

Primary Antibodies and Lectins Used Herein

| Antibody/Lectin Name | Catalog Number | Sources |
| --- | --- | --- |
| Antibodies used in IHC or fluorescence straining | | |
| NGLY1 | HPA036825 | Millipore Sigma |
| TRA-1-81 | 09-001 | Stemgent |
| POU5F1 | 2840 | Cell Signaling Technology |
| NANOG | MABD24 | Millipore Sigma |
| TUBB3 | MRB-435P | Biolegend (formerly Covance) |
| Smooth Muscle Actin (SMA) | MAB1420 | R&D Systems |
| SOX17 | AF1924 | R&D Systems |
| DYKDDDDK Tag | MA1-142-A555 | Thermo Fisher Scientific |
| Brachyury | sc-17745 | Santa Cruz Biotechnology |
| Antibodies used in immunoblotting | | |
| NGLY1 | HPA036825 | Millipore Sigma |
| pMEK1/2 | 9154 | Cell Signaling Technology |
| MEK1/2 | 4694 | Cell Signaling Technology |
| pERK1/2 | 4370 | Cell Signaling Technology |
| ERK1/2 | 4696 | Cell Signaling Technology |
| ACTIN | 08691001 | MP Biomedicals |
| POU5F1 | 2840 | Cell Signaling Technology |
| NANOG | MABD24 | Millipore Sigma |
| DYKDDDDK Tag | 8146 | Cell Signaling Technology |
| GADD153 | NB600-1335 | Novus Biologicals |
| pIRF3 | 4947 | Cell Signaling Technology |
| IRF3 | 11904 | Cell Signaling Technology |
| IRF7 | 13014 | Cell Signaling Technology |
| pTBK1 | 5483 | Cell Signaling Technology |
| TBK1 | 3504 | Cell Signaling Technology |
| Ubiquitin | 3936 | Cell Signaling Technology |
| KDEL | ab12223 | Abcam |
| ATF4 | 11815 | Cell Signaling Technology |
| TCF11/NRF1 | 8052 | Cell Signaling Technology |
| ZsGreen | 632598 | Takara |
| Cytokine neuralization | | |
| IFNβ1 | MAB814-100 | R&D Systems |
| IL-29 | MAB15981-100 | R&D Systems |
| Lectin used in fluorescence straining | | |
| UEA-I | FL-1061 | Vector Laboratories |

G. Immunoblotting

The general procedure for immunoblotting was described in a previously published report (Wang, et al., 2008), except that cell lysates were prepared using M-PER mammalian protein extraction reagent (Thermo Fisher Scientific, Carlsbad, CA) containing EDTA-free protease inhibitor and phosphatase inhibitor cocktails (Millipore Sigma, St. Louis, MO). The detailed information of primary antibodies was summarized in Table 6. HRP-conjugated secondary antibodies were from Jackson ImmunoResearch Laboratories (West Grove, PA).

H. Gene Expression Analysis by qRT-PCR and Microarrays

The procedures for microarray analysis are provided below. The test of cellular pluripotency based on the transcriptomic features of cell samples was performed using the PluriTest (pluritest.org/) (Muller, et al., 2011). Multiplex qRT-PCR was performed using cDNA generated from the RNA samples and Taqman© assays for the NGLY1, FABP7, RSAD2, CCL5, IFNB1 and ACTB (internal control) genes (assay ID #Hs01046153_m1, Hs00361424_g1, Hs00369813_m1, Hs00982282_m1, Hs01077958_s1 and Hs03023943_g1; Thermo Fisher Scientific, Carlsbad, CA), according to the manufacturer's instructions.

I. Cytokine Profiling and Neutralization

U-PLEX Human Interferon Combo assay kits and a SECTOR Imager 2400 (Meso Scale Discovery, Rockville, MD) were used to measure cytokine contents in conditional medium samples of cells with indicated treatment, according to the manufacturer's instructions. Specific antibodies against human INFβ1 and IL-29 (R&D Systems, Minneapolis, MN; Table 6) were used to neutralize the cytokines in cell samples, while the IgG isotype (Jackson ImmunoResearch Laboratories, West Grove, PA) was applied to control samples.

J. In Vivo Studies

The animal work in this study was completed using an animal study service provided by the translational core laboratory at the University of Maryland, Baltimore. All experimental procedures and protocols utilizing mice were approved by the Institutional Animal Care and Use Committee at the University of Maryland. The procedures are provided below K. Chemical Synthesis and Characterization of NGLY1 Inhibitors Z-VAD-fmk were purchased from Millipore Sigma (St. Louis, MO). WRR139 was synthesized and characterized according to the chemical approaches previously described (Tomlin, et al., 2017).

L. Production of Recombinant Human NGLY1 and RNase B Deglycosylation Assay

The procedures for generating recombinant human NGLY1 and testing its enzymatic activity were provided as described below.

M. Statistical Analysis

The significance of differences in comparisons was primarily determined by the two-tailed Student's t-test for a two-group comparison, unless stated otherwise. The association of NGLY1 staining results and pathological conditions in normal skin and melanoma tumor tissues was examined using a 2×2 contingency with the two-tailed Fisher's exact test.

N. Data and Materials Availability

The gene expression array data have been deposited with links to an accession number GSE106936 in the Gene Expression Omnibus (GEO). Other data included within the article to support the findings of this study are available from the corresponding author upon reasonable request. The biological samples and novel compounds used in this study may be distributed upon request and under institutional material transferring agreements or a licensing process.

O. Knockdown of NGLY1 and GADD153 (DDIT3)

```
NGLY1-shRNA645 (SEQ ID NO: 5):
5' CCGAGUUUCAAAUAACAAUCAAUAGUGAAGCCACAGAUGUAUUG

AUUGUUAUUUGAAACUCGAU 3',

NGLY1-shRNA647 (SEQ ID NO: 6):
5' AAAGCAUUACUUCGAGACACUAUAGUGAAGCCACAGAUGUAUAG

UGUCUCGAAGUAAUGCUUCU 3',

DDIT3-shRNA301 (SEQ ID NO: 7):
5' AAGGUCCUGUCUUCAGAUGAAAUAGUGAAGCCACAGAUGUAUUU

CAUCUGAAGACAGGACCUCU 3',

DDIT3-shRNA303 (SEQ ID NO: 8):
5' AGAGAAAGAACAGGAGAAUGAAUAGUGAAGCCACAGAUGUAUUC

AUUCUCCUGUUCUUUCUCCU 3',

DDIT3-shRNA304 (SEQ ID NO: 9):
5' AGUCCUGUCUUCAGAUGAAAAAUAGUGAAGCCACAGAUGUAUUU

UUCAUCUGAAGACAGGACCU 3'
```

P. Immunohistochemistry (IHC) and Fluorescence Staining

For the staining of pluripotency biomarkers in hPSCs and their differentiated derivatives, cells were plated into 24-well plates, fixed and permeabilized and incubated with primary antibodies against specific pluripotency biomarkers and fluorophore-conjugated secondary antibodies (Thermo Fisher Scientific, Carlsbad, CA). For the IHC staining of FFPE tissue sections, tissue sections were dewaxed, rehydrated, subjected to antigen retrieval using a universal antigen retrieval reagent (R&D Systems, Minneapolis, MN), and reacted with a primary antibody against human NGLY1 (Millipore Sigma, St. Louis, MO) at 4° C. for overnight. After thorough washing with PBS containing 0.2% Tween-20 (PBST; Millipore Sigma, St. Louis, MO), the tissue samples were reacted with a HRP-conjugated secondary antibody (Jackson ImmunoResearch Laboratories, West Grove, PA) at room temperature for 2 hours, washed with PBST, processed using an AEC peroxidase substrate kit (Vector Laboratories, Burlingame, CA) and subsequently stained with Mayer's hematoxylin solution (Millipore Sigma, St. Louis, MO). The stained tissue samples were mounted with cover slips and read by a pathologist who is experienced in the identification of cancer cells in tissue sections with IHC staining.

Q. Flow Cytometry

For quantifying the percentages of apoptotic cells in cell samples, samples (~1×10$^6$ cells per sample) stained with Annexin V-Alexa Fluor 647 (Thermo Fisher Scientific, Carlsbad, CA) according to the manufacturer's instruction were analyzed using a SH800Z cell sorter (Sony Biotechnology, San Jose, CA). In addition to the Annexin V-Alexa Fluor 647, anti-FLAG rat IgG-Alexa Fluor 555 (Thermo Fisher Scientific, Carlsbad, CA) was used for labeling fixed cells with the overexpression of FLAG-tagged human NGLY1 prior to cytometry analysis in the rescue study.

R. Cell Viability Test

Cells were seeded into 96-well plates (2,500-5,000 cells/well, depending on cell types), incubated overnight, and treated as indicated. If DMSO was used as a vehicle to dissolve compounds and generate stock compound solutions for drug treatment, control groups received DMSO (0.1%, final concentration). After treatment, cells were incubated in FBS-free medium containing 0.4 mg/mL MTT (3-[4,5-dimethyl-thiazol-2-yl]-2,5-diphenyl-2H-tetrazolium bromide; TCI America, Portland, OR) at 37° C. for 1 hour. Reduced MTT was solubilized in DMSO for determination of absorbance at 570 nm. Absorbance of reduced MTS was directly measured in the reaction medium at 490 nm. The relative cell viability in each treatment condition was calculated based on absorbance values. The combination indices (C.I.) of cell viability suppression induced by combinatorial treatment were calculated using Calcusyn 2.0. C.I. values less than 1 are generally considered as synergistic effects from the combinatorial treatment. The lower a C.I. value gets, the stronger the synergistic effect is.

S. Gene Expression Analysis by qRT-PCR and Microarrays

Total RNA was isolated from cell samples using the mirVana miRNA Isolation Kit (Thermo Fisher Scientific, Carlsbad, CA). The quality of each RNA samples was determined using an Agilent 2200 Tape Station system (Agilent, Santa Clara, CA) for RNA integrity analysis. Samples with RIN$^e$ numbers above 7 were chosen to move forward with global gene expression profiling. The iScript Reverse Transcription Supermix (Bio-Rad, Hercules, CA) was used to generate the cDNA of total RNA samples. Global gene expression profiling was performed using HT-12v4 Human Gene Expression Bead Chips and a HiScan array scanning system (Illumina, Hayward, CA), according to the manufacturer's instructions. The gene expression array data have been deposited with links to an accession number GSE106936 in the Gene Expression Omnibus (GEO). Data were filtered for detection P value <0.01 in GenomeStudio (Illumina, Hayward, CA), and normalized using the LUMI package with RSN (Robust spline normalization) algorithm in R. The limma package in R was used for multivariate analysis to identify the top differentially expressed genes (P<0.01). The pheatmap package was used for clustering analysis and generating heat map representations in R. The volcano plots were obtained using the limma package in conjunction with the ggplot2 package in R. The ontology analysis of differentially expressed genes was performed using the PANTHER 12.0 (pantherdb.org/about.jsp).

T. In Vivo Studies

Six-week-old female NOD.CB17-Prkdc$^{scid}$/J mice (The Jackson Laboratory, Bar Harbor, ME) were group-housed under conditions of constant photoperiod (12 hours light: 12 hours dark) with ad libitum access to sterilized food and water. Since the animal work in this study was completed using an animal study service provided by the translational core laboratory at the University of Maryland, Baltimore, all experimental procedures and protocols utilizing mice were approved by the Institutional Animal Care and Use Committee at the University of Maryland. The clones of SK-MEL-2 cells that carry inducible NT-shRNA and NGLY1-shRNA645 were used in the animal studies. Each mouse was subcutaneously inoculated with 1×10$^6$ cancer cells in a total volume of 0.1 mL serum-free medium containing 50% Matrigel (Corning, Tewksbury, MA). As tumors became established (mean starting tumor volume: 154.2±78.3 mm$^3$ for NT-shRNA and 141.8±48.2 mm$^3$ for NGLY1-shRNA645) in mice, their ad libitum access to water was discontinued. Subsequently, sterilized water containing 0.5 mg/ml doxycycline and 5% sucrose freshly prepared every other day in bottles was provided to the tumor-bearing animals for 5 weeks. Mice bearing tumors (n=10 for NT-shRNA and n=8 for NGLY1-shRNA645) were included in the study. Tumors were measured weekly using calipers and their volumes calculated using a standard formula: width$^2$× length×0.52. Body weights were measured weekly. At terminal sacrifice, complete necropsies were performed on all mice and tumors were harvested. A portion of each tumor was frozen in liquid nitrogen for Western blotting analysis and the remainder was fixed in 10% formalin for immunohistochemical or immunofluorescence staining purposes.

U. Production of Recombinant Human NGLY1 and RNase B Deglycosylation Assay

FLAG-tagged human NGLY1 was overexpressed by the transduction of the pLenti expression vector that carries a Myc-DDK-tagged-human NGLY1 open reading frame in HEK293T cells. Anti-FLAG magnetic beads (OriGene Technologies, Rockville, MD) were used to react with the lysate of HEK293T cells overnight at 4° C. in the presence of pan-protease inhibitors to purify the FLAG-tagged NGLY1. The magnetic beads were thoroughly washed using 0.5% Tween 20 in PBS for three times to minimize non-specific binding. The enrichment of recombinant human NGLY1 was checked by Western blotting of NGLY1 in the pull-down fraction. To perform RNase B deglycosylation assays, purified human NGLY1 on an equal volume of magnetic beads was incubated with PBS containing each of the indicated small molecules and control vehicle (DMSO) at 37° C. for 2 hours. The magnetic beads were then collected and resuspended in PBS containing 0.05% NP-40. Each magnetic bead suspension was mixed with 1 ug RNase B (Millipore Sigma, St. Louis, MO) that was pre-denatured using 5 mM DTT in the presence of 8M urea at 42° C. for 1 hour followed by the treatment of 25 mM iodoacetamide at room temperature for 1 hour and buffer exchange into PBS using Zeba 7K MWCO spin columns (Thermo Fisher Scientific, Carlsbad, CA). The mixtures of magnetic bead suspension and denatured RNase B were left at 37° C. for 16 hours. The proteins in each mixture were resolved by SDS-PAGE and visualized using SYPRO Ruby gel stain (Thermo Fisher Scientific, Carlsbad, CA).

V. Proteomics Analysis

Cell samples were rinsed with PBS, harvested and snap-frozen. Each cell sample were mixed with 100 µl of resuspension buffer containing 8M urea/1% (w/v) SDS/100 mM NH$_4$HCO$_3$ and 1% protease inhibitor cocktail (Millipore Sigma, St. Louis, MO) and subsequently sonicated for 5 minutes on ice. Reduction was performed by adding 5 µl of 1M DTT and incubated for 1 hour at 30° C. Cell debris was removed by centrifugation at 14,000×g for 5 minutes at room temperature. Vivacon spin column (30 kDa MWCO; Sartorius, Göttingen Germany) was washed using 100 µL of 8 M urea/100 mM NH$_4$HCO$_3$ and spun for 10 min at 14,000×g at room temperature. After reduction, a reduced protein sample was transferred into a washed spin column and spun as described above. The spin column was washed once by adding 8 M urea/100 mM NH$_4$HCO$_3$ and spinning for 10 min at 14,000×g at room temperature. One hundred microliters of 55 mM IAA/100 mM NH$_4$HCO$_3$ was added to the spin column and allowed to incubate with reduced proteins at room temperature for 20 minutes in the dark. IAA was removed by centrifugation and the spin column was washed twice with 8M urea/100 mM NH$_4$HCO$_3$, followed by twice with 100 µL of 50 mM NH$_4$HCO$_3$. One hundred microliters of trypsin solution containing 5 µg of trypsin made in 10 mM NH$_4$HCO$_3$ was added to the spin column and allowed to incubate at 37° C. overnight. After incubation, the collection tube was replaced with a new one and 50 µL of 1% (v/v) formic acid added into the spin column and spun at 14,000×g for 10 min. This step was repeated once. Flow through containing digested peptides was transferred to an HPLC vial and allowed to dry to completeness in a speed vacuum system. Digested peptides were resuspended in 100 µL of 3% (v/v) ACN and peptide concentration was measured on a NanoDrop™ 2000/2000c Spectrophotometer (Thermo Fisher Scientific, Carlsbad, CA) at 205 nm wavelength. All samples were acidified to final concentration of 0.1% (v/v) trifluoroacetic acid.

LC-MS/MS of digested proteins was performed using an Ultimate 3000 nano-flow system (Thermo Fisher Scientific, Carlsbad, CA) coupled to a LTQ XL Orbitrap ETD MS instrument (Thermo Fisher Scientific, Carlsbad, CA). Three biological and two technical replicates per sample were performed and randomly introduced into the LC system to minimize biological and technical variability introduced by the LC-MS system. One microliter of digested peptides (equivalent to 2 µg) was drawn into a 1 µl sample loop at 300 nl/min flow rate using buffer A (2% (v/v) ACN/0.1% (v/v) FA) and sample directly flow from sample loop onto a trapping column (Acclaim PepMap100, C18, pore size 100 Å, particle size 3 µm, 75 µm ID×2 cm length; Thermo Fisher Scientific, Carlsbad, CA) and a Acclaim PepMap RSLC column (C18, pore size 100 Å, particle size 2 µm, 75 µm internal diameter×15 cm length; Thermo Fisher Scientific, Carlsbad, CA). Peptide separation started after 15 minutes using a linear gradient of 5 to 45% (v/v) buffer B (80% (v/v) ACN/0.1% (v/v) FA) over 90 min, wash step of 90% buffer B for 10 minutes before column equilibration for 20 minutes in 5% buffer B. A total of 120 min of chromatographic time. LC and MS acquisition were controlled by Xcalibur version 2.1 (Thermo Fisher Scientific, Carlsbad, CA). The LTQ XL Orbitrap MS was operated in the data-dependent mode and spectra were acquired in positive mode in full MS scans in the mass range of 300 to 2000 m/z at a resolution of 60000 in the FT mode. The ten most intense precursor ions were then selected for isolation and subjected to CID fragmentation using a dynamic exclusion of 5 seconds. Dynamic exclusion criteria included a minimum relative signal intensity of 1000, and ≥2 positive charge state. An isolation width of 3.0 m/z was used with a normalized collision energy 35.

Spectra were analyzed using the MaxQuant software (version 1.5.3.17) with the Andromeda search engine (Cox et al., 2011) against the most recent version of UniProt human database. The standard Orbitrap settings in MaxQuant were used with a MS mass error tolerance of 20 ppm and MS/MS mass error tolerance of 0.5 Da. The variable modification of oxidation of methionine and HexNAc of asparagine, and the fixed modification of carbamidomethyl of cysteines were specified, with the digestion enzyme specified as trypsin. LFQ was activated with minimum ratio count of 2 and allowed match between runs as well as unidentified features. The LC-MS/MS runs were normalized according to the least overall proteome variation where majority of the proteins do not change between the samples. The false discovery rate (FDR) was set to 5% for both proteins and peptides, with a minimum peptide length of 7 amino acids. Only unique and razor peptides were used when reporting protein identifications.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference:

U.S. Pat. No. 5,739,169
U.S. Pat. No. 5,801,005
U.S. Pat. No. 5,824,311
U.S. Pat. No. 5,830,880
U.S. Pat. No. 5,846,945
Almond & Cohen, Leukemia; 16:433-443, 2002.
Anderson et al., Cancer cell; 28(5): 653-665, 2015.
Austin-Ward and Villaseca, 1998.
Bhatia et al., Oncology (Williston Park), 23:488-496, 2009.
Bidwell et al., Nature medicine; 18(8): 1224-1231, 2012.
Biasini et al., Nucleic Acids Research, 2014.
Bukowski, et al., 1998.
Caglayan et al., European Journal of Medical Genetics, 58:39-43, 2015.
Cerezo, Cancer cell; 30(1): 183, 2016.
Chapman et al., N Engl J Med., 364:2507-2516, 2011.
Chen et al., Current Cancer Drug Targets, 11:239-253, 2011a.
Chen et al., Cold Spring Harbor Perspectives in Biology, 3:a004374, 2011b.
Christodoulides, et al., 1998.
Cox et al., J Proteome Res, 10:1794-1805, 2011.
Dang et al., RSC Adv., 4:6239-6245, 2014.
Davidson, et al., 1998.
Ellis and Hicklin, Clin Cancer Res., 15:7471-7478, 2009.
Enns et al., Genetics in Medicine, 16:751-758, 2014.
Falkenius et al., Melanoma research; 23(6): 452-460, 2013.
Flaherty et al., Nat Rev Drug Discov., 10:811-812, 2011.
Friesner et al., 2005.
Funakoshi et al., PloS One; 5:e10545, 2010.
Goplen et al., The American journal of pathology; 177(4): 1618-1628, 2010.
Greig et al., Journal of the American Chemical Society, 131:13415-13422, 2009.
Hanibuchi, et al., 1998.
Hassan et al., Oncogene; 27(33): 4557-4568, 2008.
Heeley & Shinawi, American Journal of Medical Genetics. Part A, 2015.
Hellstrand, et al., 1998.
Hodi et al., N Engl J Med., 363:711-723, 2010.
Hossain et al., Journal of Clinical Investigation, 128: 644-654, 2018
Huang et al. Proc Natl Acad Sci USA, 112:1398-1403, 2015.
Hui and Hashimoto, 1998.
Ishiguro et al., Oncogene; 20(36): 5062-5066, 2001.
Ivashkiv and Donlin, Nature reviews Immunology; 14(1): 36-49, 2014.
Jalili et al., Journal of the National Cancer Institute; 104(21): 1673-1679, 2012.
Jones et al., The Journal of Investigative Dermatology, 133:2104-2108, 2013.
Ju et al., 2000.
Koizumi et al., eLife; 5; 2016.
Kuhn et al., Blood, 110:3281-3290, 2007.
Kuo et al., Oncogene; 36(39): 5484-5496, 2017.
Lam et al., Genetics in Medicine, 2016.
Lehrbach and Ruvkun, eLife; 5; 2016.
Ley et al., J Chem Soc Perkin Trans 1, 24:3815-4195, 2000.
Li et al., Chemical Biology & Drug Design; 74:80-86, 2009.
Liao et al., Journal of Cell Science, 126:3848-3861, 2013.
Liu et al., Chemistry & Biology, 20:146-159, 2013.
Luethy and Holbrook, Cancer research; 52(1): 5-10, 1992.
Maerz et al., The Journal of Biological Chemistry; 285: 2326-2332, 2010.
March's Advanced Organic Chemistry: Reactions, Mechanisms, and Structure, 2007.
Marks, Expert Opinion on Investigational Drug, 19:1049-1066, 2010.
Misaghi et al., Chemistry & Biology; 11:1677-1687, 2004.
Mitchell, et al., 1990.
Mitchell, et al., 1993.
Morris et al., Journal of Computational Chemistry, 30:2785-2791, 2009.
Morton, et al., 1992.
Muller et al., Nat Methods; 8(4): 315-317, 2011.
Nazor et al., Cell Stem Cell, 10:620-634, 2012.
Need et al. Journal of Medical Genetics, 49:353-361, 2012.
Orita et al., Chemistry, 7:3321-3327, 2001.
Orlowski and Kuhn, Clinical Cancer Research, 14:1649-1657, 2008.

Owings et al., Human molecular genetics; 27(6): 1055-1066, 2018.
Pietras, et al., 1998.
Premdjee et al., Bioorganic & medicinal chemistry, 21:4973-4975, 2011.
Qin et al., 1998.
Ravindranath and Morton, 1991.
Remington's Pharmaceutical Sciences, 15th Edition, pages 1035-1038 and 1570-1580.
Reu et al., Journal of clinical oncology: official journal of the American Society of Clinical Oncology; 24(23): 3771-3779, 2006.
Rosenberg, et al., 1988.
Rosenberg, et al., 1989.
Slipicevic et al., BMC cancer; 8: 276, 2008.
Sondak et al., Nat Rev Drug Discov., 10:411-412, 2011.
Singh et al., Nature Reviews. Drug Discovery, 10:307-317, 2011.
Suzuki, T. Journal of Biochemistry; 157:23-34, 2015.
Tomlin et al., ACS Cent Sci 2017.
Toyama and Hetzer, Nature Reviews. Molecular Cell Biology, 14:55-61, 2013.
Tropper et al., Synthesis, 618-620, 1992.
Tsabedze et al., Tetrahedron Letters, 54:6983-6985, 2013.
Tseng et al., Mol Pharmacol., 70:1534-1541, 2006.
Vert et al., Oncotarget 2017; 8(7): 11692-11707.
Wang et al., Cancer Research, 68:2820-2830, 2008.
Wang et al., Cell Research, 21:1551-1563, 2011.
Wang et al., Cell research; 24(2): 143-160, 2014.
Wang et al., Scientific reports; 7: 41715, 2017.
Witte et al., The Journal of Organic Chemistry, 74:605-616, 2009.
Wolkenberg et al., Current Opinion in Drug Discovery & Development, 8:701-708, 2005.
Yang et al., Cancer research; 70(13): 5518-5527, 2010.
Zhao et al., The Journal of Biological Chemistry, 281: 13751-13761, 2006.

---

What is claimed is:

1. A method of treating a cancer in a patient, wherein the cancer has an upregulation of NGLY1, comprising administering to the patient a therapeutically effective amount of an inhibitor of N-glycanase 1 (NGLY1), wherein said inhibitor of NGLY1 is a compound of formula:

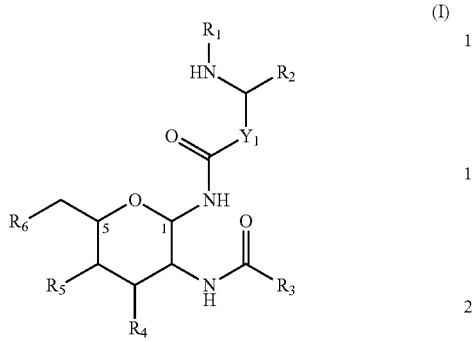

(I)

wherein:
- $R_1$ is a thiol-reactive group;
- $R_2$ is hydrogen, alkyl$_{(C \leq 6)}$, substituted alkyl$_{(C \leq 6)}$, or —C(O)NR$_7$R$_8$; wherein:
  - $R_7$ and $R_8$ are each independently hydrogen, alkyl$_{(C \leq 6)}$, or substituted alkyl$_{(C \leq 6)}$; or
  - $R_7$ and $R_8$ when taken together are heterocycloalkyl$_{(C \leq 12)}$, heteroaryl$_{(C \leq 12)}$, or a substituted version of any of these groups;
- $Y_1$ is a covalent bond, alkanediyl$_{(C \leq 6)}$, or substituted alkanediyl$_{(C \leq 6)}$;
- $R_3$ is alkyl$_{(C \leq 6)}$ or substituted alkyl$_{(C \leq 6)}$;
- $R_4$ and $R_5$ are each independently hydrogen, hydroxy, or —OC(O)R$_9$; wherein:
  - $R_9$ is hydrogen, alkyl$_{(C \leq 6)}$ or substituted alkyl$_{(C \leq 6)}$; and
- $R_6$ is hydrogen, —OC(O)R$_{10}$, —NR$_{11}$C(O)R$_{10}$, —NR$_{11}$(CH$_2$)$_m$R$_{10}$, —NR$_{12}$R$_{13}$, or —O(CH$_2$)$_m$R$_{10}$; wherein:
  - m is 0, 1, or 2;
  - $R_{10}$ is alkyl$_{(C \leq 8)}$, cycloalkyl$_{(C \leq 8)}$, heterocycloalkyl$_{(C \leq 8)}$, aryl$_{(C \leq 12)}$, heteroaryl$_{(C \leq 12)}$, or a substituted version of any of these groups;
  - $R_{11}$ is hydrogen, alkyl$_{(C \leq 6)}$, or substituted alkyl$_{(C \leq 6)}$;
  - $R_{12}$ and $R_{13}$ when taken together are heterocycloalkyl$_{(C \leq 8)}$, heteroaryl$_{(C \leq 12)}$, or a substituted version of any of these groups;

or a pharmaceutically acceptable salt thereof.

2. The method of claim 1, wherein the cancer is melanoma, ovarian cancer, breast cancer, cervical cancer, endometrial cancer, colon cancer, pancreatic cancer, prostate cancer, liver cancer, renal cancer, lung cancer, glioma, and lymphoma.

3. The method of claim 1, wherein the cancer is not multiple myeloma.

4. The method of claim 3, wherein the cancer is not a hematologic cancer.

5. The method according to claim 1, wherein the cancer is associated with the dysregulation of NGLY1.

6. The method of claim 1 further comprising identifying a patient with a cancer which shows dysregulated expression of NGLY1.

7. The method of claim 1, wherein the method further comprises a second cancer therapy.

8. The method of claim 7, wherein the second cancer therapy is surgery, a second chemotherapeutic agent, a radiotherapy, or an immunotherapy.

9. The method according to claim 1, wherein the patient is a mammal.

10. The method of claim 9, wherein the patient is a human.

11. The method according to claim 1, wherein the method comprises administering the compound once.

* * * * *

SEQUENCE LISTING

```
<160> NUMBER OF SEQ ID NOS: 9

<210> SEQ ID NO 1
<211> LENGTH: 64
<212> TYPE: RNA
<213> ORGANISM: Artificial Sequence
<220> FEATURE:
<223> OTHER INFORMATION: Synthetic oligoribonucleotide

<400> SEQUENCE: 1
ccgaguuuca aauaacaauc aauagugaag ccacagaugu auugauuguu auuugaaacu      60
cgau                                                                  64

<210> SEQ ID NO 2
<211> LENGTH: 64
<212> TYPE: RNA
<213> ORGANISM: Artificial Sequence
<220> FEATURE:
<223> OTHER INFORMATION: Synthetic oligoribonucleotide

<400> SEQUENCE: 2
aaagcauuac uucgagacac uauagugaag ccacagaugu auagugucuc gaaguaaugc      60
uucu                                                                  64

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
cattcaacag ctcctctgac                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
gatctgatga ctgcccttga                                                 20
```

```
<210> SEQ ID NO 5
<211> LENGTH: 64
<212> TYPE: DNA
<213> ORGANISM: Artificial Sequence
<220> FEATURE:
<223> OTHER INFORMATION: Synthetic oligoribonucleotide

<400> SEQUENCE: 5
ccgaguuuca aauaacaauc aauagugaag ccacagaugu auugauuguu auuugaaacu      60
cgau                                                                  64

<210> SEQ ID NO 6
<211> LENGTH: 64
<212> TYPE: DNA
<213> ORGANISM: Artificial Sequence
<220> FEATURE:
<223> OTHER INFORMATION: Synthetic oligoribonucleotide

<400> SEQUENCE: 6
aaagcauuac uucgagacac uauagugaag ccacagaugu auagugucuc gaaguaaugc      60
uucu                                                                  64

<210> SEQ ID NO 7
<211> LENGTH: 64
<212> TYPE: DNA
<213> ORGANISM: Artificial Sequence
<220> FEATURE:
<223> OTHER INFORMATION: Synthetic oligoribonucleotide

<400> SEQUENCE: 7
aagguccugu cuucagauga aauagugaag ccacagaugu auuucaucug aagacaggac      60
cucu                                                                  64

<210> SEQ ID NO 8
<211> LENGTH: 64
<212> TYPE: RNA
<213> ORGANISM: Artificial Sequence
<220> FEATURE:
<223> OTHER INFORMATION: Synthetic oligoribonucleotide

<400> SEQUENCE: 8
agagaaagaa caggagaaug aauagugaag ccacagaugu auucauucuc cuguucuuuc      60
uccu                                                                  64

<210> SEQ ID NO 9
<211> LENGTH: 64
<212> TYPE: RNA
<213> ORGANISM: Artificial Sequence
<220> FEATURE:
<223> OTHER INFORMATION: Synthetic oligoribonucleotide

<400> SEQUENCE: 9
aguccugucu ucagaugaaa aauagugaag ccacagaugu auuuucauc ugaagacagg       60 accu                                                                  64
```